(12) United States Patent
Rastelli et al.

US011564986B2

(10) Patent No.: US 11,564,986 B2
(45) Date of Patent: Jan. 31, 2023

(54) APPROACH FOR TREATMENT OF CANCER VIA IMMUNOMODULATION BY USING TALABOSTAT

(71) Applicant: ONKOSXCEL THERAPEUTICS, LLC, New Haven, CT (US)

(72) Inventors: Luca Rastelli, Norwell, MA (US); Aparna Katoch Sapra, Mumbai (IN); Vimal Mehta, Guilford, CT (US)

(73) Assignee: ONKOSXCEL THERAPEUTICS, LLC, New Haven, CT (US)

( * ) Notice: Subject to any disclaimer, the term of this patent is extended or adjusted under 35 U.S.C. 154(b) by 0 days.

(21) Appl. No.: 15/467,781

(22) Filed: Mar. 23, 2017

(65) Prior Publication Data
US 2017/0266280 A1 Sep. 21, 2017

Related U.S. Application Data

(63) Continuation-in-part of application No. PCT/US2016/042798, filed on Jul. 18, 2016.

(60) Provisional application No. 62/204,495, filed on Aug. 13, 2015, provisional application No. 62/193,348, filed on Jul. 16, 2015.

(51) Int. Cl.
| | | |
|---|---|---|
| *A61K 39/395* | (2006.01) | |
| *A61K 31/69* | (2006.01) | |
| *A61K 39/00* | (2006.01) | |
| *C07K 16/28* | (2006.01) | |
| *A61K 38/04* | (2006.01) | |
| *C12N 15/113* | (2010.01) | |
| *A61K 45/06* | (2006.01) | |

(52) U.S. Cl.
CPC .......... *A61K 39/3955* (2013.01); *A61K 31/69* (2013.01); *A61K 38/04* (2013.01); *A61K 39/39541* (2013.01); *A61K 45/06* (2013.01); *C07K 16/2818* (2013.01); *C12N 15/1137* (2013.01); *A61K 2039/505* (2013.01); *A61K 2039/545* (2013.01); *C07K 2317/21* (2013.01); *C07K 2317/76* (2013.01); *C12N 2310/14* (2013.01); *C12N 2320/31* (2013.01)

(58) Field of Classification Search
CPC ............... A61K 39/3955; A61K 31/69; A61K 2039/545; C01K 16/2818; C07K 2317/21; C07K 2317/76
See application file for complete search history.

(56) References Cited

U.S. PATENT DOCUMENTS

| | | |
|---|---|---|
| 5,811,097 A | 9/1998 | Allison et al. |
| 5,855,887 A | 1/1999 | Allison et al. |
| 5,977,318 A | 11/1999 | Linsley et al. |
| 6,051,227 A | 4/2000 | Allison et al. |
| 6,207,156 B1 | 3/2001 | Kuchroo et al. |
| 6,682,736 B1 | 1/2004 | Hanson et al. |
| 6,825,169 B1 | 11/2004 | Bachovchin et al. |
| 6,890,904 B1 | 5/2005 | Wallner et al. |
| 6,949,514 B2 * | 9/2005 | Wallner ................. A61K 31/69 514/19.5 |
| 6,984,720 B1 | 1/2006 | Korman et al. |
| 7,034,121 B2 | 4/2006 | Carreno et al. |
| 7,109,003 B2 | 9/2006 | Hanson et al. |
| 7,132,281 B2 | 11/2006 | Hanson et al. |
| 7,265,118 B2 | 9/2007 | Wallner |
| 7,452,535 B2 | 11/2008 | Davis et al. |
| 7,488,802 B2 | 2/2009 | Collins et al. |
| 7,605,238 B2 | 10/2009 | Korman et al. |
| 7,858,746 B2 | 12/2010 | Honjo et al. |
| 7,928,202 B2 | 4/2011 | Frank et al. |
| 7,943,743 B2 | 5/2011 | Korman et al. |
| 8,008,449 B2 | 8/2011 | Korman et al. |
| 8,217,149 B2 | 7/2012 | Irving et al. |
| 8,552,154 B2 | 10/2013 | Freeman et al. |
| 8,609,089 B2 | 12/2013 | Langermann et al. |
| 8,642,557 B2 | 2/2014 | Akamatsu et al. |
| 8,697,845 B2 | 4/2014 | Ward et al. |
| 8,735,553 B1 | 5/2014 | Li et al. |
| 8,741,295 B2 | 6/2014 | Olive |
| 8,779,108 B2 | 7/2014 | Queva et al. |
| 8,907,053 B2 | 12/2014 | Sasikumar et al. |
| 8,927,697 B2 | 1/2015 | Davis et al. |
| 8,993,731 B2 | 3/2015 | Tyson |
| 9,029,315 B2 | 5/2015 | Chen et al. |
| 9,102,727 B2 | 8/2015 | Freeman et al. |
| 9,102,728 B2 | 8/2015 | Tyson |
| 9,181,342 B2 | 11/2015 | Davis |
| 9,266,946 B2 | 2/2016 | Frank et al. |
| 9,724,413 B2 | 8/2017 | Maecker et al. |

(Continued)

FOREIGN PATENT DOCUMENTS

| | | |
|---|---|---|
| CN | 104479020 A | 4/2015 |
| CN | 104761633 A | 7/2015 |
| CN | 105175544 A | 12/2015 |
| FR | 2 703 251 | 10/1994 |
| JP | 2014-513079 A | 5/2014 |

(Continued)

OTHER PUBLICATIONS

Schiffman et al., The New England Journal of Medicine, Vo. 353, No. 20, p. 2101-2104, 2005 (Year: 2005).*
Cuzick et al. (The Lancet, vol. 361, p. 296-300, 2003) (Year: 2003).*

(Continued)

*Primary Examiner* — Mark Halvorson
*Assistant Examiner* — Dennis J Sullivan
(74) *Attorney, Agent, or Firm* — Cooley LLP

(57) ABSTRACT

The present invention discloses a method of treating, preventing or ameliorating tumor growth by administering a therapeutic agent that selectively inhibits dipeptidyl peptidase including fibroblast activation protein and dipeptidyl peptidase 8/9 in combination with an immune checkpoint inhibitor. The method specifically discloses use of Talabostat in combination with an immune checkpoint inhibitor, its pharmaceutical composition and process of preparing such composition.

9 Claims, 14 Drawing Sheets

Specification includes a Sequence Listing.

(56) References Cited

U.S. PATENT DOCUMENTS

| | | |
|---|---|---|
| 2009/0081157 A1 | 3/2009 | Kornbluth et al. |
| 2009/0252741 A1 | 10/2009 | Liu et al. |
| 2010/0028330 A1 | 2/2010 | Collins et al. |
| 2010/0278828 A1 | 11/2010 | Jure-Kunkel |
| 2010/0292153 A1 | 11/2010 | Strober |
| 2012/0114649 A1 | 5/2012 | Langermann et al. |
| 2013/0017199 A1 | 1/2013 | Langermann |
| 2013/0022629 A1 | 1/2013 | Sharpe et al. |
| 2013/0309250 A1 | 11/2013 | Cogswell et al. |
| 2014/0105914 A1 | 4/2014 | Jones et al. |
| 2014/0271725 A1 | 9/2014 | Bachovchin |
| 2014/0302031 A1 | 10/2014 | Frank et al. |
| 2014/0335048 A1 | 11/2014 | Stogniew et al. |
| 2014/0341902 A1 | 11/2014 | Maecker et al. |
| 2014/0341917 A1 | 11/2014 | Nastri et al. |
| 2015/0125447 A1 | 5/2015 | Heider |
| 2015/0203579 A1 | 7/2015 | Papadopoulos et al. |
| 2015/0210769 A1 | 7/2015 | Freeman et al. |
| 2015/0232555 A1 | 8/2015 | Carven et al. |
| 2015/0355184 A1 | 12/2015 | Pierce et al. |
| 2016/0052990 A1 | 2/2016 | Ring et al. |
| 2016/0058852 A1 | 3/2016 | Ter Meulen et al. |
| 2016/0075783 A1 | 3/2016 | King et al. |
| 2016/0108123 A1 | 4/2016 | Freeman et al. |
| 2016/0148513 A1 | 5/2016 | Beaurepaire |
| 2016/0159905 A1 | 6/2016 | Abdiche et al. |
| 2016/0237154 A1 | 8/2016 | Gray et al. |
| 2016/0251436 A1 | 9/2016 | Amirina et al. |
| 2016/0272708 A1 | 9/2016 | Chen |
| 2016/0319018 A1 | 11/2016 | Morsey et al. |
| 2017/0056448 A1 | 3/2017 | Glick et al. |
| 2017/0128539 A1 | 5/2017 | Addepalli et al. |
| 2017/0158770 A1 | 6/2017 | Bedi et al. |
| 2017/0239351 A1 * | 8/2017 | Hamdy ............ A61K 39/39558 |
| 2017/0290914 A1 * | 10/2017 | Liang ................. C07K 16/2818 |
| 2018/0064787 A1 | 3/2018 | Schreiber et al. |
| 2018/0134771 A1 | 5/2018 | Nandabalan et al. |
| 2018/0148513 A1 | 5/2018 | Afar et al. |
| 2018/0256711 A1 | 9/2018 | Rhee et al. |
| 2019/0008918 A1 | 1/2019 | Upmanyu et al. |
| 2020/0317784 A1 | 10/2020 | Nandabalan et al. |

FOREIGN PATENT DOCUMENTS

| | | | |
|---|---|---|---|
| WO | WO 00/037504 A1 | 6/2000 | |
| WO | WO 2001/014424 A2 | 3/2001 | |
| WO | WO 2007/014754 A1 | 2/2007 | |
| WO | WO 2007/058957 A2 | 5/2007 | |
| WO | WO 2007/059099 A2 | 5/2007 | |
| WO | WO 2007/127204 A2 | 11/2007 | |
| WO | WO 2008/033368 A2 | 3/2008 | |
| WO | WO2008/066729 * | 6/2008 | |
| WO | WO 2010/065711 A1 | 6/2010 | |
| WO | WO 2010/077634 A1 | 7/2010 | |
| WO | WO 2011/066342 A2 | 6/2011 | |
| WO | WO 2013/078059 A1 | 5/2013 | |
| WO | WO 2014/144600 A2 | 9/2014 | |
| WO | WO 2015/058573 A1 | 4/2015 | |
| WO | WO 2015/069770 A1 | 5/2015 | |
| WO | WO 2015/095423 A2 | 6/2015 | |
| WO | WO-2015095811 A2 * | 6/2015 | ......... A61K 39/0011 |
| WO | WO 2015/100282 A1 | 7/2015 | |
| WO | WO 2016/015685 A1 | 2/2016 | |
| WO | WO 2016/019270 A1 | 2/2016 | |
| WO | WO 2016/077397 A2 | 5/2016 | |
| WO | WO 2016/179576 A1 | 11/2016 | |
| WO | WO 2016/197497 A1 | 12/2016 | |
| WO | WO 2016/205277 A1 | 12/2016 | |
| WO | WO 2017/011831 A1 | 1/2017 | |
| WO | WO 2017/020974 A1 | 2/2017 | |
| WO | WO 2017/058881 A1 | 4/2017 | |
| WO | WO 2017/079303 A1 | 5/2017 | |
| WO | WO 2017/118864 A1 | 7/2017 | |
| WO | WO 2017/156152 A1 | 9/2017 | |
| WO | WO 2018/049015 A1 | 3/2018 | |
| WO | WO 2018/049027 A1 | 3/2018 | |
| WO | WO 2018/129497 A1 | 7/2018 | |
| WO | WO 2019/094916 A1 | 5/2019 | |
| WO | WO 2020/123477 A1 | 6/2020 | |
| WO | WO 2020/123496 A1 | 6/2020 | |

OTHER PUBLICATIONS

Hernandez-Ledesma (Peptides, vol. 30, p. 426-430, 2009) (Year: 2009).*
Rudikoff et al. (Proceedings of the National Academy of Sciences USA, vol. 79, p. 1979-1983, 1982) (Year: 1982).*
Paul, Fundamental Immunology, 3rd Edition, 1993, pp. 292-295 (Year: 1993).*
Bendig M. M. (Methods: A Companion to Methods in Enzymology, 1995; 8:83-93) (Year: 1995).*
Komenaka et al., Clinics in Dermatology, 2004, vol. 22, p. 251-265 (Year: 2004).*
Evans et al. (Q. J. Med 1999: 92: 299-307) (Year: 1999).*
Eager (BMC Cancer, vol. 9, No. 263, p. 1-11, 2009) (Year: 2009).*
Dhupkar et al., "Immune modulation through targeting PD-1/PDL-1 signaling pathway for the treatment of osteosarcoma lung metastastasis," Journal for the Immunotherapy of Cancer, Nov. 2015, vol. 3, Supp. 2, Abstract No. P218, 2 pages.
Extended European Search Report for European Application No. 18875308.1 dated Dec. 1, 2021, 14 pages.
Huang et al., "IL-2 synergizes with PD-1/PD-L1 blockade via CD 28/CHK1 pathway to enhance CD81 T cell responses in lung squamous cell carcinoma," Annals of Oncology, 2016, Abstract 396PD, vol. 27, Suppl 9, ix123-ix125.
Márquez-Rodas et al., "Immune checkpoint inhibitors: therapeutic advances in melanoma," Annals of Translational Medicine, 2015, vol. 3, No. 18, 16 pages.
Medina and Adams, "PD-1 Pathway Inhibitors: Immuno-Oncology Agents for Restoring Antitumor Immune Responses," Pharmacotherapy 2016;36(3):317-334.
Mullin, E., "Nektar Presents Positive Preclinical Data for NKTR-214, a Novel Cancer Immunotherapy, at 50th ASCO Meeting," Jun. 2, 2014, 4 pages, retrieved from https://www.fiercebiotech.com/research/nektar-presents-positive-preclinical-data-for-nktr-214-a-novel-cancer-immunotherapy-at.
Raedler et al., "Opdivo (Nivolumab): Second PD-1 Inhibitor Receives FDA Approval for Unresectable or Metastatic Melanoma," American Health & Drug Benefits, Mar. 2015, vol. 8, pp. 180-183.
West et al., "PD-L1 blockade synergizes with IL-2 therapy in reinvigorating exhausted T cells," J Clin Invest. 2013; 123(6): 2604-2615.
Xu-Monette et al., "PD-1/PD-L1 Blockade: Have We Found the Key to Unleash the Antitumor Immune Response?" Front. Immunol. (2017) 8: 1597, 29 pages.
Extended European Search Report for European Application No. 16825310.2 dated Feb. 5, 2019, 7 pages.
BioXcel Therapeutics Inc, "A Trial of BXCL701 and Pembrolizumab in Patients With mCRPC," ClinicalTrials.gov, Apr. 10, 2019, 2 pages.
Crownbio, "0X40 agonist: strengthen cancer immunotherapy," Aug. 29, 2017, retrieved from https://www.crownbio.cn/blog/ox40-ox40l-immune-co-stimulators/, 10 pages (English machine translation only).
Graff et al., "Early evidence of anti-PD-1 activity in enzalutamide-resistant prostate cancer," Oncotarget, Jul. 12, 2016, vol. 7, No. 33, pp. 52810-52817.
International Search Report and Written Opinion of the International Searching Authority for International Application No. PCT/US2021/016764, dated Apr. 16, 2021, 13 pages.
Martin et al., "Paucity of PD-L1 expression in prostate cancer: innate and adaptive immune resistance," Prostate Cancer and Prostatic Diseases (2015) 18, 325-332.
Blank et al., "Interaction of PD-L1 on tumor cells with PD-1 on tumor-specific T cells as a mechanism of immune evasion: implications for tumor immunotherapy." Cancer Immunology, Immunotherapy (2005); 54(4): 307-314.

(56) References Cited

OTHER PUBLICATIONS

Brown et al., "Blockade of Programmed Death-1 Ligands on Dendritic Cells Enhances T Cell Activation and Cytokine Production." The Journal of Immunology (2003); 170(3): 1257-1266.

Corbett et al., "Response of transplantable tumors of mice to anthracenedione derivatives alone and in combination with clinically useful agents." Cancer Treatment Reports (1982); 66(5): 1187-1200.

Dong et al., "B7-H1 pathway and its role in the evasion of tumor immunity." Journal of Molecular Medicine (2003); 81(5): 281-287.

International Preliminary Report on Patentability for International Application No. PCT/US2016/042798 dated Aug. 3, 2017, 21 pages.

International Preliminary Report on Patentability for International Application No. PCT/US2016/031399 dated Nov. 7, 2017, 10 pages.

International Search Report and Written Opinion for International Application No. PCT/US2016/031399 dated Aug. 19, 2016, 13 pages.

Iwai et al., "Involvement of PD-L1 on tumor cells in the escape from host immune system and tumor immunotherapy by PD-L1 blockade." PNAS (2002); 99(19): 12293-12297.

Konishi et al., "B7-H1 Expression on Non-Small Cell Lung Cancer Cells and Its Relationship with Tumor-Infiltrating Lymphocytes and Their PD-1 Expression." Clinical Cancer Research (2004); 10(15): 5094-5100.

Mahoney et al., "The Next Immune-Checkpoint Inhibitors: PD-1/PD-L1 Blockade in Melanoma." Clinical Therapeutics (2015); 37(4): 764-782.

Schatton et al., "ABCB5 Identifies Immunoregulatory Dermal Cells." Cell Reports (2015); 12(10): 1564-1574.

Somasundaram et al., "Chapter Eleven—Intratumoral Heterogeneity as a Therapy Resistance Mechanism: Role of Melanoma Subpopulations." Advances in Pharmacology (2012); 65: 335-359.

Wilson et al., "ABCB5 Maintains Melanoma-Initiating Cells through a Proinflammatory Cytokine Signaling Circuit." Cancer Research (2014); 74(15): 4196-4207.

Agarwal et al., "Abstract LB-077: Dipeptidyl Peptidase Inhibitor BXCL701 synergizes with an OX40-agonist antibody resulting in synergistic anti-tumor response and survival in an animal model of colorectal cancer by bridging the innate and adaptive arms of the immune system," AACR Annual Meeting 2019, Mar. 29-Apr. 3, 2019, Atlanta, GA, Cancer Res 2019, 79(13 Suppl):Abstract LB-077, 4 pages.

Almagro et al., "Humanization of antibodies," Frontiers in Bioscience, Jan. 2008, 13, 1619-1633.

Brahmer et al., "Safety and Activity of Anti-PD-L1 Antibody in Patients with Advanced Cancer," N Engl J Med., Jun. 28, 2012; 366(26): 2455-2465.

Bu et al., "Learning from PD-1 Resistance: New Combination Strategies," Trends in Molecular Medicine, Jun. 2016, vol. 22, No. 6, pp. 448-451.

Camacho et al., "Phase 1 clinical trial of anti-CTLA4 human monoclonal antibody CP-675,206 in patients (pts) with advanced solid malignancies," Journal of Clinical Oncology 22, No. 14_suppl (Jul. 15, 2004) 2505-2505. DOI: 10.1200/jco.2004.22.90140.2505.

Cunningham et al., "Phase 2 trial of talabostat and cisplatin in patients with stage IV melanoma," Journal of Clinical Oncology, Abstract 8040, vol. 24, No. 18_suppl (Jun. 20, 2006), 2 pages.

De Genst et al., "Antibody repertoire development in camelids," Developmental and Comparative Immunology (2006) 30, 187-198.

Hewitt et al., "Immuno-inhibitory PD-L1 can be induced by a Peptidoglycan/NOD2 mediated pathway in primary monocytic cells and is deficient in Crohn's patients with homozygous NOD2 mutations," Clinical Immunology, 2012, vol. 143, pp. 162-169.

Hurwitz et al., "CTLA-4 blockade synergizes with tumor-derived granulocyte-macrophage colony—stimulating factor for treatment of an experimental mammary carcinoma," PNAS USA, Aug. 1998, vol. 97, pp. 10067-10071.

International Search Report and Written Opinion for International Application No. PCT/US2017/021400 dated Jun. 9, 2017, 10 pages.

International Search Report and Written Opinion for International Application No. PCT/US2019/065465, dated Feb. 11, 2020, 9 pages.

International Search Report and Written Opinion for International Application No. PCT/US2019/065432, dated Feb. 27, 2020, 13 pages.

Kager et al., "Review of mifamurtide in the treatment of patients with osteosarcoma," Therapeutics and Clinical Risk Management 2010:6 279-286.

Mokyr et al., "Realization of the Therapeutic Potential of CTLA-4 Blockade in Low-Dose Chemotherapy-treated Tumor-bearing Mice," Cancer Research, Dec. 1998, 58:5301-5304.

Topalian et al., "Safety, Activity, and Immune Correlates of Anti-PD-1 Antibody in Cancer," N Engl J Med., Jun. 28, 2012; 366(26): 2443-2454.

Yoshinaga et al., "Ig L-chain Shuffling for Affinity Maturation of Phage Library-derived Human Anti-human MCP-1 Antibody Blocking its Chemotactic Activity," J. Biochem., (2008) 143, 593-601.

Adams et.al, "PT-100, a Small Molecule Dipeptidyl Peptidase Inhibitor, Has Potent Antitumor Effects and Augments Antibody-Mediated Cytotoxicity via a Novel Immune Mechanism," Cancer Research 64, 5471-5480, Aug. 1, 2004.

Duncan et al., "A pan-inhibitor of DASH family enzymes induces immunemediated regression of murine sarcoma and is a potent adjuvant to dendritic cell vaccination and adoptive T-cell therapy" J Immunother. Oct. 2013 ; 36(8), 21 pages.

Egger et al., "Effects of the fibroblast activation protein inhibitor, PT100, in a murine model of pulmonary fibrosis," European Journal of Pharmacology, vol. 809, Aug. 15, 2017, pp. 64-72.

Da Silva et al., "Dipeptidylpeptidase 4 inhibition enhances lymphocyte trafficking, improving both naturally occurring tumor immunity and immunotherapy," Nature Immunology vol. 16, No. 8, Aug. 2015.

Wong et al., "Neuropeptide Y is a physiological substrate of fibroblast activationprotein: Enzyme kinetics in blood plasma and expression of Y2R andY5R in human liver cirrhosis and hepatocellular carcinoma," Peptides 75 (2016) 80-95.

Feig et al., "Targeting CXCL12 from FAP—expressing carcinoma-associated fibroblasts synergizes with anti-PD-L1 immunotherapy in pancreatic cancer," Proc. Natl. Acad. Sci. USA 110(50):20212-20217 (2013).

International Search Report, PCT Appl. No. PCT/US2016/042798, 4 pages (dated Oct. 17, 2016).

Jansen et al., "Selective Inhibitors of Fibroblast Activation Protein (FAP) with a (4-Quinolinoyl)-glycyl-2-cyanopyrrolidine Scaffold," ACS Med. Chem. Lett. 4:491-496 (2013).

Walsh et al., "Val-BoroPro Accelerates T Cell Priming via Modulation of Dendritic Cell Trafficking Resulting in Complete Regression of Established Murine Tumors," PLoS ONE 8(3): e58860, 13 pages (2013).

Written Opinion of the International Searching Authority, PCT Appl. No. PCT/US2016/042798, 9 pages (dated Oct. 17, 2016).

Berglund et al., "The epitope space of the human proteome," Protein Science (2008), 17:606-613.

Charych et al., "NKTR-214, an Engineered Cytokine with Biased IL2 Receptor Binding, Increased Tumor Exposure, and Marked Efficacy in Mouse Tumor Models," Clin Cancer Res; 22(3) Feb. 1, 2016, pp. 680-690.

Corada et al., "Monoclonal antibodies directed to different regions of vascular endothelial cadherin extracellular domain affect adhesion and clustering of the protein and modulate endothelial permeability," Blood, 2001; 97:1679-1684.

International Search Report and Written Opinion of the International Searching Authority for International Application No. PCT/US2018/060699, dated Jan. 28, 2019, 13 pages.

Kulkarni-Kale et al., "CEP: a conformational epitope prediction server," Nucleic Acids Research, 2005, vol. 33, W168-W171, Web Server issue.

Moreno et al., "Anti-PD-1 Therapy in Melanoma," Semin Oncol, 2015, 42:466-473.

(56) References Cited

OTHER PUBLICATIONS

Padlan, E.A., "X-Ray Crystallography of Antibodies," Advances in Protein Chemistry, 1996, 49:57-133.

Aggarwal et al., "Safety of BXCL701, a small molecule inhibitor of dipeptidyl peptidases (DPP), with pembrolizumab, (pembro, anti-PD-1) monoclonal antibody, in men with metastatic castration-resistant prostate cancer (mCRPC)," Journal of Clinical Oncology, Feb. 20, 2020, 38, No. 6_suppl, Abstract 140, 4 pages.

Bauernfried and Hornung, "DPP9 restrains NLRP1 activation," Nat Struct Mol Biol. Apr. 2021;28(4):333-336.

Coulombe et al., "Muramyl Dipeptide Induces NOD2-Dependent Ly6C$^{high}$Monocyte Recruitment to the Lungs and Protects Against Influenza Virus Infection," PLoS One, 2012, vol. 7, No. 5, e36734, 11 pages).

Cross et al., "Therapeutic DNA vaccination against colorectal cancer by targeting the MYB oncoprotein," Clinical & Translational Immunology, 2015, 4, e30, 10 pages.

Extended European Search Report for European Application No. 19894733.5 dated Jul. 19, 2022, 5 pages.

Extended European Search Report for European Application No. 19896460.3 dated Jul. 28, 2022, 8 pages.

Gai et al., "DPP8/9 inhibitors are universal activators of functional NLRP1 alleles," Cell Death & Disease (2019) 10:587, 10 pages.

Griswold et al., "DPP9's Enzymatic Activity and Not Its Binding to CARD8 Inhibits Inflammasome Activation," ACS Chem. Biol. 2019, 14, 2424-2429.

Guo et al., "Combined Trabectedin and anti-PD1 antibody produces a synergistic antitumor effect in a murine model of ovarian cancer," Journal of Translational Medicine, 2015, 13:247, 13 pages.

Johnson et al., Nat Med. Aug. 2018; 24(8): 1151-1156, Supplementary materials, 26 pages.

Johnson et al., "DPP8/9 inhibitor-induced pyroptosis for treatment of acute myeloid leukemia," Nat Med. Aug. 2018; 24(8): 1151-1156, 17 pages.

Linch et al., "OX40 Agonists and Combination Immunotherapy: Putting the Pedal to the Metal," Frontiers in Oncology, 2015, vol. 5, Article 34, 14 pages.

Okondo et al., "Inhibition of Dpp8/9 Activates the Nlrp1b Inflammasome," Cell Chemical Biology 2018, 25, 262-267.

Ruby et al., "The effect of aging on OX40 agonist-mediated cancer immunotherapy", Cancer Immunol Immunother (2009) 58:1941-1947.

Sandrine et al., "Rationale for anti-OX40 cancer immunotherapy", European Journal of Cancer (2016) 52: 50-66.

Zhong et al., "Human DPP9 represses NLRP1 inflammasome and protects against autoinflammatory diseases via both peptidase activity and FIIND domain binding," J. Biol. Chem. (2018) 293(49) 18864-18878.

\* cited by examiner

APPROACH FOR TREATMENT OF CANCER VIA IMMUNOMODULATION BY USING TALABOSTAT

CROSS REFERENCE TO RELATED APPLICATIONS

This application is a continuation-in-part of International Application No. PCT/US2016/042798, filed Jul. 18, 2016, which claims the benefit of priority to U.S. provisional application Ser. No. 62/193,348, filed Jul. 16, 2015, and U.S. provisional application Ser. No. 62/204,495, filed Aug. 13, 2015, each of which is incorporated herein by reference in their entirety for all purposes.

FIELD OF THE INVENTION

The present invention is in the field of immune-oncology. More specifically relates to treatment of cancer or tumor through immunomodulation using therapeutic agents including small molecules, antibodies, nanobodies, engineered peptides, engineered receptors, autologous immune enhancement approach or siRNA that selectively inhibits dipeptidyl peptidase (for example, fibroblast activation protein (FAP) or dipeptidyl peptidase 8/9 (DPP 8/9)) in combination with an immune checkpoint inhibitor(s) which lead to immunomodulation. Preferred selective dipeptidyl peptidase inhibitor is a small molecule e.g. Talabostat.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: BIOX_008_02US_SeqList, date recorded: Mar. 22, 2017; file size: 6 kilobytes).

BACKGROUND

Cancer is a multistep process that begins with minor pre-neoplastic changes, which may progress to neoplasia, the neoplastic lesions possibly developing an increasing capacity for invasion, growth, metastasis, and heterogeneity. Current therapies for the treatment of cancer involve surgery, hormonal therapy, radiation therapy, chemotherapy and immunotherapy. Immunotherapy for the treatment of cancer has evolved alongside our improved understanding of immune system. In particular, an appreciation of the ability of cancer cells to subvert the antitumor immune response has provided a rationale for the development of novel immunotherapies that target immune checkpoints responsible for the tumor cells escaping detection and destruction by the immune system. Such immune escape mechanisms are mediated either directly by the tumor cells or by the tumor microenvironment. Tumor cells are known to express membrane proteins, secreted products, enzymes, anti-inflammatory cytokines, and chemokines to produce changes in their genome that aid in immune evasion and immune inhibition. At the same time, a key role is played by the tumor microenvironment.

Immune checkpoint molecules such as PD-1, PD-L1, CTLA-4 are cell surface signaling receptor play an important role in modulating the T-cell response in the tumor microenvironment. Tumor cells have been shown to utilize these checkpoints to their benefit by up regulating their expression and activity. Therefore, immune checkpoint inhibitors have been developed which can unleash the immune system's cancer-destroying properties. Recent discoveries have identified immune checkpoints or targets like, PD-1, PD-L1, PD-L2, CTLA4, TIM3, LAG3, CCR4, OX40, OX40L, IDO, and A2AR as proteins responsible for immune evasion, acting as brakes of the immune system. Specific immune checkpoint inhibitors, including antibodies against CTLA-4, PD-1 receptor or its ligand PD-L1 have produced impressive results in the clinic in a range of cancers, leading to FDA approvals for YERVOY® (Ipilimumab; CTLA-4 antagonist), OPDIVO® (Nivolumab; PD-1 antagonist) and KEYTRUDA® (Pembrolizumab; PD-1 antagonist) in multiple tumor indications and with ongoing registration trials in many more. As immune checkpoint inhibitors, could show activity in many or most tumor types, it is estimated that the market for this type of therapy could grow to >$100 billion by 2020.

Unfortunately, checkpoint inhibitors suffer from several limitations. Only a minority of patients treated with checkpoint inhibitors exhibit robust anti-tumor responses, and most responses are partial and temporary. Many patients initially respond, but then relapse due to the emergence of resistant pathways, which may occur due to many reasons, mainly the generation by the tumor cells that form a non-immune permissive micro-environment to overcome the action of the immune-checkpoint inhibitors; the so called "non-inflamed" tumors or either T cells have not been recruited to the tumor site or because even if present, they are not activated. In these cases, just releasing the brake is not enough to achieve the full anti-tumor potential of the immune system. Moreover, the cancer immunity cycle comprises of several steps and the current hypothesis is that combinations of various inhibitors acting at different stages in this cycle will permit to optimize immune-oncology therapies and improve efficacy to a wider population and reduce resistance.

This hypothesis has received its first validation by the recent approval of the combination of the two checkpoint inhibitors Ipilimumab and Nivolumab, which act on various sites in the cancer immunity cycle, which increased the response rate in melanoma patients from the 11% and 32% seen with the respective monotherapy to 60% with the combination. Unfortunately, this combination has the major drawback of high toxicity, as many patients experience unusual toxicities related to an excessive immune response leading to pneumonitis, hepatitis, colitis and other immune related disorders. It is also not known yet whether this combination will increase response rate in other tumors beside melanoma. Therefore, current research in carcinogenesis has been directed to identifying the use of therapeutic agents acting as immunomodulators, which impact the tumor or the tumor microenvironment. Various databases, conferring the details, relating to genomic, proteomic, and bioinformatics have been used to identify such individual targets that should be synergistically targeted for a better treatment response. The inventors of the present invention utilize the target dipeptidyl peptidase (DPP) which specifically includes FAP and DPP 8/9, a dipeptidyl peptidase linked to immune-evasion.

The analysis revealed the existence of several approaches to target dipeptidyl peptidase (DPP) that specifically include FAP and DPP 8/9. Various approaches include small molecules, antibodies, engineered peptides, engineered receptors, autologous immune enhancement approach or siRNA, preferred is the small molecule approach, i.e. small molecule inhibitor such as Talabostat. This clinically validated immunomodulatory small molecule plays important role in immune evasion and regulates both innate and/or acquired immunity.

Talabostat also known as PT-100 (Val-boroPro; L-valinyl-L-boroproline), was originally developed by Point Therapeutics, during 2000 to 2007. It is an orally available synthetic selective inhibitor of dipeptidyl peptidases like FAP and DPP8 and DPP9. The stereoisomer of the Talabostat molecule disclosed in the U.S. Pat. No. 6,825,169 while its oral formulation such as tablet, capsule, lozenges is disclosed in the U.S. Pat. No. 7,265,118.

U.S. Pat. No. 6,949,514 assigned to Point Therapeutics, Inc. discloses a method of treating abnormal mammalian cell proliferation by administration of Talabostat. WIPO Publication No. WO 2007058957 assigned to Point Therapeutics, Inc. discloses a combination of Talabostat with at least one cytokine such as IL-2, Interferon, G-CSF, or GM-CSF. These cytokines are not immune-checkpoint inhibitors, although they stimulate the immune system but do not remove the brakes, therefore the present invention is entirely different from this disclosure.

U.S. Pat. No. 6,890,904 assigned to Point Therapeutics, Inc. discloses a combination of Talabostat with at least one anti-cancer drug. However, these therapies of Talabostat alone or in combination with cytokine or chemotherapeutic agents are not effective for the treatment of cancer and in the clinical trials of pancreatic and lung cancer. Talabostat was unable to meet primary as well as secondary endpoints.

WIPO Publication No. WO2007059099 assigned to Point Therapeutics, Inc. discloses a combination of Talabostat with Pemetrexed or Erlotinib or Docetaxel. It further discloses that the combination therapy further comprises the administration of a cancer antigen such as B7-H1. However, WO'099 does not provide any disclosure for the combination of Talabostat with immune checkpoint inhibitors.

EP Patent No. 2,782,994 assigned to Trustees of Tufts College discloses ARI-4175 compound or other compounds that inhibit the activity of mammalian DASH serine proteases alone or in combination with immunotherapies for the treatment of cancer wherein compound is not val-boro-pro. Hence, EP'994 focuses on the use of compound ARI-4175 for treating cancer wherein Talabostat is disclaimed. However, the present invention focuses on use of Talabostat in combination with immune checkpoint inhibitors.

Talabostat shows various adverse events and the most common adverse events are edema/peripheral swelling, hypotension, hypovolemia, and dizziness. These adverse events as well as insufficient primary and secondary outcomes in the clinical trials may lead to withdrawal of Talabostat molecule.

The novel discovery in this regard includes a selective dipeptidyl peptidase (DPP) inhibitor in combination with an immune checkpoint inhibitor comprised of several elements. Firstly, the combination therapy is surprisingly more effective at sub-therapeutic doses. In addition, DPP inhibitor has been shown to induce edema, which is also a major toxicity associated with chemotherapeutic agents and therefore the combination with chemotherapeutic agent induces additive, potentially synergistic toxicity which results in discontinuation and limited efficacy. Immune checkpoint inhibitor does not have edema as relevant toxicity so this new combination approach would not have the limitation observed with the previous combination.

The final element consists of the identification of the novel combination (i.e. selective DPP inhibitor and an immune checkpoint inhibitor) that possess the strong additive/synergistic mechanism of action.

To sum up, the inventors of the present invention have come up with a combination of a selective DPP inhibitor such as Talabostat with immune checkpoint inhibitor to overcome the problems in the prior arts that may enhance or prolong the anti-tumor and immunomodulatory effects of immune checkpoint inhibitor, leading to breakdown of tumor microenvironment, enhancing infiltration and attack by immune cells, converting non-immunogenic tumor to immunogenic tumor, enabling a subject to respond to a non-responsive cancer or reducing the dose or toxicity of Talabostat and/or immune checkpoint inhibitor.

Accordingly, it is an object of the present invention to provide improved methods with a novel combination for the treatment of cancer.

SUMMARY OF THE INVENTION

The present inventors surprisingly found that there is strong additive/synergistic mechanism of action that justifies the combination of a selective dipeptidyl peptidase inhibitor and an immune checkpoint inhibitor. Selective dipeptidyl peptidase inhibitors particularly FAP (fibroblast activation protein) and DPP8/9 inhibitors cause up-regulation of chemokines which lead to migration of the effector cells of both innate and acquired immunity into a tumor. Selective dipeptidyl peptidase inhibitors show synergistic anti-tumor effects with the immune checkpoint inhibitors. In some aspects, the inhibitors can stimulate the generation of immune cells capable of recognizing the tumor cells and then it stimulating the migration of these immune cells into the tumor. In some aspects, immune checkpoint inhibitors like PD-1 antagonists act by removing the brake that tumor cells create against the immune system.

In some aspects, the combination of the PD-1 antagonists and the selective dipeptidyl peptidase inhibitors e.g., Talabostat, synergistically increases infiltration of tumoricidal NK cells into the tumors and increases the levels of the macrophages in the blood. In some aspects, the increased levels of the macrophages can further increase the amounts and the profiles of the proinflammatory cytokines, and thereby can stimulate immune responses. In some aspects, the synergistic increases of the macrophages and the NK cells in the tumor milieu can decrease the tumor volumes.

In some aspects, the combination therapies as described herein can increase the levels of perforin and the levels of granzyme B in the tumors. In some aspects, the increases of perforin and granzyme B can activate the tumoricidal NK cells and can increase the activities of the cytotoxic CD8+ T cells. The combination therapies as described herein (e.g., PD-1 antagonists+the selective dipeptidyl peptidase inhibitors such as Talabostat) can activate responses from both innate (e.g NK cells) and adaptive (e.g., cytotoxic CD8+ T cells) types of immune systems. In some aspects, the combination therapies as disclosed herein may also reduce infiltration of immune suppressive regulatory T cells (Treg) into the tumor. Thus, the selective dipeptidyl peptidase inhibitors (such as FAP and DPP8/9 inhibitors) can act as accelerators to stimulate the immune systems and transform non-responsive tumors with a non-permissive microenvironment into a responsive and immune permissive milieu in order to increase number and duration of responses.

In the principal aspect, the present invention provides novel utilization of existing or new therapeutic agents that selectively inhibits and targets dipeptidyl peptidase in combination with an immune checkpoint inhibitor for the treatment of tumor. The therapeutic agents include small molecules, antibodies, nanobodies, engineered peptide, engineered protein, vaccines, siRNA therapy or autologous immune enhancement approaches.

Accordingly, another aspect of the present invention pertains to methods of enhancing an immune response comprising administering to a subject an effective amount of therapeutic agent that selectively inhibits and targets dipeptidyl peptidase specifically fibroblast activation protein (FAP) or dipeptidyl peptidase 8/9 (DPP 8/9) in combination with an immune checkpoint inhibitor which would affect immune response or tumor growth via immune checkpoints or targets. Examples of such immune checkpoints or targets would include but not be limited to PD-1, PD-L1, PD-L2, CTLA4, VISTA, TIM3, LAG3, KIR, IDO, A2AR.

In yet another aspect, provided herein a method of enhancing an immune response in a subject, comprising administering an effective amount of a therapeutic agent(s) that act on tumors, cells in their microenvironment, immune cells or secreted products through the selective inhibition of the activity of dipeptidyl peptidase in combination with an immune checkpoint inhibitor to enhance the immune response in the subject, wherein the subject has been diagnosed for tumor.

In yet another aspect, provided herein wherein therapeutic agent is selected from a group comprising of small molecule, antibody, nanobody, engineered peptide, engineered protein, vaccine, siRNA therapy or autologous immune enhancement therapy, preferably small molecule. The therapeutic agent comprises a selective dipeptidyl peptidase inhibitor which includes the inhibition of fibroblast activation protein and/or dipeptidyl peptidase 8/9. Preferred therapeutic agent is a small molecule or antibody. Example of preferred small molecule is Talabostat.

In yet another aspect, provided herein a method of enhancing, increasing, promoting, expressing, modulating desirable immune response in a subject, comprising administering an effective amount of a small molecule or antibody that selectively inhibits dipeptidyl peptidase (for example, FAP or DPP 8/9) in combination with an immune checkpoint inhibitor selected from the group consisting of PD-1 antagonist, PD-L1 antagonist, PD-L2 antagonist, CTLA4 antagonist wherein the subject has been diagnosed for tumor associated with increased levels of FAP or DPP 8/9. The small molecule is preferably Talabostat. The antibody is anti-FAP-antibody.

In yet another aspect, the present invention provides a method of identification of tumors with upregulation of fibroblast activation protein or dipeptidyl peptidase 8/9 and which would benefit by inhibiting their activities and combining the treatment with an immune checkpoint inhibitor selected from the group comprising of PD-1 antagonist, PD-L1 antagonist, PD-L2 antagonist, CTLA4 antagonist in the cancer patients.

In another aspect, provided herein a method of treatment of proliferative diseases, including tumor which comprises administering to a subject in need thereof a synergistically, therapeutically effective amount of a selective dipeptidyl peptidase inhibitor in combination with an immune checkpoint inhibitor.

In some aspects, provided herein a selective dipeptidyl peptidase inhibitor for use in the treatment of a tumor ameliorated by stimulation of an immune response, wherein in said treatment an immune checkpoint inhibitor is co-administered.

In some aspects, provided herein a combination therapy for the treatment of tumor, the said combination comprises:
(i) a selective dipeptidyl peptidase inhibitor and
(ii) an immune checkpoint inhibitor In some aspects, the present invention is directed to a combination of a selective dipeptidyl peptidase inhibitor, particularly Talabostat, and a PD-1 axis antagonist in the treatment of tumor.

In some aspects, the present invention is directed to a combination of a selective dipeptidyl peptidase inhibitor, particularly Talabostat and a CTLA4 antagonist in the treatment of tumor.

In some aspects, the present invention provides a pharmaceutical composition for use in combination with an immune checkpoint inhibitor comprising PD-1 antagonist, PD-L1 antagonist, PD-L2 antagonist and CTLA4 antagonist for treating a tumor, wherein said pharmaceutical composition comprises a selective dipeptidyl peptidase inhibitor with one or more pharmaceutically acceptable carrier(s) or adjuvant(s).

In another aspect, provided herein use of a selective dipeptidyl peptidase inhibitor in combination with an immune checkpoint inhibitor in the manufacture of pharmaceutical composition for the treatment of tumor.

In another aspect, the present invention provides a method of enhancing an innate immune response in a subject having tumor comprising administering to a subject an effective amount of a selective dipeptidyl peptidase inhibitor in combination with an immune checkpoint inhibitor wherein the enhanced innate and adaptive immune response is associated with increased tumoricidal natural killer cells and macrophages as well as the activity of NK cells and CD8+ T cells.

In another aspect, the present invention provides a method of enhancing an innate immune response in a subject having tumor comprising administering to a subject an effective amount of a selective dipeptidyl peptidase inhibitor in combination with an immune checkpoint inhibitor wherein the enhanced innate immune response is associated with suppression of T-regulatory cells.

In some aspects, the present invention provides kits comprising:
(i) a first composition comprising a selective dipeptidyl peptidase inhibitor(s) and
(ii) a second composition comprising an immune checkpoint inhibitor(s).

In some aspects, the selective dipeptidyl peptidase inhibitor in the kits as described herein is Talabostat. In some aspects, the immune checkpoint inhibitor in the kits is a PD-1 axis antagonist. In some aspects, the PD-1 axis antagonists are selected from the group consisting of PD-1 antagonists, PD-L1 antagonists and PD-L2 antagonists. In some aspects, the tumors/cancers that can be treated by the present combination therapies are selected from the group consisting of pancreatic cancer, colorectal cancer, ovarian cancer, lung cancer, breast Cancer, glioblastoma, gastric cancer, astroglial, neuroectodermal tumors, head and neck cancer, triple negative breast cancer, gastroesophageal cancer, non-small cell lung cancer and the like.

In some aspects, the PD-1 antagonists can be ANA011, BGB-A317, KD033, Pembrolizumab, MCLA-134, mDX400, MEDI0680, muDX400, Nivolumab, PDR001, PF-06801591, Pidilizumab, REGN-2810, SHR 1210, STI-A1110, TSR-042, ANB011, 244C8, 388D4, TSR042 and XCE853, and the preferred one is Pembrolizumab, Nivolumab or Pidilizumab. In some aspects, the PD-L1 antagonists can be Avelumab, BMS-936559, CA-170, Durvalumab, MCLA-145, SP142, STI-A1011, STI-A1012, STI-A1010, STI-A1014, A110, KY1003 and Atezolimumab and the preferred one is Durvalumab or Atezolimumab. In some aspects, the PD-L2 antagonists can be AMP-224 and/or rHIgM12B7.

In some aspects, the immune checkpoint inhibitors in the combination therapies is administered at a dose from about 0.01 mg/kg to 30 mg/kg, preferably 0.1 mg/kg to 20 mg/kg, more preferably 1 mg/kg to 10 mg/kg. In some aspects, the Talabostat used in the methods for treating proliferative diseases is administered at a dose from about 0.001 mg/kg to 1 mg/kg, preferably 0.001 mg/kg to 0.05 mg/kg, and more preferably about 0.001 mg/kg to 0.035 mg/kg. In some aspects, the Talabostat used in the combination therapies as described herein is administered at a dose from about 0.001 mg/kg to 1 mg/kg, preferably 0.001 mg/kg to 0.05 mg/kg, and more preferably about 0.001 mg/kg to 0.035 mg/kg.

The present disclosure also provides pharmaceutical compositions that comprise effective amounts of Talabostat and effective amounts of Nivolumab.

Other features, objects, and advantages of the invention will be apparent from the description and drawings, and from the claims.

DETAILED DESCRIPTION OF THE INVENTION

Figure 1:
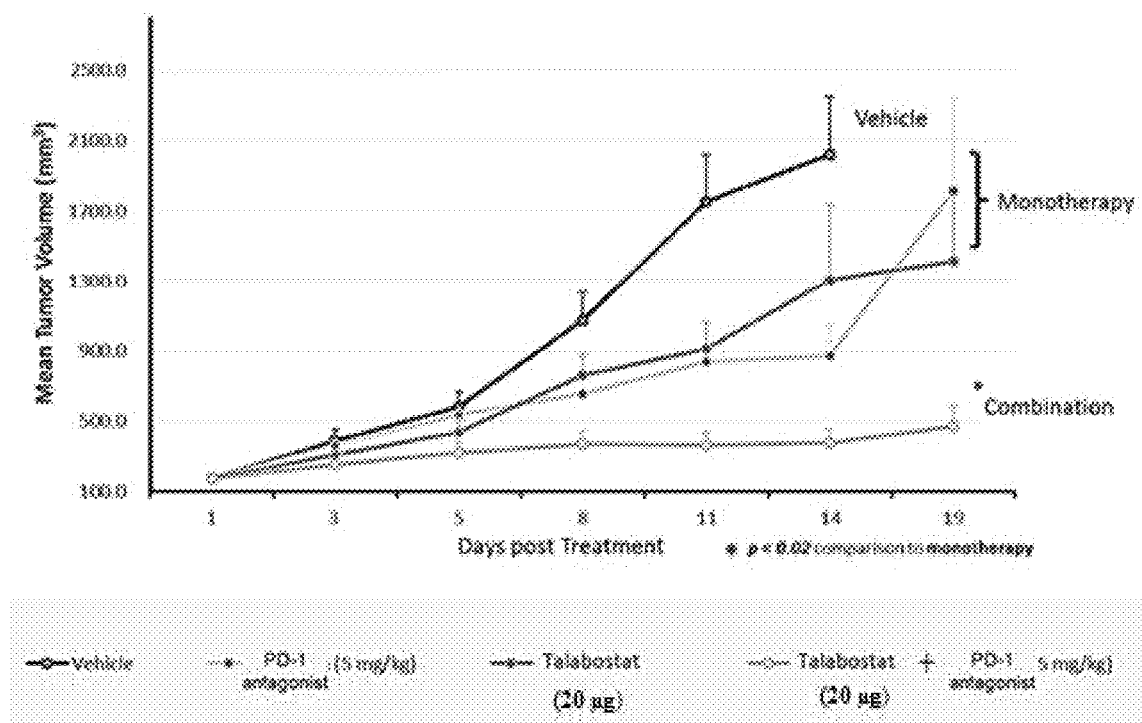
FIG. 1: shows the anti-tumor efficacy of Talabostat as a single agent as well as in combination with PD-1 antagonist 5 mg/kg (BioXcell; Cat. No. BPO146) in the MC38 mouse model of colon adenocarcinoma. The study also indicates a significant inhibition of tumor growth on day 11 post treatment.

Abbreviations:
As used herein, the following abbreviations have the following meanings:
A2AR: A2A adenosine receptor
BID: bis in die
CTLA4: Cytotoxic T-lymphocyte associated protein 4
CART: Chimeric Antigen Receptor T cell
DPP: Dipeptidyl peptidase
DMEM: Dulbecco's Modified Eagle Medium
FAP: Fibroblast activation protein
GM-CSF: Granulocyte-macrophage colony-stimulating factor
G-CSF: Granulocyte-colony stimulating factor
HBSS: Hank's Balanced Salt Solution
IL: Interleukin
IDO: Indoleamine 2,3-dioxygenase
LAG3: Lymphocyte activation gene 3 protein
PD-1: Programmed Cell Death 1
KIR: Lymphocyte activation gene 3 protein
KLH: Key hole limpet haemocyanin
NK: Natural killer
Q.D: Quaque die
TIM3: T-cell immunoglobulin and mucin-domain containing-3
VISTA: V domain-containing Ig suppressor of T-cell activation
Treg: Regulatory T cells or T-regulatory cells The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The present invention provides that immunomodulatory immune escape mechanism that could be targeted in combination with various therapeutic agents to hamper the immune escape opted by the tumor cells and its microenvironment. This would involve combination of multiple immune-modulatory approaches like increasing the access of the immune cells to the tumor by antagonizing the immune repelling mechanisms, antagonizing inhibitory immunologic pathways or by activating immune stimulatory pathways. These immunomodulatory targeting agents are clinically active in a variety of malignancies, including those not traditionally classified as immunogenic.

One of the targets is dipeptidyl peptidase which includes fibroblast activation protein (FAP), a homodimeric integral membrane protease with dipeptidyl peptidase activity and dipeptidyl peptidase (DPP 8/9), employed as one of the therapeutic approach for treating tumor in combination with a second immune-modulating approach involving targeting programmed death-ligand 1 or PD-1 or cytotoxic T-lymphocyte-associated protein 4 (CTLA4) or other immune modulating targets. Programmed death 1 (PD-1) receptor, its ligands (PD-L1/2) and CTLA4 (cytotoxic T-lymphocyte-associated protein 4) have roles in tumor-induced immune suppression and has been a critical advancement in immunotherapeutic drug development.

An advantage of combination of a selective dipeptidyl peptidase inhibitor and an immune checkpoint molecule targeted therapeutic approaches reduce the development of tumors, reduces tumor burden, or produces tumor regression in a mammalian host.

The present invention relates to a combination of a selective dipeptidyl peptidase inhibitor and an immune checkpoint inhibitor to promote an effective anti-tumor response. The details of the various features of the present invention are as follows:

Various therapeutic agents/antibodies of the present invention are described below:

I. Therapeutic Agents

A therapeutic agent that selectively targets and inhibits dipeptidyl peptidase is a selective dipeptidyl peptidase inhibitor, which includes antibody (including—anti-FAP antibody or nanobody) or small molecule (for example, Talabostat). The preferred selective dipeptidyl peptidase inhibitor is small molecule (for example, Talabostat).

a) Selective Dipeptidyl Peptidase Inhibitor

The dipeptidyl peptidase (DPP)-like gene family is a family of molecules which have related protein structure and function. The gene family includes the following molecules: DPPIV (CD26), dipeptidyl amino-peptidase-like protein 6 (DPP6), dipeptidyl amino-peptidase-like protein 8 (DPP8), dipeptidyl amino-peptidase-like protein 9 (DPP9), and fibroblast activation protein (FAP). The selective dipeptidyl peptidase inhibitor includes FAP and DPP 8/9 inhibitors specifically. With respect to oncology, the current notions for the DPPs (particularly FAP and DPP 8/9) are of importance to Talabostat mechanism of action.

Fibroblast Activation Protein (FAP) Inhibitors

Fibroblast activation protein (FAP) or seprase is a member of the serine integral membrane peptidases and belongs to the propyl oligopeptidase family. It is a propyl specific enzyme that exhibits both endopeptidase and dipeptidyl peptidase activities. FAP is a protein expressed on fibroblasts present in the tumor microenvironment. It exists as a dimer both on the cell surface and in a soluble, circulating form in the blood. It is selectively expressed in reactive stromal fibroblasts of many histological types of epithelial cancers like pancreatic, breast, lung, colorectal, glioblastoma. It is also associated with granulation tissue of healing wounds, and malignant cells of certain bone and soft tissue sarcomas. FAP through its peptidase activity was shown to be responsible for degrading the extra cellular matrix around the tumor and facilitate the metastatic process. It has also been shown to increase angiogenesis thus leading to tumor growth. At the same time, FAP expressing fibroblasts can produce chemokines and cytokines that reduce immune invasion of the tumor. Hence, FAP inhibitors or antibodies have been developed to attenuate the tumor growth.

FAP inhibitors available in the market as Talabostat (PT-100, Val-boro-pro) and Sibrotuzumab.

Talabostat is referred to interchangeably as PT-100, Talabostat (USAN), and [(2R)-1-I [(2S)-2-amino-3-methyl-1-oxobutyl]-2-pyrrolidinyl] boronic acid. Talabostat has a CAS registration number of 149682-77-9. In some aspects, the free base may be used. In other aspects, the Talabostat may be a solvate. In yet other aspects, a Talabostat derivative may be used. In most clinical formulations, Talabostat is provided as a salt form. Preferably, the salt form is made by combining Talabostat as a free base with methane sulphonate salt. The salt form may be Talabostat mesylate. Accordingly, as used herein, "Talabostat" includes Talabostat mesylate. The API is a single enantiomer having an R, S configuration. Talabostat can exist as both linear and cyclic forms.

Talabostat is effective for the treatment of cancer or tumor by modulating multiple intracellular and extracellular dipeptidyl peptidases. More specifically, intracellular and extracellular dipeptidyl peptidases comprise of Fibroblast Activation Protein, DPP 8/9, CD26/DPP4 and DPP2. Talabostat has a dual mechanism of action which includes stromal targeted activity via FAP inhibition and targeted immunostimulatory activity via DPP 8/9 inhibition. Talabostat inhibits FAP enzymatic activity thereby suppressing tumor growth. Also, inhibits DPP8/9 thereby induces an IL 1β response (via caspase-1) in the stroma of tumor and lymph nodes. Talabostat dual mechanism of action introduces a novel approach to the treatment of cancer because it combines both tumor-targeted and immunostimulatory activity in a single agent.

Sibrotuzumab as disclosed in U.S. Pat. No. 6,455,677 assigned to Boehringer Ingelheim International Gmbh and it discloses a monoclonal antibody that binds to FAP-α.

Other FAP inhibitors include but not limited to such as ARI-3099 (N-(pyridine-4-carbonyl)-d-Ala-boroPro) as disclosed in Sarah E. Poplawski et al., 2013, Vol. 56(9), Page no. 3467-3477; ARI-3996 as disclosed in U.S. Patent Application No. 20140255300; MIP-1231 (MIP-1232 or MIP-1233) as disclosed in U.S. Patent Application No. 20100098633; (4-quinolinoyl)-glycyl-2-cyanopyyrolidines as disclosed by Koen Jansen et al., 2013, Vol. 4 (5), Page no. 491-496; (2S)-1-(2-(1-Napthoylamino)acetyl)pyrroline-2-carbonitrile as disclosed in U.S. Pat. No. 8,183,280; (S)-A-(2-(2-cyano-4,4-difluoropyrrolidin-1-yl)-2-oxoethyl)-1-naphthamide and other related derivatives as disclosed in PCT Application No. 2013107820; (2S)-1-((2S)-2-(2-Methoxybenzoylamino)-3-methylpentanoyl) pyrrolidine-2-carbonitrile and other related derivatives as disclosed in U.S. Patent Application No. 20120053222; Ac-Gly-BoroPro as disclosed by Conrad Yap Edosada et al. 2006, Vo. 281(11) Page no. 7437-7444; Substituted 4-carboxylmethyl pyroglutamic acid diamides as disclosed in Ting-yueh Tsai et al., 2010, Vol. 53(18), 6572-6583; GEH200200 as disclose by P. Iveson et al., 2014, Vol. 41(7), 620; UAMC-1110 as disclosed in U.S. Pat. No. 9,346,814; some FAP inhibitors also disclosed in PCT application no. 2002038590, U.S. Pat. Nos. 7,399,869; 7,998,997.

Other patents that disclose the FAP-α antibody such as U.S. Pat. No. 8,568,727 (assigned to Boehringer Ingelheim. International Gmbh), E.P. Patent No. 1,268,550 (assigned to Boehringer Ingelheim. International Gmbh), U.S. Pat. No. 8,999,342 (assigned to Ludwig Institute for Cancer Research Ltd), U.S. Pat. No. 9,011,847 (assigned to Roche Glycart). Bispecific antibodies of FAP with DR-5 are disclosed in U.S. Patent Application No. 20140370019 and 20120184718; Chimeric antigen receptor and FAP combination is disclosed in U.S. Patent Application No. 20140099340.

F11-24 antibody is a mouse monoclonal antibody targeting against FAP. Anti-FAP-α antibody include antibodies which are raised in mouse against epitope of Key hole limpet haemocyanin (KLH) conjugated synthetic peptide between 15-41 amino acids from the N-terminal region; Leu26-Asp760 amino acid; and 525-625 amino acid.

(PPQFDRSKKYPLLIQVYGGPCSQSVRSVFAVNWISYLASKEGMVIALV

DGRGTAFQGDKLLYAVYRKLGVYEVEDQITAVRKFIEMGFIDEKRIAIW

GWS-(SEQ ID NO: 1)).

Similarly, anti-FAP antibody include antibodies which are raised in rabbit against the epitope of N-terminus of human fibroblast activation protein, alpha of 57-73 amino acid with sequence FFPNWISGQEYLHQSAD (SEQ ID NO: 2); 26-280 amino acid; 95-337 amino acid; 300-380 amino acid; 331-380 amino acids from the Internal region of human FAP-1; 350-400 amino acid; kLH-conjugated synthetic peptide of 396-426 amino acid, Lys366 amino acid; Ile523-Asp760 amino acid of human seprase expressed in E. coli; 525-625 amino acid; 544-599 amino acid; Gly542-Asp761 amino acid; 652-701 amino acid; C-terminal region of Human FAP of immunogen sequence (SEQ ID NO: 3)
SWEYYASVYTERFMGLPTKDDNLEHYKNSTVMARAEYFRNVDYLLIHGTA;

(SEQ ID NO: 4)
ERCQYYTASFSDYAKYYALVCYGPGIPISTLHDGRTDQEIKILEENKELENALKNIQLPK EEIKKLEVDE ITLWYKM.

In other aspects, the anti-FAP antibody may be a nanobody. Nanobody technology was developed from the discovery that antibodies from camels and llamas (Camelidae, camelids) have heavy chains but no light chains. The antigen-binding site of such antibodies is one single domain, and may be referred to as VHH. See, e.g., U.S. Pat. Nos. 5,800,988 and 6,005,079 and International Application Publication Nos. WO 94/04678, WO 94/25591 and EP 2673297 which are incorporated by reference.

TABLE 1

| Immunogen Sequence | Sequence ID | Vendor |
|---|---|---|
| PPQFDRSKKYPLLIQVYGGPCSQS VRSVFAVNWISYLASKEGMVIALV DGRGTAFQGDKLLYAVYRKLGVYE VEDQITAVRKFIEMGFIDEKRIAI WGWS | SEQ ID NO: 1 | signaaldrich.com/catalog/ product/sigma/sab1403805 antibodypedia.com/gene/ 33750/FAP/antibody/585989/ H00002101-M02 |
| FFPNWISGQEYLHQSAD | SEQ ID NO: 2 | bosterbio.com/anti-fibroblast- activation-protein-alpha-antibody- pa1913 |
| SWEYYASVYTERFMGLPTKDDNLE HYKNSTVMARAEYFRNVDYLLIHG TA | SEQ ID NO: 3 | avivasysbio.com/fab-antibody-c- terminal-region-arp46455-p050 |
| ERCQYYTASFSDYAKYYALVCYGP GIPISTLHDGRTDQEIKILEENKE LENALKNIQLPKEEIKKLEVDE I TLWYKM | SEQ ID NO: 4 | atlasantibodies.com/#!/products/ FAP-antibody-HPA059739 |

Dipeptidyl Peptidase 8/9

DPP8 and DPP9 have been discovered as two members of the propyl oligopetidase S9b subfamily, which also contains DPPIV and FAP. It is characterized by the rare ability to cleave a post-proline bond two residues from the N-terminus of a substrate. DPP8 and DPP9 have unique cellular localization patterns, are ubiquitously expressed in tissues and cell lines, and important contributions to various biological processes including: cell behavior, cancer biology, disease pathogenesis, and immune responses.

Inhibition of Dipeptidyl peptidase (DPP 8/9) and DPP 8/9 results in IL-1β induction (via Caspase-1 activation) in the stroma of tumor and lymph nodes results in the production of cytokines and chemokines which employed as one of the therapeutic approach for treating cancer in combination with a second immune-modulating approach.

DPP8 gene is localized to human chromosome 15q22, codes for protein of 882 amino acids. It is localized to the cytoplasm and has a molecular weight of 100 kDa.

DPP8/9 specific inhibitors are (2S,3R)-2-amino-1-(isoindolin-2-yl)-3-methylpentan-1-one (allo-Ile-isoindoline (UAMC00132); (S)-2,6-diamino-1-(isoindolin-2-yl)hexan-1-one (Lys-isoindoline (UAMC00071); 1G244 (PTX-1210; (S)-2-Amino-4-{4-[bis-(4-fluorophenyl)-methyl]piperazin-1-yl}-1-(1,3-dihydro-isoindol-2-yl)-butane-1,4-dione); PTX-1200 (cyclohexyl glycine-isoindoline); (2S)-2-Amino-4-(4-((4-chlorophenyl)(phenyl)methyl)piperazin-1-yl)-1-(5-fluoroisoindolin-2-yl)butane-1,4-dione bis-(2,2,2-trifluoro-acetate); (2S)-2-Amino-4-(4-((4-chlorophenyl)(phenyl) methyl)piperazin-1-yl)-1-(isoindolin-2-yl)butane-1,4-dione bis(2,2,2-tri-fluoroacetate); (S)-2-Amino-4-((S)-4-(bis(4-fluorophenyl)methyl)-3-methyl-piperazin-1-yl)-1-(isoindolin-2-yl)butane-1,4-dione Bis(2,2,2-tri-fluoroacetate); (2S)-2-Amino-4-((3R)-4-((3-fluorophenyl)(4-fluorophenyl)-methyl)-3-methylpiperazin-1-yl)-1-(isoindolin-2-yl)butane-1,4-dione Bis(2,2,2-trifluoroacetate, SUMO1 EIL Peptide (as disclosed in U.S. Patent Application No. 20150266922).

Immune Checkpoint Inhibitors

Immune checkpoint inhibitor includes PD1 antagonist, PD-L1 antagonist, PD-L2 antagonist CTLA4 antagonist, VISTA antagonist, TIM3 antagonist, LAG3 antagonist, IDO antagonist, KIR2D antagonist, A2AR antagonist, B7-H3 antagonist, B7-H4 antagonist, BTLA antagonist and the preferred one is PD-1 axis antagonist, CTLA4 antagonist or combination thereof.

PD-1 Axis Antagonists

PD1 axis antagonists include PD1 antagonist (for example anti-PD-1 antibody), PD-L1 antagonist (for example anti-PD-L1 antibody) and PD-L2 antagonist (for example anti-PD-L2 antibody).

As used herein, the terms "Programmed Death 1," "Programmed Cell Death 1," "Protein PD-1," "PD-1," "PD1," "PDCD1," "hPD-1" and "hPD-I" are used interchangeably, and include variants, isoforms, species homologs of human PD-1, and analogs having at least one common epitope with human PD-1. The complete human PD-1 sequence can be found under GenBank Accession No. U64863. In particular aspects, the PD-1 antagonist binds the PD-1 protein of SEQ ID NO: 5 (uniprot ID Q15116).

As used herein, the terms "Programmed Cell Death 1 Ligand 1", "PD-L1", "PDL1", "PDCD1L1", "PDCD1LG1", "CD274", "B7 homolog 1", "B7-H1", "B7-H", and "B7H1" are used interchangeably, and include variants, isoforms, species homologs of human PDL-1, and analogues having at least one common epitope with human PDL-1.

The protein programmed death 1 (PD-1) is an inhibitory member of the CD28 family of receptors, that also includes CD28, CTLA-4, ICOS and BTLA.

Two ligands for PD-1 have been identified, PD-L1 and PD-L2, that have been shown to downregulate T cell activation upon binding to PD-1 (Freeman et al. (2000) J Exp. Med. 192: 1027-34; Latchman et al. (2001) Nat Immunol. 2:261-8; Carter et al. (2002) Eur. J Immunol 32:634-43). Both PD-L1 and PD-L2 are B7 homologs that bind to PD-1, but do not bind to other CD28 family members. PD-L1 is abundant in a variety of human cancers (Dong et al. (2002) Nat. Med. 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) J. Mol. Med. 81:281-7; Blank et al. (2005) Cancer Immunol. Immunother. 54:307-314; Kenosha et al. (2004) Clin. Cancer Res. 10:5094-100). Immune suppression can be reversed by inhibiting the local interaction of PD-1 with PD-L1, and the effect is additive when the interaction of PD-1 with PD-L2 is blocked as well (Iwai et al. (2002) Proc. Nat'l. Acad. Sci. USA 99:12293-7; Brown et al. (2003) J. Immunol. 170: 1257-66).

The methods of the present invention involve the use of a PD-1 antagonist (e.g., an antibody) in combination with selective dipeptidyl peptidase inhibitor for treating tumor or cancer. Accordingly, PD-1 antagonists of the invention bind to ligands of PD-1 and interfere with, reduce, or inhibit the binding of one or more ligands to the PD-1 receptor, or bind directly to the PD-1 receptor, without engaging in signal transduction through the PD-1 receptor. In one embodiment, the PD-1 antagonist binds directly to PD-1 and blocks PD-1 inhibitory signal transduction. In another embodiment, the PD-1 antagonist binds to one or more ligands of PD-1 (e.g., PD-L1 and PD-L2) and reduces or inhibits the ligand(s) from triggering inhibitory signal transduction through the PD-1. In one embodiment, the PD-1 antagonist binds directly to PD-L1, inhibiting or preventing PD-L1 from binding to PD-1, thereby blocking PD-1 inhibitory signal transduction.

PD-1 antagonists used in the methods and compositions of the present invention include PD-1 binding scaffold proteins and include, but are not limited to, PD-1 ligands, antibodies and multivalent agents. In a particular embodiment, the antagonist is a fusion protein, such as AMP-224. In another embodiment, the antagonist is an anti-PD-1 antibody ("PD-1 antibody"). Anti-human-PD-1 antibodies (or VH and/or VL domains derived therefrom) suitable for use in the invention can be generated using methods well known in the art.

In some embodiment, the antibodies interfering with PD-1 is an anti-PD-1 antibody or PD-1 antagonist (e.g., a human antibody, a humanized antibody, or a chimeric antibody). In some embodiments, the anti-PD-1 antibody is selected from the group consisting of MDX-1106 (also known as Nivolumab, MDX-1106-04, ONO-4538, BMS-936558, and OPDIVO®), Merck 3475 (also known as Pembrolizumab, MK-3475, Lambrolizumab, KEYTRUDA®, and SCH-900475), and CT-011 (also known as Pidilizumab, hBAT, and hBAT-1). In some embodiments, the PD-1 binding antagonist is AMP-224 (also known as B7-DCIg). In some embodiments, the anti-PD-L1 antibody is selected from the group consisting of YW243.55.S70, MPDL3280A, MDX-1105, and MEDI4736. MDX-1105, also known as BMS-936559, is an anti-PD-L1 antibody described in WO2007/005874. Antibody W243.55. S70 is an anti-PD-L1 described in WO 2010/077634 A1. MEDI4736 is an anti-PD-L1 antibody described in WO2011/066389 and US2013/034559. MDX-1106, also known as MDX-1106-04, ONO-4538 or BMS-936558, is an anti-PD-1 antibody described in U.S. Pat. No. 8,008,449 and WO2006/121168. Merck 3745, also known as MK-3475 or SCH-900475, is an anti-PD-1 antibody described in U.S. Pat. No. 8,345,509 and WO2009/114335. CT-011 (Pidizilumab), also known as hBAT or hBAT-1, is an anti-PD-1 antibody described in WO2009/101611. AMP-224, also known as B7-DCIg, is a PD-L2-Fc fusion soluble receptor described in WO2010/027827 and WO2011/066342. Atezolimumab is an anti-PD-L1 antibody described in U.S. Pat. No. 8,217,149. Avelumab is an anti-PD-L1 antibody described in US 20140341917. CA-170 is a PD-1 antagonist described in WO2015033301 & WO2015033299. Other anti-PD1 antibodies are disclosed in U.S. Pat. No. 8,609,089, US 2010028330, and/or US 20120114649.

In some embodiments, the anti-PD-1 antibody is MDX-1106. Alternative names for "MDX-1106" include MDX-1106-04, ONO-4538, BMS-936558 or Nivolumab. In some embodiments, the anti-PD-1 antibody is Nivolumab (CAS Registry Number: 946414-94-4).

In some embodiments, the anti PD-L2 antibody is AMP-224 or rHIgM12B7.

In one embodiment, the PD-1 inhibitor is an anti-PD-1 antibody chosen from Nivolumab, Pembrolizumab or Pidilizumab.

Examples of anti-PD-L1 antibodies useful for the methods of this invention, and methods for making thereof are described in WIPO patent publication WO 2010/077634, which is incorporated herein by reference.

The anti-PD-L1 antibodies or PD-L1 antagonist useful in this invention, including compositions containing such antibodies, such as those described in WO 2010/077634 and U.S. Pat. No. 8,217,149, may be used in combination with a selective dipeptidyl peptidase inhibitor to treat cancer.

The antibody or antigen binding fragment thereof, may be made using methods known in the art, for example, by a process comprising culturing a host cell containing nucleic acid encoding any of the previously described anti-PD-L1, anti-PD-1, or anti-PD-L2 antibodies or antigen-binding fragment in a form suitable for expression, under conditions suitable to produce such antibody or fragment, and recovering the antibody or fragment.

With regard to anti-PD-1 antibodies or PD-1 antagonist, these are known and include Nivolumab and Lambrolizumab, AMP-224, MDPL3280A, MEDI4736 and MSB0010718C. Anti-PD-1 antibody may be procured from BPS Biosciences and Bio X cell.

In one embodiment, PD-1 antagonist is selected from the group comprising of ANA011, AUNP-12, BGB-A317, KD033, Pembrolizumab, MCLA-134, mDX400, MEDI0680, muDX400, Nivolumab, PDR001, PF-06801591, Pidilizumab, REGN-2810, SHR-1210, STI-A1110, TSR-042, ANB011, 244C8, 388D4, TSR042 and XCE853 and the preferred one is Pembrolizumab or Nivolumab or Pidilizumab.

In one embodiment, PD-L1 antagonist is selected from the group comprising of Avelumab, BMS-936559, CA-170, Durvalumab, MCLA-145, SP142, STI-A1011, STIA1012, STI-A1010, STI-A1014, A110, KY1003 and Atezolimumab and the preferred one is Avelumab, Durvalumab or Atezolimumab.

In one embodiment, PD-L2 antagonist is selected from the group comprising of AMP-224 or rHIgM12B7.

CTLA4 Antagonists

Suitable anti-CTLA4 antagonist for use in the methods of the invention, include, without limitation, anti-CTLA4 antibodies, human anti-CTLA4 antibodies, mouse anti-CTLA4 antibodies, mammalian anti-CTLA4 antibodies, humanized anti-CTLA4 antibodies, monoclonal anti-CTLA4 antibodies, polyclonal anti-CTLA4 antibodies, chimeric anti-CTLA4 antibodies, MDX-010 (Ipilimumab), Tremelimumab, anti-CD28 antibodies, anti-CTLA4 adnectins, anti-CTLA4 domain antibodies, single chain anti-CTLA4 fragments, heavy chain anti-CTLA4 fragments, light chain anti-CTLA4 fragments, inhibitors of CTLA4 that agonize the co-stimulatory pathway, the antibodies disclosed in PCT Publication No. WO 2001/014424, the antibodies disclosed in PCT Publication No. WO 2004/035607, the antibodies disclosed in U.S. Publication No. 2005/0201994, and the antibodies disclosed in granted European Patent No. EP 1212422 B. Additional CTLA-4 antibodies are described in U.S. Pat. Nos. 5,811,097; 5,855,887; 6,051,227; and 6,984,720; in PCT Publication Nos. WO 01/14424 and WO 00/37504; and in U.S. Publication Nos. 2002/0039581 and 2002/086014. Other anti-CTLA-4 antibodies that can be used in a method of the present invention include, for example, those disclosed in: WO 98/42752; U.S. Pat. Nos. 6,682,736 and 6,207,156; Hurwitz et al., Proc. Natl. Acad. Sci. USA, 95(17): 10067-10071 (1998); Camacho et al., J. Clin: Oncology, 22(145): Abstract No. 2505 (2004) (antibody CP-675206); Mokyr et al., Cancer Res., 58:5301-5304 (1998), and U.S. Pat. Nos. 5,977,318, 6,682,736, 7,109,003, and 7,132,281.

A preferred clinical CTLA-4 antibody is human monoclonal antibody (also referred to as MDX-010 and Ipilimumab with CAS No. 477202-00-9 and available from Medarex, Inc., Bloomsbury, N.J.) is disclosed in WO 01/14424.

With regard to CTLA-4 antagonist (antibodies), these are known and include Tremelimumab (CP-675,206) and Ipilimumab.

CTLA4 antagonist is selected from group comprising of KAHR-102, AGEN1884, ABR002, KN044, Tremelimumab or Ipilimumab and the preferred one is Tremelimumab or Ipilimumab.

II. Method of Uses

The present invention is based, in part, on the surprising finding that concurrent administration of a selective dipeptidyl peptidase inhibitor such as Talabostat and an immune checkpoint inhibitor such as PD-1 antagonist, PDL-1 antagonist, CTLA4 antagonist resulted in significantly higher anti-tumor efficacy compared to either alone. This finding was unexpected because this combination produces overall enhanced anti-cancer effect such as improved T-cell priming, increased T cell stimulation, increased infiltration of neutrophil and macrophages across tumor microenvironment, decreased tumor volume, increased activation of natural killer cells, enhanced activation of dendritic cells, synergistic increase in proinflammatory cytokine (IL2, IL6, IL12p40, IL 15, IL 7, G-CSF and GM-CSF), enhanced anti-tumor memory response and reduced toxicity.

In one embodiment, the present invention provides a novel combination approach comprising:
(i) an effective amount of a selective dipeptidyl peptidase inhibitor and
(ii) an effective amount of an immune checkpoint inhibitor In an embodiment, the present invention provides the use of inhibitor of fibroblast protein activation (FAP) or dipeptidyl peptidase 8/9 (DPP8/9) activity as well as pharmaceutical compositions in combination with an immune checkpoint inhibitor for the prevention and/or treatment of tumor or cancer.

In one embodiment, provided herein is a method for treating, delaying progression or preventing or delaying tumor recurrence, tumor growth or tumor spread of tumor in a subject having tumor comprising administering to the subject an effective amount of a selective dipeptidyl peptidase inhibitor (for example, Talabostat) and an immune checkpoint inhibitor (for example PD-1 axis binding antagonist).

In one embodiment, provided herein is a method for treating, delaying progression or preventing or delaying tumor recurrence, tumor growth or tumor spread of tumor in a subject having tumor comprising administering to the subject an effective amount of a selective dipeptidyl peptidase inhibitor (for example, Talabostat) and one or more immune checkpoint inhibitors (for example combination of PD-1 axis binding antagonist).

In one embodiment, provided herein is a method of enhancing immune function in a subject having cancer comprising administering to the subject an effective amount of a selective dipeptidyl peptidase inhibitor (for example, Talabostat) and an immune checkpoint inhibitor (for example PD-1 axis binding antagonist).

In another embodiment, the present invention provides for a method for initiating, sustaining or enhancing an anti-tumor immune response, the method comprising administering to a subject:
(i) an effective amount of a selective dipeptidyl peptidase inhibitor and
(ii) an effective amount of an immune checkpoint inhibitor.

In another embodiment, the present invention provides for a method for initiating, sustaining or enhancing an anti-tumor immune response, the method comprising administering to a subject (a) Talabostat and (b) PD-1 axis binding antagonist.

Moreover, the administration of (a) a selective dipeptidyl peptidase inhibitor and (b) an immune checkpoint inhibitor described herein may reduce an effective amount of checkpoint inhibitor to be administered to a subject or patient. Further, the reduced amount of the checkpoint inhibitor may reduce the toxicity of the checkpoint inhibitor and increase the subject's tolerance to the checkpoint inhibitor.

The cancers described below can be treated with a selective dipeptidyl peptidase inhibitor and a PD-1 axis binding antagonist includes the treatment of FAP expressing cancer. In some embodiments, the individual treated is suffering from a FAP expressing cancer.

In some embodiments, the subject has cancer or is at risk of developing cancer. In some embodiments, the treatment results in a sustained response in the individual after cessation of the treatment. In some embodiments, the individual has cancer that may be at early stage or late stage. In some embodiments, the cancer is metastatic. In some embodiments, the individual is a human.

In one embodiment, the present invention provides a pharmaceutical composition comprising:
(i) an effective amount of a selective dipeptidyl peptidase inhibitor;
(ii) an effective amount of an immune checkpoint inhibitor; and
(iii) a pharmaceutically acceptable excipient(s) or carrier(s)

wherein administering the composition to a subject having a tumor treats, prevents or delays tumor growth or metastasis in the subject.

In another embodiment, the present invention discloses a pharmaceutical composition comprising one or more selective dipeptidyl peptidase inhibitor(s) in combination with one or more immune checkpoint inhibitor(s), along with an optional anti-tumor agent(s) and one or more pharmaceutically acceptable carrier(s) and/or adjuvants.

In another embodiment, the present invention provides a pharmaceutical composition comprising:
  (i) an effective amount of a selective dipeptidyl peptidase inhibitor (s);
  (ii) an effective amount of a PD-1 axis antagonist(s),
  (iii) one or more pharmaceutically acceptable carrier(s) or adjuvant(s),
wherein administering the composition to a subject having a tumor treats, prevents or delays tumor growth or metastasis in the subject.

In yet another embodiment, the present invention provides a pharmaceutical composition comprising a selective dipeptidyl peptidase inhibitor in combination with PD-1 antagonist along with an optional anti-tumor agent(s) and one or more pharmaceutically acceptable carrier(s) or adjuvant(s).

In another embodiment, the present invention provides a pharmaceutical composition comprising a selective dipeptidyl peptidase inhibitor in combination with PD-L1 antagonist along with an optional anti-tumor agent(s) and one or more pharmaceutically acceptable carrier(s) or adjuvant(s).

In another embodiment, the present invention provides a pharmaceutical composition comprising a selective dipeptidyl peptidase inhibitor in combination with PD-L2 antagonist along with an optional anti-tumor agent(s) and one or more pharmaceutically acceptable carrier(s) or adjuvant(s).

In another embodiment, the present invention provides a pharmaceutical composition comprising:
  (i) an effective amount of a selective dipeptidyl peptidase inhibitor(s);
  (ii) an effective amount of a CTLA4 antagonist(s) and
  (iii) one or more pharmaceutically acceptable carrier(s) or adjuvant(s)
wherein administering the composition to a subject having a tumor treats, prevents or delays tumor growth or metastasis in the subject.

In another embodiment, the present invention provides a pharmaceutical composition comprising:
  (i) an effective amount of a selective dipeptidyl peptidase inhibitor(s);
  (ii) an effective amount of a PD-1 axis antagonist(s);
  (iii) an effective amount of a CTLA4 antagonist(s) and
  (iv) one or more pharmaceutically acceptable carrier(s) or adjuvant(s)
wherein administering the composition to a subject having a tumor treats, prevents or delays tumor growth or metastasis in the subject.

In some embodiments, the pharmaceutical composition can comprise an effective amount of Talabostat. In some embodiments, the pharmaceutical composition can comprise an effective amount of Nivolumab.

In yet another embodiment, the present invention provides a pharmaceutical composition comprising a selective dipeptidyl peptidase inhibitor in combination with CTLA4 antagonist along with an optional anti-tumor agent(s) and one or more pharmaceutically acceptable carrier(s) or adjuvant(s).

The anti-tumor agent may be selected from the group consisting of an antibody, or a small molecule. Examples of anti-tumor agents include but not limited: low dose Cyclophosphamide, Trastuzumab, Bevacizumab, Cetuximab, Panitumumab, Sunitinib, Sorafenib, Gefitinib, Erlotinib, Temsirolimus, Adotrastuzumab, Emtansine, Crizotinib, Pertuzumab, Ramucirumab, Regorafenib, Vemurafenib, Abiraterone acetate, Ziv-aflibercept and the like. Alternatively, or in combination with the aforesaid combinations, the methods and compositions described herein can be administered in combination with one or more vaccine, e.g., a therapeutic cancer vaccine; or other forms of cellular immunotherapy.

In another embodiment, the present invention discloses a method of enhancing, increasing, promoting, modulating desirable immune response in a subject comprising administering to a subject a first composition comprising an effective amount of a selective dipeptidyl peptidase inhibitor and a second composition comprising an effective amount of an immune checkpoint inhibitor, wherein said subject is diagnosed with tumor or cancer associated with increased levels of FAP or DPP 8/9 and/or an immune checkpoint molecule(s).

In another embodiment, provided herein is use of a selective dipeptidyl peptidase inhibitor (for example Talabostat) in the manufacture of a first pharmaceutical composition for treating, preventing or delaying progression of tumor in a subject, wherein the first pharmaceutical composition comprises the selective dipeptidyl peptidase inhibitor (for example Talabostat) and one or more pharmaceutically acceptable carrier(s), and wherein the treatment comprises administration of the first pharmaceutical composition in combination with a second pharmaceutical composition comprising an immune checkpoint inhibitor and one or more pharmaceutically acceptable carrier(s).

In another embodiment, provided herein is a first pharmaceutical composition comprising a selective dipeptidyl peptidase inhibitor (for example Talabostat) and one or more pharmaceutically acceptable carrier(s) for use in treating or delaying progression of tumor in a subject, wherein the treatment comprises administration of said first pharmaceutical composition in combination with a second composition, wherein the second composition comprises an immune checkpoint inhibitor and one or more pharmaceutically acceptable carrier(s).

In another embodiment, provided herein is a second pharmaceutical composition comprising an immune checkpoint inhibitor and one or more pharmaceutically acceptable carrier(s) for use in treating or delaying progression of tumor in a subject, wherein the treatment comprises administration of said second pharmaceutical composition in combination with a first composition, wherein the first composition comprises a selective dipeptidyl peptidase inhibitor (for example Talabostat) and one or more pharmaceutically acceptable carrier(s).

In another embodiment, provided herein is use of a selective dipeptidyl peptidase inhibitor (for example Talabostat) in the manufacture of a first pharmaceutical composition for enhancing immune function in a subject having cancer or tumor, wherein the first pharmaceutical composition comprises the selective dipeptidyl peptidase inhibitor (for example Talabostat) and one or more pharmaceutically acceptable carrier(s), and wherein treatment comprises administration of the pharmaceutical composition in combination with a second composition comprising an immune checkpoint inhibitor and one or more pharmaceutically acceptable carrier(s).

In another embodiment, provided herein is use of an immune checkpoint inhibitor in the manufacture of a second pharmaceutical composition for enhancing immune function in a subject having cancer, wherein the second pharmaceutical composition comprises the immune checkpoint inhibitor and one or more pharmaceutically acceptable carrier(s), and wherein the treatment comprises administration of the second pharmaceutical composition in combination with a first composition comprising a selective dipeptidyl peptidase inhibitor (for example Talabostat) and one or more pharmaceutically acceptable carrier(s).

In another embodiment, the present invention provides a method for reducing the toxicity of a selective DPP inhibitor or enabling therapeutic effects to be obtained with a lower dose of a selective DPP inhibitor, the method comprising administering to a subject a selective DPP inhibitor and a checkpoint inhibitor described herein.

In an additional embodiment, the present invention provides a method for inducing an immune response prior to administration of a checkpoint inhibitor, the method comprising initiating or enabling an anti-tumor immune response or enhancing a pre-existing anti-tumor immune response using selective DPP inhibitor, followed by administration of one or more checkpoint inhibitors described herein.

In another embodiment, the present invention provides a rationale to combine a selective dipeptidyl peptidase inhibitor and CAR-T or CAR-NK cells. The inventors of the present invention revealed that the selective dipeptidyl peptidase inhibitor encompasses a multifunctional mechanism of action reflecting the ability to enhance the activity of CARTs as desired. The selective dipeptidyl peptidase inhibitor and PD-1 antagonist shows synergism in the release of IL-15 and IL-7, these cytokines are associated with metabolic pathways required for memory T-cell generation and thus would prolong the anti-tumor immune response of the CART.

More specifically, the present invention provides that the combination comprising:
(i) Talabostat
(ii) an immune checkpoint inhibitor
(iii) engineered CAR-T or CAR-NK cells In another embodiment, the invention relates to methods of treating a cancer with Talabostat that selectively inhibits the activity of dipeptidyl peptidase (for example, FAP or DPP 8/9) in combination with an immune-modulating approach utilizing engineered T cells or NK cells targeting one or more tumor antigens including, but are not limited to the list of CTLA4, PD-1, PD-L1, PD-L2, TIM3, LAG3, VISTA, KIR2D, IDO, A2AR, OX40.

In another embodiment, the present invention combination comprising Talabostat and PD-1 antagonist increases the innate immune response as compared with that of single agent alone in a method of treating a tumor. In particular, the innate immune response is increased by infiltration of innate immune cells, in particular macrophages into the blood, and NK-cells into the tumor. Further, the present invention combination suppresses the Treg function as compared with that of single agent alone in a method of treating a tumor.

The combination of Talabostat and PD-1 antagonist significantly increases the tumor infiltration of immune subpopulations, such as NK-cells and macrophages, compared to monotherapies by Talabostat and PD-1 antagonist, respectively.

III. Cancers/Tumors

Any of the provided methods can be used to treat a cancer that is a tumor, such as a tumor that is a solid tumor. In some examples, the tumor is characterized as having a moderate to high dipeptidyl peptidase expression, specifically FAP expression or DPP 8/9 expression. Exemplary cancers that can be treated by the provided methods include, but are not limited to, pancreatic cancer, colorectal cancer, ovarian cancer, lung cancer, breast cancer, glioblastoma, gastric cancer, astroglial, neuroectodermal tumors, head and neck cancer, triple negative breast cancer, gastroesophageal cancer, non-small cell lung cancer.

The present invention is also useful for treatment of metastatic cancers, especially metastatic cancers that express PD-L1 or CTLA4.

In some embodiments, the present invention provides a method of treating cancer in a subject, comprising administering to the subject a therapeutically effective amount of a selective dipeptidyl peptidase inhibitor (for example FAP inhibitor or DPP 8/9 inhibitor) and a therapeutically effective amount of an immune checkpoint inhibitor.

Preferred cancers whose growth may be inhibited using the combination therapy of a selective dipeptidyl peptidase inhibitor, for example, Talabostat and a PD-1 antagonist include cancers typically responsive to immunotherapy. Non-limiting examples of preferred cancers for treatment include malignant melanoma, non-small cell lung cancer, renal cancer, hodgkin's disease, gastric cancer, glioblastoma; head and neck cancer, hepatocellular carcinoma, multiple myeloma, oesophageal cancer, small cell lung cancer, urogenital cancer, acute myeloid leukemia, breast cancer, chronic lymphocytic leukemia, diffuse large B cell lymphoma, follicular lymphoma; myelodysplastic syndromes; ovarian cancer; uveal melanoma, colorectal cancer, hematological malignancies, non-hodgkin's lymphoma, chronic myeloid leukemia and glioma. Additionally, the invention includes refractory or recurrent malignancies whose growth may be inhibited using the antibodies of the invention.

Preferred cancers whose growth may be inhibited using the combination therapy of a selective dipeptidyl peptidase inhibitor, for example, Talabostat and a CTLA4 antagonist include cancers typically responsive to immunotherapy. Non-limiting examples of preferred cancers for treatment include melanoma (e.g., metastatic malignant melanoma), renal cancer (e.g., clear cell carcinoma), prostate cancer (e.g., hormone refractory prostate adenocarcinoma), breast cancer, glioblastoma, colon cancer and lung cancer (e.g., non-small cell lung cancer, small cell lung cancer), gastric cancer, myelodysplastic syndromes; oesophageal cancer; ovarian cancer; urogenital cancer; uveal melanoma, adrenal cancer; liver cancer. Additionally, the invention includes refractory or recurrent malignancies whose growth may be inhibited using the antibodies of the invention.

In some embodiments of the methods, uses, compositions, and kits described herein, the cancer is a solid tumor. In some embodiments, the cancer is urogenital cancers (such as prostate cancer, renal cell cancer, bladder cancer), thyroid cancer, testicular cancer, vulvar cancer, Wilms tumor, hormone sensitive or hormone refractory prostate cancer, gynecological cancers (such as ovarian cancer, cervical cancer, endometrial cancer, uterine cancer), lung cancer, non-small cell lung cancer, small cell lung cancer, gastrointestinal stromal cancers, gastrointestinal cancers (such as non-metastatic or metastatic colorectal cancers, pancreatic cancer, gastric cancer, oesophageal cancer, hepatocellular cancer, cholangiocellular cancer), malignant glioblastoma, malignant mesothelioma, non-metastatic or metastatic breast cancer (such as hormone refractory metastatic breast cancer, triple negative breast cancer), malignant melanoma, melanoma, metastatic melanoma, merkel cell carcinoma or bone and soft tissue sarcomas, oral squamous cell carcinoma, glioblastoma, brain cancer, osteosarcoma, neuroblastoma, advanced metastatic, an inflammatory myofibroblastic tumor (IMT), cholangiocarcinoma, cystadenocarcionoma, ameloblastoma, chondrosarcoma, dermatofibrosarcoma, ganglioglioma, leiomyosarcoma, medulloblastomma, osteoblastoma and inoperable non-inflammatory locally advanced disease and the like. The most preferred cancer is solid tumor (such as pancreatic cancer, colorectal cancer, ovarian cancer, lung cancer, breast cancer, glioblastoma, gastric cancer, astroglial, neuroectodermal tumors, head and neck cancer, triple negative breast cancer, gastroesophageal cancer, non-small cell lung cancer and the like) or hematopoietic cancer (leukemia, lymphoma, a lymphocytic leukemia, non-hodgkin's lymphoma, hodgkin's lymphoma, an anaplastic large-cell lymphoma, myeloid leukemia, multiple myeloma, acute lymphoblastic leukemia, chronic myeloid leukemia, acute myeloid leukemia).

In some embodiments, the cancers whose growth may be inhibited using the combination therapy of a selective dipeptidyl peptidase inhibitor(s) and an immune checkpoint inhibitor(s) are virally-associated cancers. Exemplary virally-associated cancers include, but are not limited to, cancers associated with Epstein-Barr virus (EBV), hepatitis B virus (HBV), hepatitis C virus (HCV), human papilloma viruses (HPV), human T lymphotropic virus type 1 (HTLV-1), human T lymphotropic type 2 (HTLV-2) and human herpesvirus, such as human herpesvirus 8 (HHV-8). The cancers associated with particular viruses are known to those of ordinary skill in the art. For example, examples of EBV-associated cancers include, but are not limited to, lymphomas, nasopharyngeal cancer, gastric carcinoma, parotid carcinoma, breast carcinoma, and leiomyosarcoma. Examples of cancers associated with hepatitis B virus (HBV) and hepatitis C virus (HCV) include, but are not limited to cancers of the liver. Examples of cancers associated with human papilloma viruses (HPV) include, but are not limited to, oropharyngeal head and neck cancer, nasopharyngeal head and neck cancer, and cancers of the cervix, vulva, vagina, penis and anus. Examples of cancers associated with human T lymphotropic virus type 1 (HTLV-1) and type 2 (HTLV-2) include, but are not limited to, adult T-cell leukemia and hairy-cell leukemia, respectively. Examples of cancers associated with human herpesvirus 8 (HHV-8) include, but are not limited to, Kaposi sarcoma. In some embodiments, the virally-associated cancer is a cancer associated with HPV. In other embodiments, the virally-associated cancer is a cancer associated with HCV.

In one embodiment, the present invention provides methods and compositions for inducing or enhancing an immune response in host for treating cancer. Because these methods operate by enhancing an immune response by blocking inhibitory receptors on T cells and NK cells, they are applicable to a very broad range of cancers.

In some embodiments, the methods, uses, compositions and kits described herein, the subject is a human. In some embodiments, the subject has cancer or has been diagnosed with cancer. In some embodiments, the subject is suffering from replaced or refractory cancer (such as solid tumor). In some embodiments, the subject is suffering from solid tumor (such as pancreatic cancer, colorectal cancer, ovarian cancer, lung cancer, breast cancer, glioblastoma, gastric cancer, astroglial, neuroectodermal tumors, head and neck cancer, triple negative breast cancer, gastroesophageal cancer, non-small cell lung cancer and the like).

In some embodiments, the subject has cancer or has been diagnosed with cancer. In some embodiments, the subject is suffering from rare non-immunogenic cancer include but not limited to medulloepithelioma, alveolar soft tissue sarcoma, pleural mesothelioma, retinoblastoma, rhabdomyosarcoma, squamous cell carcinoma of head and neck, thymic carcinoma, thymoma, undifferentiated pleomorphic sarcoma, vaginal carcinoma.

The methods of this invention may find use in treating conditions where enhanced immunogenicity is desired such as increasing tumor immunogenicity for the treatment of cancer. A variety of cancers may be treated, or their progression may be delayed, including but are not limited to a cancer that is a solid tumor. In some embodiments, the cancer is a refractory or metastatic cancer. In some embodiments, the cancer is a lymphoma or a leukemia. In some embodiments, the leukemia is chronic lymphocytic leukemia (CLL) or acute myeloid leukemia (AML). In some embodiments, the lymphoma is follicular lymphoma (FL), diffuse large B-cell lymphoma (DLBCL), or non-hodgkin's lymphoma (NHL).

IV. Administration

Suitable administration/treatment protocols for treating cancer or tumor in a subject include, for example, administering to the patient an effective amount of a selective dipeptidyl peptidase inhibitor (for example, Talabostat) and an immune checkpoint inhibitor.

In some embodiments, the combination therapy of the invention comprises administration of a selective dipeptidyl peptidase inhibitor (for example, Talabostat) and an immune checkpoint inhibitor. In some embodiments, the immune checkpoint inhibitor in the combination therapy can be a PD-1 axis antagonist. In one embodiment, the immune checkpoint inhibitor in the combination therapy is a PD-1 antagonist. In one embodiment, the immune checkpoint inhibitor in the combination therapy is a PD-L1 antagonist. In one embodiment, the immune checkpoint inhibitor in the combination therapy is a PD-L2 antagonist. The selective dipeptidyl peptidase inhibitor and the immune checkpoint inhibitor may be administered in any suitable manner known in the art. For example, the selective dipeptidyl peptidase inhibitor and the immune checkpoint inhibitor may be administered sequentially (at different times) or concurrently (at the same time).

In some embodiments, the PD-1 antagonist can be selected from the group consisting of ANA011, BGB-A317, KD033, Pembrolizumab, MCLA-134, mDX400, MEDI0680, muDX400, Nivolumab, PDR001, PF-06801591, Pidilizumab, REGN-2810, SHR 1210, STI-A1110, TSR-042, ANB011, 244C8, 388D4, TSR042 and XCE853, and the preferred one is Pembrolizumab, Nivolumab or Pidilizumab. In some embodiments, the PD-L1 antagonist can be selected from the group consisting of Avelumab, BMS-936559, CA-170, Durvalumab, MCLA-145, SP142, STI-A1011, STI-A1012, STI-A1010, STI-A1014, A110, KY1003 and Atezolimumab and the preferred one is Durvalumab or Atezolimumab. In some embodiments, the PD-L2 antagonist can be AMP-224 and/or rHIgM12B7.

In some embodiments, the immune checkpoint inhibitor is administered before administration of the selective dipeptidyl peptidase inhibitor (for example, Talabostat). In some embodiments, the immune checkpoint inhibitor is administered simultaneously with administration of the selective dipeptidyl peptidase inhibitor. In some embodiments, the immune checkpoint inhibitor is administered after administration of the selective dipeptidyl peptidase inhibitor.

In some embodiments, the selective dipeptidyl peptidase inhibitor or an immune checkpoint inhibitor is administered continuously. In some embodiments, the selective dipeptidyl peptidase inhibitor or immune checkpoint inhibitor is administered intermittently.

In some embodiments, the immune checkpoint inhibitor and the selective dipeptidyl peptidase inhibitor is co-administered, for example, the administration of said immune checkpoint inhibitor and the selective dipeptidyl peptidase inhibitor (for example Talabostat) as two separate formulations. The co-administration can be simultaneous or sequential in either order. In one further embodiment, there is a time period while both (or all) therapeutic agents simultaneously exert their biological activities. Said immune checkpoint inhibitor and selective dipeptidyl peptidase inhibitor (for example Talabostat) are co-administered either simultaneously or sequentially for example, oral or intravenous (i.v.) through a continuous infusion. When both therapeutic agents are co-administered sequentially the therapeutic agents are administered in two separate administrations that are separated by a "specific period of time". The term specific period of time is meant anywhere from 1 hour to 30 days. For example, one of the agents can be administered within about 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 day, or 24, 23, 22, 21, 20, 19, 18, 17, 16, 15, 14, 13, 12, 11, 10, 9, 8, 7, 6, 5, 4, 3, 2 or 1 hour from the administration of the other therapeutic agent, and, in one embodiment, the specific period time is 10, 9, 8, 7, 6, 5, 4, 3, 2, or 1 day, or 24, 23, 22, 21, 20, 19, 18, 17, 16, 15, 14, 13, 12, 11, 10, 9, 8, 7, 6, 5, 4, 3, 2 or 1 hour. In some embodiments, simultaneous administration means at the same time or within a short period of time, usually less than 1 hour.

A dosing period as used herein is meant for a period of time, during which each therapeutic agent has been administered at least once. A dosing period is usually about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, and, in one embodiment, 6, 7, 8, 9, 10, 11, 12, 13, 14, 16 or 24 days, for example, 8 or 16 or 24 days.

In certain embodiments, multiple (for example, 2, 3, 4, 5, 6, 7, 8, 9, 10 or more) doses of a selective dipeptidyl peptidase inhibitor (for example Talabostat) and multiple (for example, 2, 3, 4, 5, 6, 7, 8, 9, 10 or more) doses of an immune checkpoint inhibitor are administered to a subject in need of treatment.

In certain embodiments, the immune checkpoint inhibitor is administered in a dose of 0.01 mg/kg, 0.05 mg/kg, 0.1 mg/kg, 0.2 mg/kg, 0.3 mg/kg, 0.5 mg/kg, 0.7 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg or 30 mg/kg. The dose of the immune checkpoint inhibitor may vary from about 0.01 mg/kg to 30 mg/kg, preferably 0.1 mg/kg to 20 mg/kg, more preferably 1 mg/kg to 10 mg/kg. In certain embodiments, the immune checkpoint inhibitor is administered by injection (e.g., subcutaneously or intravenously) at a dose of about 0.01 mg/kg to 30 mg/kg, e.g., about 0.1 mg/kg to 20 mg/kg, about 1 mg/kg to 10 mg/kg, about 1 mg/kg to 5 mg/kg, or about 1 to 3 mg/kg.

In certain embodiments, the immune checkpoint inhibitor is administered one dose per day, one dose every 2 days, one dose every 3 days, one dose every 4 days, one dose every 5 days, once a week, once every two weeks, once every three weeks or once every four weeks, preferably once a week. In certain embodiments, the immune checkpoint inhibitor is administered as a single dose, in two doses, in three doses, in four doses, in five doses, or in 6 or more doses. The dosing schedule can vary from e.g., once a week to once every 2, 3, or 4 weeks. In one embodiment, the immune checkpoint inhibitor is administered at a dose from about 1 mg/kg to 10 mg/kg once a week.

In certain embodiments, the selective dipeptidyl peptidase inhibitor (for example Talabostat) is administered in a dose of 0.001 mg/kg, 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.010 mg/kg, 0.012 mg/kg, 0.013 mg/kg, 0.014 mg/kg, 0.020 mg/kg, 0.025 mg/kg, 0.030 mg/kg, 0.035 mg/kg, 0.06 mg/kg and 0.08 mg/kg. In preferred embodiments, each dose of the selective dipeptidyl peptidase inhibitor is administered at 0.002 mg/kg, 0.003 mg/kg, 0.004 mg/kg, 0.005 mg/kg, 0.006 mg/kg, 0.007 mg/kg, 0.009 mg/kg, 0.01 mg/kg, 0.013 mg/kg and 0.014 mg/kg. In another embodiment, the dosage of the selective dipeptidyl peptidase inhibitor of the invention administered to prevent and/or treat a cancer associated with increased levels of FAP or DPP 8/9 in a patient is a unit dose of about 0.001 mg/kg to about 10 mg/kg, 0.001 mg/kg to about 1 mg/kg, about 0.001 mg/kg to 0.05 mg/kg, about 0.001 mg/kg to 0.035 mg/kg, about 0.002 mg/kg to about 5 mg/kg, about 0.002 mg/kg to about 3 mg/kg, about 0.002 mg/kg to about 2 mg/kg, about 0.002 mg/kg to about 0.05 mg/kg, about 0.002 mg/kg to about 0.035 mg/kg, about 0.003 mg/kg to about 2.0 mg/kg, about 0.003 mg/kg to about 2.0 mg/kg, about 0.004 mg/kg to about 2.5 mg/kg, about 0.005 mg/kg to about 2.5 mg/kg, about 0.006 mg/kg to about 2.5 mg/kg, about 0.007 mg/kg to about 2.5 mg/kg, about 0.008 mg/kg to about 2.5 mg/kg, about 0.009 mg/kg to about 2.5 mg/kg, about 0.010 mg/kg to about 1.5 mg/kg, about 0.011 mg/kg to about 1.5 mg/kg, about 0.012 mg/kg to about 1 mg/kg, about 0.013 mg/kg to about 1 mg/kg, Total daily dose of a selective dipeptidyl peptidase inhibitor may vary from about 100 mcg to 200 mg, preferably about 100 mcg to 50 mg, most preferably about 100 mcg to 10 mg. Total daily dose of Talabostat may vary from about 50 mcg to 3 mg, preferably about 100 mcg to 2.5 mg, most preferably about 100 mcg to 2.0 mg The dose of a selective dipeptidyl peptidase inhibitor may vary from about 0.001 mg/kg to 10 mg/kg, preferably 0.001 mg/kg to 3 mg/kg, more preferably about 0.001 mg/kg to 2 mg/kg. The dose of Talabostat may vary from about 0.001 mg/kg to 1 mg/kg, preferably 0.001 mg/kg to 0.08 mg/kg, preferably 0.001 mg/kg to 0.05 mg/kg, and more preferably about 0.001 mg/kg to 0.035 mg/kg.

In certain embodiments, the selective dipeptidyl peptidase inhibitor is administered twice a day, one dose per day, one dose every 2 days, one dose every 3 days, one dose every 4 days, one dose every 5 days, once a week, once every two weeks, or once every four weeks, preferably one dose per day. In certain embodiments, the selective dipeptidyl peptidase inhibitor is administered as a single dose, in two doses, in three doses, in four doses, in five doses, or in 6 or more doses. The dosing schedule can vary from e.g., once a day to once every 2, 3, or 4 weeks. In one embodiment, the selective dipeptidyl peptidase inhibitor is administered at a dose from about 0.001 mg/kg to 3 mg/kg once a day. In certain embodiments, the dose frequency may vary from twice a day to once very month.

Suitable treatment protocols for treating a human patient afflicted with cancer include, for example, administering to the patient an effective amount of each of:
(i) Talabostat,
(ii) a PD-1 axis antagonist
wherein the method comprises at least one administration cycle, wherein the cycle is a period of 24 days, wherein for each of the at least one cycles, Talabostat administered continuously for seven days at a dose of about 0.001 mg/kg to 0.035 mg/kg body weight and the PD-1 axis antagonist is administered at a dose of 0.1-20 mg/kg body weight on every eighth day, after this 24 days cycle and a rest period of 7 days is recommended and then next administration cycle is started until there is relief in the disease state or as directed by the physician. This included the administration of PD-1 axis antagonist at a regular interval (for example, once a week) after the dosing of selective dipeptidyl peptidase inhibitor (for example, Talabostat).

In another embodiment, the selective dipeptidyl peptidase inhibitor is formulated for oral administration and/or PD-1 axis antagonist is formulated for intravenous administration. In one embodiment, the PD-1 axis antagonist is administered on Days 8, 16, 24 of each cycle. In another embodiment, the selective dipeptidyl peptidase inhibitor is administered daily. In the preferred embodiment, the administration cycle comprises once a day administration of Talabostat on day 1, 2, 3, 4, 5, 6, 7, 9, 10, 11, 12, 13, 14, 15, 17, 18, 19, 20, 21, 22 and 23; and once a day administration of PD-1 axis antagonist on day 8, 16 and 24 and followed by a rest period of 1 week.

In another embodiment, 21 doses of the selective dipeptidyl peptidase inhibitor are administered in the 24-days' cycle. In another embodiment, 3 doses of the PD-1 axis antagonist are administered on every eighth day for 24-days' cycle.

In another embodiment, a cycle of administration is 24 days, which can be repeated, as necessary. In another embodiment, the treatment consists of up to 12 cycles.

In certain embodiments, each dose of the selective dipeptidyl peptidase inhibitor is administered at 0.001, 0.003, 0.005, 0.006, 0.007, 0.008, 0.009, 0.01, 0.012, 0.013, 0.020, 0.025, 0.030 mg/kg and 0.035 mg/kg body weight. In preferred embodiments, each dose of the selective dipeptidyl peptidase inhibitor (for example, FAP Inhibitor or DPP 8/9 inhibitor) is administered at about 0.003 mg/kg, about 0.004 mg/kg, about 0.005 mg/kg, about 0.006 mg/kg, about 0.007 mg/kg, about 0.009 mg/kg, about 0.01 mg/kg, about 0.013 mg/kg and about 0.014 mg/kg.

In other embodiments, each dose of the PD-1 axis antagonist is administered at 0.1, 0.3, 1, 3, 6, 10 or 20 mg/kg body weight. In preferred embodiments, each dose of the PD-1 axis antagonist is administered at 0.3, 1, 3 or 10 mg/kg. In more preferred embodiments, the PD-1 axis antagonist is administered at a dose of 2 mg/kg on every three weeks (KEYTRUDA®) or 3 mg/kg on every two weeks (OPDIVO®) or 1200 mg on every three weeks (Atezolizumab; TECENTRIQ®).

In one embodiment, the Talabostat and PD-1 axis antagonist or CTLA antagonist are administered at the following doses:
a) About 0.002 mg/kg of Talabostat and 2 mg/kg or 3 mg/kg or 1200 mg of PD-1 axis antagonist or 3 mg/kg of CTLA4 antagonist;
b) About 0.003 mg/kg of Talabostat and 2 mg/kg or 3 mg/kg or 1200 mg of PD-1 axis antagonist or 3 mg/kg of CTLA4 antagonist;
c) About 0.004 mg/kg of Talabostat and 2 mg/kg or 3 mg/kg or 1200 mg of PD-1 axis antagonist or 3 mg/kg of CTLA4 antagonist;
d) About 0.005 mg/kg of Talabostat and 2 mg/kg or 3 mg/kg or 1200 mg of PD-1 axis antagonist or 3 mg/kg of CTLA4 antagonist;
e) About 0.006 mg/kg of Talabostat and 2 mg/kg or 3 mg/kg or 1200 mg of PD-1 axis antagonist or 3 mg/kg of CTLA4 antagonist;
f) About 0.007 mg/kg of Talabostatand 2 mg/kg or 3 mg/kg or 1200 mg of PD-1 axis antagonist or 3 mg/kg of CTLA4 antagonist;
g) About 0.008 mg/kg of Talabostat and 2 mg/kg or 3 mg/kg or 1200 mg of PD-1 axis antagonist or 3 mg/kg of CTLA4 antagonist;
h) About 0.009 mg/kg of Talabostatand 2 mg/kg or 3 mg/kg or 1200 mg of PD-1 axis antagonist or 3 mg/kg of CTLA4 antagonist;
i) About 0.010 mg/kg of Talabostat and 2 mg/kg or 3 mg/kg or 1200 mg of PD-1 axis antagonist or 3 mg/kg of CTLA4 antagonist;
j) About 0.012 mg/kg of Talabostat and 2 mg/kg or 3 mg/kg or 1200 mg of PD-1 axis antagonist or 3 mg/kg of CTLA4 antagonist;
k) About 0.013 mg/kg of Talabostat and 2 mg/kg or 3 mg/kg or 1200 mg of PD-1 axis antagonist or 3 mg/kg of CTLA4 antagonist.

In another embodiment, the dose of the selective dipeptidyl peptidase inhibitor and/or PD-1 axis antagonist is varied over time. For example, the selective dipeptidyl peptidase inhibitor and/or PD-1 axis antagonist may be initially administered at a high dose and may be lowered over time. In another embodiment, the selective dipeptidyl peptidase inhibitor and/or PD-1 axis antagonist is initially administered at a low dose and increased over time.

In another embodiment, the amount of the selective dipeptidyl peptidase inhibitor and/or PD-1 axis antagonist administered is constant for each dose. In another embodiment, the amount of therapeutic agent administered varies with each dose. For example, the maintenance (or follow-on) dose of the therapeutic agent can be higher or the same as the loading dose which is first administered. In another embodiment, the maintenance dose of the therapeutic agent can be lower or the same as the loading dose.

The immune checkpoint inhibitor can be administered at the same frequency as the selective dipeptidyl peptidase inhibitor or at a different frequency, wherein each administration of the immune checkpoint inhibitor is preceded by an administration of selective dipeptidyl peptidase inhibitor by not more than 48 hours. For example, the immune checkpoint inhibitor can be administered twice weekly, once weekly, once every 2 weeks, once every 3 weeks, once every 4 weeks, once every 6 weeks, once every 2 months, once every 3 months, once every 4 months, once every 5 months, or once every 6 months; wherein each administration of the immune checkpoint inhibitor is preceded by an administration of selective dipeptidyl peptidase inhibitor by not more than 10 days, not more than 9 days, not more than 8 days, not more than 7 days, not more than 6 days, not more than 5 days, not more than 4 days, not more than 3 days, not more than 2 days, not more than 1 day.

In other embodiments, the selective dipeptidyl peptidase inhibitor and/or PD-1 antagonist is administered as long as a clinical benefit is observed or until there is a complete response, confirmed progressive disease or unmanageable toxicity.

In another embodiment, the PD-1 antagonist and selective dipeptidyl peptidase inhibitor are administered as a first line of treatment (e.g., the initial or first treatment). In another embodiment, the PD-1 antagonist and selective dipeptidyl peptidase inhibitor are administered as a second line of treatment (e.g., after the initial or first treatment, including after relapse and/or where the first treatment has failed).

In another aspect, the invention features any of the aforementioned embodiments, wherein the PD-1 antagonist is replaced by, or combined with, an PD-L1 antagonist or PD-L2 antagonist and the PD-1 axis antagonist includes PD-1 antagonist, PD-L1 antagonist and PD-L2 antagonist.

The appropriate dosage of the selective dipeptidyl peptidase inhibitor (for example, Talabostat) and/or the immune checkpoint inhibitor may be determined based on the type of disease to be treated, the type of the selective dipeptidyl peptidase inhibitor and the immune checkpoint inhibitor, the severity and course of the disease, the clinical condition of the subject, the subject's clinical history and response to the treatment, the symptoms involved, the subject's body mass, gender, immune status and the discretion of the attending physician. Suitable regimens can be selected by one skilled in the art by considering such factors and by following, for example, dosages reported in literature and recommended in the Physician's Desk Reference (59th ed., 2005).

Preferably, the dosages of therapeutic agents used in combination therapies of the invention are lower than those which have been or are currently being used to prevent and/or treat a tumor associated with increased levels of FAP or DPP 8/9 and/or an immune checkpoint molecule.

In some embodiments, a method of treating cancer will be performed even with a low likelihood of success, but which, given the medical history and estimated survival expectancy of a patient, is nevertheless deemed to induce an overall beneficial course of action.

Accordingly, in one embodiment, the dose of the selective dipeptidyl peptidase inhibitor and immune checkpoint inhibitor is calculated as mg/kg body weight. However, in another embodiment, the dose of the selective dipeptidyl peptidase inhibitor and/or immune checkpoint inhibitor is a flat fixed dose that is fixed irrespective of the weight of the patient.

The selective dipeptidyl peptidase inhibitor (for example, Talabostat) and the immune checkpoint inhibitor may be administered by the same route of administration or by different routes of administration. In some embodiments, the selective dipeptidyl peptidase inhibitor is administered orally, intravenously, intramuscularly, subcutaneously, topically, rectally, transdermally, intratracheally, vaginally, intraperitoneally, intraorbitally, by implantation, by inhalation, intrathecally, intraventricularly or intranasally. The preferred route of administration is oral. The selective dipeptidyl peptidase inhibitor can be administered to a subject by any route that delivers the inhibitor to the affected site, either directly or indirectly. Delivery may be local (e.g., mucosal) or systemic. The selective dipeptidyl peptidase inhibitor is administered orally, and an immune checkpoint inhibitor is administered by a non-oral route.

In some embodiments, the immune checkpoint inhibitor is administered intravenously, intramuscularly, subcutaneously, topically, orally, transdermally, intraperitoneally, intraorbitally, by implantation, by inhalation, intrathecally, intraventricularly, or intranasally, preferably intravenously. In some embodiments, the immune checkpoint inhibitor is a PD-L1 antagonist (for example anti-PD-L1 antibody). In some embodiments, the anti-PD-L1 antibody is administered to the subject intravenously at a dose of 120 mg once every three weeks. In some embodiments, the anti-PD-L1 antibody is administered with a selective dipeptidyl peptidase inhibitor (for example, Talabostat or its pharmaceutically acceptable salts, solvates, derivative thereof).

V. Pharmaceutical Composition/Formulations

Also, provided herein are pharmaceutical compositions or formulations comprising the selective dipeptidyl peptidase inhibitor (for example, Talabostat) and/or an immune checkpoint inhibitor and one or more pharmaceutically acceptable carrier(s) or adjuvant(s). The selective dipeptidyl peptidase inhibitor (Talabostat) may be formulated separately or together with an immune checkpoint inhibitor. Being formulated together means that the agents are present in the same composition prior to administration to the subject. Being formulated separately means the agents are present in separate and distinct compositions prior to administration to the subject.

In one embodiment, the present invention provides a composition comprising the selective dipeptidyl peptidase inhibitor (for example, Talabostat) and one or more pharmaceutically acceptable carrier(s). Any of the pharmaceutically acceptable carrier described herein or known in the art may be used.

In a still further embodiment, the invention provides for a composition comprising an immune checkpoint inhibitor such as a PD-1 antagonist, PD-L1 antagonist, or a PD-L2 antagonist or a CTLA4 antagonist as provided herein and one or more pharmaceutically acceptable carrier(s) or adjuvant(s). Any of the pharmaceutically acceptable carrier described herein or known in the art may be used.

As used herein, the term "pharmaceutical composition" refers to a composition comprising at least one active therapeutic agent (for example, a selective dipeptidyl peptidase inhibitor or an immune checkpoint inhibitor) and one or more pharmaceutically acceptable carrier(s). Pharmaceutically acceptable carriers or adjuvants are well known to the skilled in the art, and usually depend on the chosen route of administration, even water is included as an example of carrier or adjuvant. In some embodiments, the mixture comprises at least one selective dipeptidyl peptidase inhibitor (for example, Talabostat) in an amount that results in an additive or a synergistic effect with at least one immune checkpoint inhibitor in a subject when both are administered simultaneously (for example, in a single formulation or concurrently as separate formulations). In some embodiments, a first composition comprising the selective dipeptidyl peptidase inhibitor and one or more pharmaceutically acceptable carrier(s) and a second composition comprising an immune checkpoint inhibitor and one or more pharmaceutically acceptable carrier(s) wherein both are present in an amount that results in an additive or a synergistic effect when both are administered sequentially (as a separate formulations) to the subject. In another preferred embodiment, the present combination used for treating, prevention and ameliorating the tumor is administered orally and/or subcutaneously or intravenously.

Pharmaceutical compositions suitable for administration to human patients are typically formulated for parenteral administration, e.g., in a liquid carrier, or suitable for reconstitution into liquid solution or suspension for parenteral administration. In general, such compositions typically comprise a pharmaceutically acceptable carrier. As used herein, the term "pharmaceutically acceptable" means approved by a government regulatory agency or listed in the U.S. Pharmacopeia or another generally recognized pharmacopeia for use in animals, particularly in humans. Pharmaceutical compositions and formulations as described herein can be prepared by mixing the therapeutic agent (for example, antibody) having the desired degree of purity with one or more pharmaceutically acceptable carrier(s) (Remington's Pharmaceutical Sciences 16th edition, Osol, A. Ed. (1980)), in the form of lyophilized formulations or aqueous solutions. The term "carrier" refers to a diluent, adjuvant, excipient, or vehicle with which the compound is administered. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride, hexamethonium chloride, benzalkonium chloride, benzethonium chloride, phenol, butyl or benzyl alcohol, chlorobutanol, thimerosal's, alkyl parabens such as methyl or propyl paraben, catechol, resorcinol, cyclohexanol, 3-pentanol and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; chelating agents such as EDTA; monosaccharides, disaccharides, and other carbohydrates including sugars such as sucrose, mannitol, trehalose or sorbitol, glucose, mannose, or dextrins; salt-forming counter-ions such as sodium; metal complexes (for example, Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). The carrier can be a solvent or reconstitution medium or dispersion medium containing, for example, water, ethanol, polyol (for example, glycerol, propylene glycol, and liquid polyethylene glycol, and the like), and suitable mixtures thereof. For intravenous administration, suitable carriers include physiological saline, bacteriostatic water, Cremophor EL (BASF, Parsippany, N.J.) or phosphate buffered saline (PBS). Prolonged absorption of the injectable compositions can be brought about by including in the composition an agent which delays absorption, for example, aluminium monostearate and gelatin.

Solutions or suspensions used for subcutaneous application typically include one or more of the following components: a sterile carrier such as water for injection, saline solution, fixed oils, polyethylene glycols, glycerin, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The pH can be adjusted with acids or bases, such as hydrochloric acid or sodium hydroxide. Such preparations may be enclosed in ampoules, disposable syringes or multiple dose vials made of glass or plastic. The present invention also provides other formulations such as microcapsules, nanoparticles or sustained release compositions, intranasal compositions, oral compositions. Active agents may be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nanoparticles and nanocapsules) or in macro emulsions. Such techniques are disclosed in Remington's Pharmaceutical Sciences 16th edition, Osol, A. Ed. (1980). In certain embodiments, the presently disclosed therapeutic agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions containing the presently disclosed antibodies can also be used as pharmaceutically acceptable carriers. Suitable examples of sustained release preparations include semipermeable matrices of solid hydrophobic polymers containing the therapeutic agent (for example, antibody) wherein the matrices are in the form of shaped articles, e.g. films, or microcapsules. The formulations to be used for in vivo administration are generally sterile. Sterility may be readily accomplished, e.g., by filtration through sterile filtration membranes.

For oral use, the pharmaceutical compositions of the present invention, may be administered, for example, in the form of tablets or capsules, powders, dispersible granules, or cachets, or as aqueous solutions or suspensions. Oral compositions generally include an inert carrier (for example, diluent) or an edible carrier. They can be enclosed in gelatin capsules or compressed into tablets. For oral administration, the therapeutic agents can be combined with carriers and used in the form of tablets, troches, or capsules. Pharmaceutically compatible binding agents, and/or adjuvant materials can be included as part of the composition. The tablets, pills, capsules, troches, and the like can contain any of the following ingredients, or compounds of a similar nature; a binder such as microcrystalline cellulose, gum tragacanth or gelatin; an excipient such as starch or lactose, a disintegrating agent such as alginic acid, primogel, or corn starch; a lubricant such as magnesium stearate or stearates; a glidant such as colloidal silicon dioxide; a sweetening agent such as sucrose or saccharin; or a flavouring agent such as peppermint, methyl salicylate, or orange flavouring.

Liquid preparations may also include solutions for intranasal administration.

Aerosol preparations suitable for inhalation may include solutions and solids in powder form, which may be in combination with a pharmaceutically acceptable carrier, such as an inert compressed gas.

The amount of selective dipeptidyl peptidase inhibitor (for example, Talabostat) present in a composition should, in general, be in the range of about 0.01 to about 30% w/w and preferably in an amount of 0.5 to 20% w/w of the composition. Similarly, the amount of an immune checkpoint inhibitor present in a composition in the range of about 0.01 to about 30% w/w and preferably in an amount of 0.5 to 20% w/w of the composition. The immune checkpoint inhibitor is selected from the group comprising of PD-1 antagonist, PD-L1 antagonist, PD-L2 antagonist, CTLA4 antagonist.

The precise dose to be employed in the formulation will also depend on the route of administration, and the seriousness of the cancer, and should be decided according to the judgment of the practitioner and each patient's circumstances. Effective doses may be extrapolated from dose-response curves derived from in vitro or animal model test systems.

In some embodiments, the selective dipeptidyl peptidase inhibitor (described herein is in formulation comprising an effective amount of a selective dipeptidyl peptidase inhibitor and one or more pharmaceutically acceptable carrier(s) or adjuvant(s) selected from the group comprising bulking agent, buffer, surfactant, pH modifier and the formulation has an appropriate pH.

In some embodiments, the selective dipeptidyl peptidase inhibitor described herein is in formulation comprising an effective amount of a selective dipeptidyl peptidase inhibitor (for example, Talabostat), and one or more pharmaceutically acceptable carrier(s) or adjuvant(s) selected from the group comprising diluent, binder, disintegrant, glidant, surfactant and the table is free of organic acid.

In some embodiments, the PD-L1 antagonist (for example, anti-PD-L1 antibody) described herein is in formulation comprising the antibody at an amount of about 60 mg/mL, histidine acetate in a concentration of about 20 mM, sucrose in a concentration of about 120 mM, and polysorbate (e.g., polysorbate 20) in a concentration of 0.04% (w/v), and the formulation has a pH of about 5.8. In some embodiments, the anti-PD-L1 antibody described herein is in a formulation comprising the antibody in an amount of about 125 mg/mL, histidine acetate in a concentration of about 20 mM, sucrose is in a concentration of about 240 mM, and polysorbate (e.g. polysorbate 20) in a concentration of 0.02% (w/v), and the formulation has a pH of about 5.5.

In certain embodiments, the various processes of making above mentioned formulations or compositions are included and such compositions can be manufactured by any of the processes known in the art.

In another embodiment, the present invention relates to a pharmaceutical composition of Talabostat for oral administration and process of preparing such formulation. In some preferred embodiments, Talabostat is formulated as an oral tablet. The pharmaceutical tablet may be an immediate release or a modified release tablet. Tablet may be in the form of matrix or coated form.

An exemplary immediate release tablet comprises an effective amount of Talabostat and a pharmaceutically-acceptable carrier are selected from the diluents, binders, disintegrants, glidants, lubricants, pH modifying agents and combinations thereof.

Diluents: one or more diluents comprise, but are not limited to dibasic calcium phosphate, pullulan, maltodextrin, isomalt, sugar pellets, mannitol, spray-dried mannitol, microcrystalline cellulose, dibasic calcium phosphate dihydrate, lactose, sugars, sorbitol, mixture of microcrystalline cellulose and guar gum (Avicel CE-15), mixture of mannitol, polyplasdone and syloid (PHARMABURST®), mixture of mannitol, crospovidone and polyvinyl acetate (LUDIFLASH®), isomalt, PANEXCEA®, F-MELT®, sucrose, calcium salts and similar inorganic salts, heavy magnesium carbonate and the like, and the mixtures thereof. Preferably, it is lactose or microcrystalline cellulose.

Binders: one or more binders comprise, but are not limited to, low-substituted hydroxypropyl cellulose, xanthan gum, polyvinylpyrrolidone (povidone), gelatin, sugars, glucose, natural gums, gums, synthetic celluloses, polymethacrylate, hydroxypropyl methylcellulose, hydroxypropyl cellulose, carboxymethyl cellulose, methyl cellulose, and other cellulose derivatives and the like, and the mixtures thereof. Preferably, the binder is polyvinylpyrrolidone or hydroxypropyl cellulose or hydroxypropyl methylcellulose.

Disintegrants: one or more binders comprise, but are not limited to, at least one or a mixture of sodium starch glycolate, croscarmellose sodium, crospovidone, sodium alginate, gums, starch, and magnesium aluminium silicate. Preferably, the disintegrant is sodium starch glycolate.

Lubricants: one or lubricants comprise, but are not limited to sodium stearyl fumarate, sodium lauryl sulphate, magnesium stearate, polyethylene glycol, metal stearates, hydrogenated castor oil and the like, and the mixtures thereof. Preferably, the lubricant is magnesium stearate.

Glidant: one or glidants comprise, but are not limited to, stearic acid, colloidal silicon dioxide, talc, aluminium silicate and the like, and the mixtures thereof. Preferably, it is talc.

pH modifying agents: one or more pH modifying agents comprises, but are not limited to organic acid or its salts like phosphoric acid, citric acid and the like.

In one embodiment, the present invention provides the percentages or concentration of pharmaceutical acceptable excipients as tabulated below:

TABLE 2

| Formulation Content | Amount (w/w %) |
|---|---|
| Talabostat as a API | 0.01-2 |
| Binder | 5-50 |
| Disintegrant | 2-15 |
| Lubricant | 0.1-5 |
| Diluent | 30-98 |
| pH modifying agent | 0-15 |

Preferably the exemplary immediate release tablet of Talabostat includes the following:

TABLE 3

| Formulation content | Amount (w/w %) | Preferred ranges (w/w %) |
|---|---|---|
| Talabostat | 0.01-2 | 0.145 |
| Talabostat (69% free base) as a API | | |
| Polyvinyl pyrrolidone or hydroxypropylcellulose or hydroxypropylmethylcellulose or pregelatinized starch as a binder | 5-50 | 1.00 |
| Sodium starch glycolate or crospovidone as a disintegrant | 5-15 | 2.5 |
| Stearic acid as a lubricant | 0.1-5 | 1.500 |
| Lactose as a diluent | 30-90 | 85.315 |
| Microcrystalline cellulose as a diluent | 5-20 | 9.480 |
| Sodium phosphate monobasic, monohydrate as a pH modifying agent | 0-15 | 0.060 |
| Phosphoric acid as a pH modifying agent | For pH adjustment | For pH adjustment |

In some preferred embodiments, the amount of Talabostat in a unit dose is about 100 micrograms per tablet, about 200 micrograms per tablet, about 300 micrograms per tablet, about 400 micrograms per tablet, about 500 micrograms per tablet, about 600 micrograms per tablet, about 700 micrograms per tablet, about 800 micrograms per tablet.

In some preferred embodiments, Talabostat are formulated as a modified release matrix tablet. An exemplary extended release tablet comprises an effective amount of Talabostat and pharmaceutically-acceptable carrier or adjuvant are selected from the diluents, binders, modified release material, glidants, lubricants, colorants and combinations thereof. Alternatively, a modified release tablet comprises immediate release core and coating wherein said coating comprises modified release material and other pharmaceutical excipients.

Modified release material comprise, but are not limited to polyvinyl pyrrolidone (K90), Hydroxypropylmethylcellulose (K4M, K10), hydroxypropylcellulose (high viscosity grade), carnauba wax, glyceryl behenate, castor wax, polyvinyl acetate, carboxymethyl ethyl cellulose, ethylcellulose, cellulose phthalates or succinates, in particular cellulose acetate phthalate and hydroxypropylmethylcellulose phthalate, hydroxypropylmethylcellulose succinate or hydroxypropylmethylcellulose acetate succinate; high molecular polyalkylene oxides such as polyethylene oxide and polypropylene oxide and copolymers of ethylene oxide and propylene oxide and the like. Preferably, it is polyvinyl pyrrolidone (K90) or hydroxypropylmethylcellulose (K4M, K10) or hydroxypropylcellulose (high viscosity grade-HF), polyethylene oxide and the like. A modified release material is present in the range of 10-50% wt of the tablet.

Preferably the exemplary modified release tablet of Talabostat includes the following:

TABLE 4

| Formulation content | Amount (w/w %) |
| --- | --- |
| Talabostat as a API | 0.01-2 |
| Polyvinyl pyrrolidone (K90) or hydroxypropylmethylcellulose (K4M, K10) or hydroxypropylcellulose (high viscosity grade-HF) or polyethylene oxideas a modified release material | 10-50 |
| Sodium starch glycolate or crospovidone as a disintegrant | 0-10 |
| Magnesium stearate or stearic acid as a lubricant | 0.1-10 |
| Citric acid or phosphoric acid as a pH modifying agent | 0-15 |
| Lactose as a filler | 30-90 |

Thus, in one aspect, the invention provides a pharmaceutical tablet comprising particles consisting essentially of a Talabostat, diluent (e.g., lactose monohydrate) and optionally binder. The particles may be blended with one or more of a binder, a lubricant and a disintegrant and then compressed.

Various methods can be used for manufacturing the tablets according to the invention. More preferably the process includes dissolving Talabostat in a suitable solvent (with or without binder) and this solution is distributed uniformly all over filler particles (may contain other materials) to form agglomerated particles/granules. Wet granulation or coating or spraying process can be used for the same. Obtained granules are sized as per the requirement or the granules can be further processed by dry granulation/slugging/roller compaction method followed by milling step to achieve suitable granules of specific particle size distribution. The sized granules are further blended with other components and/or and then lubricated in a suitable blender and compressed into tablets of specific dimensions using appropriate tooling. The coating can be done with appropriate equipment.

VI. Kits

In some embodiments, a combination includes a formulation of a selective dipeptidyl peptidase inhibitor and an immune checkpoint inhibitor, with or without instructions for combined use or to combination products. The combined therapeutics can be manufactured and/or formulated by the same or different manufacturers. The combination therapeutics may thus be entirely separate pharmaceutical dosage forms or pharmaceutical compositions that are also sold independently of each other. In embodiments, instructions for their combined use are provided: (i) prior to release to physicians (e.g. in the case of a "kit of part" comprising a first therapeutic agent and the other therapeutic agent); (ii) by the physicians themselves (or under the guidance of a physician) shortly before administration; (iii) the patient themselves by a physician or medical staff.

In another aspect, provided is a kit comprising a selective dipeptidyl peptidase inhibitor and/or an immune checkpoint inhibitor for treating or delaying progression of a cancer in subject or for enhancing immune function of a subject having cancer. In some embodiments, the kit comprises a selective dipeptidyl peptidase inhibitor and a package insert comprising instructions for using the selective dipeptidyl peptidase inhibitor in combination with an immune checkpoint inhibitor to treat or delay progression of cancer in a subject or to enhance immune function of a subject having cancer. In some embodiments, the kit comprises an immune checkpoint inhibitor and a package insert comprising instructions for using the immune checkpoint inhibitor in combination with a selective dipeptidyl peptidase inhibitor to treat or delay progression of cancer in a subject or to enhance immune function of a subject having cancer. In some embodiments, the kit comprises a selective dipeptidyl peptidase inhibitor and an immune checkpoint inhibitor, and a package insert comprising instructions for using the selective dipeptidyl peptidase inhibitor and the immune checkpoint inhibitor to treat or delay progression of cancer in a subject or to enhance immune function of a subject having cancer. Any of the selective dipeptidyl peptidase inhibitor (for example, Talabostat) and/or immune checkpoint inhibitors described herein may be included in the kits.

In some embodiments, the kit comprises a container containing one or more of the selective dipeptidyl peptidase inhibitor and immune checkpoint inhibitors described herein. Suitable containers include, for example, bottles, vials (e.g., dual chamber vials), syringes (such as single or dual chamber syringes) and test tubes. The container may be formed from a variety of materials such as glass or plastic. In some embodiments, the kit may comprise a label (e.g., on or associated with the container) or a package insert. The label or the package insert may indicate that the compound contained therein may be useful or intended for treating or delaying progression of cancer in a subject or for enhancing immune function of a subject having cancer. The kit may further comprise other materials desirable from a commercial and user standpoint, including other buffers, diluents, filters, needles, and syringes. In one embodiment of the invention, an immune checkpoint inhibitor is PD-1 antagonist, PD-L1 antagonist, PD-L2 antagonist or CTLA4 antagonist.

Thus, in some embodiments, the present invention is directed to kits which comprise a first composition comprising the one or more selective dipeptidyl peptidase inhibitor and a second composition comprising one or more immune checkpoint inhibitors. In some embodiments, the first and second composition may be mixed together before administering to the subject. In some embodiments, the first and second compositions, may be administered either simultaneously or sequentially (i.e., spaced out over a period of time) so as to obtain the maximum efficacy, additivity, synergy, or a combination thereof of the combination).

The dosage regimen of the active principles and of the pharmaceutical composition described herein can be chosen by prescribing physicians, based on their knowledge of the art, including information published by regulatory authorities. For example, Nivolumab (OPDIVO®) is typically administered intravenously. According to the U.S. Food and Drug Administration (FDA), the recommended dose of OPDIVO® is 3 mg/kg administered as an intravenous infusion over 60 minutes every 2 weeks until disease progression.

In some embodiments of the methods, uses, compositions, and kits described herein, the immune checkpoint inhibitor is selected from the group consisting of a PD-1 antagonist, a PD-L1 antagonist and a PD-L2 antagonist. In some embodiments, the immune checkpoint inhibitor in the kit as described herein can be a PD-1 axis antagonist. In some embodiments, the PD-1 axis binding antagonist is a PD-1 antagonist. In some embodiments, the anti PD-1 antagonist inhibits the binding of PD-1 to its ligand binding partners. In some embodiments, the PD-1 antagonist inhibits the binding of PD-1 to PD-L1, PD-1 to PD-L2, or PD-1 to both PD-L1 and PD-L2.

VII. Outcomes

Patients treated according to the methods disclosed herein preferably experience improvement in at least one sign of cancer. In one embodiment, improvement is measured by a reduction in the quantity and/or size of measurable tumor lesions. In another embodiment, lesions can be measured on chest x-rays or CT or MRI films. In another embodiment, cytology or histology can be used to evaluate responsiveness to a therapy. In another embodiment, extension of progression free survival and/or overall survival is provided.

In specific aspects, the anti-tumor response is a tumor specific response, a clinical response, a decrease in tumor size/volume, a decrease in tumor specific biomarkers, increase in anti-tumor cytokines or a combination thereof.

In a specific aspect, the clinical response is a decreased tumor growth and/or a decrease in tumor size. In a specific aspect, the initiating, sustaining or enhancing an anti-tumor immune response is for the treatment of cancer.

In a further aspect, the anti-tumor response is inhibiting tumor growth, inducing tumor cell death, tumor regression, preventing or delaying tumor recurrence, tumor growth, tumor spread or tumor elimination.

In specific embodiments, the tumor response is a decrease in the number of tumor cells. In specific embodiments, the tumor response is a decreased rate in tumor growth. In specific embodiments, the tumor response is a block in the dipeptidyl peptidase enzyme activity. In specific embodiments, the tumor response is an induction of proinflammatory cytokine response and a cytotoxic T cell response.

The subject methods result in an inhibition of tumor size more than about 10%, more than about 20%, more than about 30%, more than about 35%, more than about 42%, more than about 43%, more than about 44%, more than about 45%, more than about 46%, more than about 47%, more than about 48%, more than about 49%, more than about 50%, more than about 51%, more than about 52%, more than about 53%, more than about 54%, more than about 55%, more than about 56%, more than about 57%, more than about 58%, more than about 59%, more than about 60%, more than about 65%, more than about 70%, more than about 75%, more than about 80%, more than about 85%, more than about 90%, more than about 95%, or more than about 100%.

In one embodiment, the patient treated exhibits a complete response (CR), a partial response (PR), stable disease (SD), immune-related complete disease (irCR), immune-related partial response (irPR), or immune-related stable disease (irSD). In another embodiment, the patient treated experiences tumor shrinkage and/or decrease in growth rate, i.e., suppression of tumor growth. In another embodiment, unwanted cell proliferation is reduced or inhibited. In yet another embodiment, one or more of the following can occur: the number of cancer cells can be reduced; tumor size can be reduced; cancer cell infiltration into peripheral organs can be inhibited, retarded, slowed, or stopped; tumor metastasis can be slowed or inhibited; tumor growth can be inhibited; recurrence of tumor can be prevented or delayed; one or more of the symptoms associated with cancer can be relieved to some extent.

In other embodiments, administration of effective amounts of the selective dipeptidyl peptidase inhibitor (for example, FAP inhibitor or DPP 8/9 inhibitor) and the PD-1 antagonist according to any of the methods provided herein produces at least one therapeutic effect selected from the group consisting of reduction in size of a tumor, reduction in number of metastatic lesions appearing over time, complete remission, partial remission, or stable disease. In still other embodiments, the methods of treatment produce a comparable clinical benefit rate (CBR=CR+PR+SD≥6 months) better than that achieved by a FAP inhibitor or DPP 8/9 inhibitor or PD-1 antagonist alone. In other embodiments, the improvement of clinical benefit rate is about 20%, 30%, 40%, 50%, 60%, 70%, 80% or more compared to a FAP inhibitor or DPP 8/9 inhibitor or PD-1 antagonist alone. In some embodiments, the CD8+ T cells in the individual have enhanced priming, activation, proliferation and/or cytolytic activity in the presence of combination of a selective dipeptidyl peptidase inhibitor and a PD-1 axis antagonist as compared to single agent administration.

In some embodiments, the CD8+ T cell priming is characterized by elevated CD44 expression and/or enhanced cytolytic activity in CD8+ T cells. In some embodiments, the CD8+ T cell activation is characterized by an elevated frequency of γ-IFN+ CD8+ T cells also by the release of granzyme B. In some embodiments, the CD8+ T cell is an antigen-specific T-cell. In some embodiments, the immune evasion is inhibited by signaling through PD-L1 surface expression is inhibited.

In some embodiments, the number of CD4+ and/or CD8+ T cells is elevated relative to prior to administration of the combination. In some embodiments, the activated CD4+ and/or CD8+ T cells is characterized by γ-IFN+ producing CD4+ and/or CD8+ T cells and/or enhanced cytolytic activity relative to prior to the administration of the combination. In some embodiments, the CD4+ and/or CD8+ T cells exhibit increased release of cytokines selected from the group consisting of IFN-γ, TNF-α, and interleukins (IL-2, IL-6, IL-12p40, IL-15).

In some embodiments, the CD4+ and/or CD8+ T cell is an effector memory T cell. In some embodiments, the CD4+ and/or CD8+ effector memory T cell is characterized by γ-IFN+ producing CD4+ and/or CD8+ T cells and/or enhanced cytolytic activity. In some embodiments, the CD4+ and/or CD8+ effector memory T cell is characterized by having the expression of CD44high CD62Llow as well as associated with IL-15 and IL-7 cytokine release.

In some embodiments, the antigen presenting cells in the individual have enhanced maturation and activation in the presence of combination of a selective dipeptidyl peptidase inhibitor and PD-1 antagonist as compared to single agent administration. In some embodiments, wherein the antigen presenting cells are dendritic cells. In some embodiments, the maturation of the antigen presenting cells is characterized by increased frequency of CD83+ dendritic cells. In some embodiments, the activation of the antigen presenting cells is characterized by elevated expression of CD80+ and CD86+ on dendritic cells.

In some embodiments, the serum levels of cytokine IL-2 and/or chemokine GM-CSF, G-CSF in the subject are increased in the presence of combination of a selective dipeptidyl peptidase inhibitor and PD-1 antagonist as compared to single agent administration.

In some embodiments, the cancer has elevated levels of T-cell infiltration in the presence of combination of a selective dipeptidyl peptidase inhibitor and a PD-1 antagonist as compared to single agent administration.

In some embodiments, the cancer has suppressed/decreased levels of T-regulatory cells in the presence of combination of a selective dipeptidyl peptidase inhibitor and a PD-1 antagonist as compared to single agent administration. In some embodiments, the cancer has increased levels of NK cells and macrophages in the presence of combination of a selective dipeptidyl peptidase inhibitor and a PD-1 antagonist as compared to single agent administration With respect to target lesions, responses to therapy may include: Complete response (CR), Partial Response (PR), Progressive Disease (PD), Stable Disease (SD), Immune-related Complete Response (irCR), Immune-related Partial Response (irPR), Immune-related Progressive Disease (irPD) and Immune-related Stable Disease (irSD).

With respect to non-target lesions, responses to therapy may include: Complete Response (CR), Progressive Disease (PD), Immune-related Complete Response (irCR) and Immune-related Progressive Disease (irPD).

Specific embodiments of the present invention are as follows:

Embodiment 1. A method of enhancing an immune response in a subject, comprising administering an effective amount of a therapeutic agent(s) that act on tumors, cells in their microenvironment, immune cells or secreted products through inhibition of the activity of Dipeptidyl peptidase in combination with an immune checkpoint inhibitor to enhance the immune response in the subject, wherein the subject has been diagnosed for tumor.

Embodiment 2. The method according to embodiment 1, wherein therapeutic agent is selected from a group comprising of small molecule, antibody, nanobody, engineered peptide, engineered protein, vaccine, siRNA therapy or autologous immune enhancement therapy, preferably small molecule.

Embodiment 3. The method according to embodiments 1 and 2, wherein the therapeutic agent comprises a selective dipeptidyl peptidase inhibitor which includes the inhibition of fibroblast activation protein and/or dipeptidyl peptidase 8/9.

Embodiment 4. The method according to embodiment 2, wherein said small molecule is Talabostat.

Embodiment 5. A method of treatment of proliferative diseases, including tumor, which comprises administering to a subject in need thereof a synergistically, therapeutically effective amount of a selective dipeptidyl peptidase inhibitor in combination with an immune checkpoint inhibitor.

Embodiment 6. Use of a therapeutic agent which selectively inhibits the activity of dipeptidyl peptidase including fibroblast activation protein or dipeptidyl peptidase 8/9 in combination with an immune checkpoint inhibitor in the manufacture of pharmaceutical composition for the treatment of tumor.

Embodiment 7. A method of treatment of proliferative diseases, including tumor which comprises administering to a subject in need thereof a synergistically, therapeutically effective amount of Talabostat in combination with an immune checkpoint inhibitor.

Embodiment 8. Use of Talabostat in combination with an immune checkpoint inhibitor in the manufacture of pharmaceutical composition for the treatment of tumor.

Embodiment 9. A selective dipeptidyl peptidase inhibitor for use in the treatment of a tumor ameliorated by stimulation of an immune response, wherein in said treatment an immune checkpoint inhibitor, is co-administered.

Embodiment 10. Talabostat for use in the treatment of a tumor ameliorated by stimulation of an immune response, wherein in said treatment an immune checkpoint inhibitor, is co-administered.

Embodiment 11. A combination therapy for the treatment of tumor, the said combination comprises
 (i) an effective amount of a selective dipeptidyl peptidase inhibitor(s) and
 (ii) an effective amount of an immune checkpoint inhibitor(s).

Embodiment 12. A combination therapy for the treatment of tumor, the said combination comprises
 i. an effective amount of Talabostat and
 ii. an effective amount of an immune checkpoint inhibitor(s).

Embodiment 13. A method for treating tumor comprising administering to a subject in need thereof
 (i) an effective amount of a selective dipeptidyl peptidase inhibitor(s) and
 (ii) an effective amount of an immune checkpoint inhibitor(s)
to provide a combination therapy having an enhanced therapeutic effect compared to the effect of the selective dipeptidyl peptidase inhibitor and the immune checkpoint inhibitor each administered alone.

Embodiment 14. The method according to embodiments 1, and 5 to 13, wherein said immune checkpoint inhibitor is selected from the group comprising PD-1 antagonist, PD-L1 antagonist, PD-L2 antagonist CTLA4 antagonist, VISTA antagonist, TIM3 antagonist, LAG3 antagonist, IDO antagonist, KIR2D antagonist, A2AR antagonist, B7-H3 antagonist, B7-H4 antagonist, BTLA antagonist and the preferred one is PD1 axis antagonist, CTLA4 antagonist or combination thereof.

Embodiment 15. The method according to embodiments 5, 6, 9, 11 and 13, wherein selective dipeptidyl peptidase inhibitor is selected from a group comprising of small molecule, antibody, nanobody, engineered peptide, engineered protein, vaccine, siRNA therapy or autologous immune enhancement therapy, preferably small molecule.

Embodiment 16. The method according to embodiment 15, wherein said small molecule is Talabostat.

Embodiment 17. The method according to embodiments 1 and 5 to 13, wherein the tumor is solid tumor or heme malignancy.

Embodiment 18. The method according to embodiment 17, wherein the tumor/cancer is selected from the group comprising of pancreatic cancer, colorectal cancer, ovarian cancer, lung cancer, breast cancer, glioblastoma, gastric cancer, astroglial, neuroectodermal tumors, head and neck squamous cell cancer, triple negative breast cancer, gastroesophageal cancer, non-small cell lung cancer, metastatic melanoma and the like.

Embodiment 19. The method according to embodiment 14, wherein PD-1 antagonist is selected from group comprising of ANA011, BGB-A317, KD033, Pembrolizumab, MCLA-134, mDX400, MEDI0680, muDX400, Nivolumab, PDR001, PF-06801591, Pidilizumab, REGN-2810, SHR 1210, STI-A1110, TSR-042, ANB011, 244C8, 388D4, TSR042 and XCE853 and the preferred one is Pembrolizumab, Nivolumab or Pidilizumab.

Embodiment 20. The method according to embodiment 14, wherein PD-L1 antagonist is selected from group comprising of Avelumab, BMS-936559, CA-170, Durvalumab, MCLA-145, SP142, STI-A1011, STI-A1012, STI-A1010, STI-A1014, A110, KY1003 and Atezolimumab and the preferred one is Durvalumab or Atezolimumab.

Embodiment 21. The method according to embodiment 14, wherein PD-L2 antagonist is selected from selected from AMP-224 and rHIgM12B7.

Embodiment 22. The method according to embodiment 14, wherein CTLA4 antagonist is selected from group comprising of KAHR-102, AGEN1884, ABRO02, KN044, Tremelimumab and Ipilimumab, and the preferred one is Tremelimumab and Ipilimumab.

Embodiment 23. A pharmaceutical composition comprising:
(i) an effective amount of a selective dipeptidyl peptidase inhibitor(s);
(ii) an effective amount of an immune checkpoint inhibitor(s) and
(iii) a pharmaceutically acceptable carrier or adjuvant(s)
wherein administering the composition to a subject having a tumor treats, prevents or delays tumor growth or metastases in the subject.

Embodiment 24. A pharmaceutical composition comprising:
(i) an effective amount of a selective dipeptidyl peptidase inhibitor(s);
(ii) an effective amount of an immune checkpoint inhibitor(s) and
(iii) an effective amount of an optional anti-tumor agent(s) and
one or more pharmaceutically acceptable carrier(s) or adjuvant(s)
wherein administering the composition to a subject having a tumor treats, prevents or delays tumor growth or metastasis in the subject.

Embodiment 25. A pharmaceutical composition for use in combination with an immune checkpoint inhibitor for treating a tumor, wherein the pharmaceutical composition comprises Talabostat together with one or more pharmaceutically acceptable carrier(s) or adjuvant(s).

Embodiment 26. The pharmaceutical composition according to embodiment 25, wherein the Talabostat is formulated as a tablet which comprises lactose and microcrystalline cellulose as a diluent, pregelatinized starch as a binder, crospovidone as a disintegrant, stearic acid as a lubricant and optionally sodium phosphate monobasic monohydrate and phosphoric acid as a pH modifier.

Embodiment 27. The pharmaceutical composition according to embodiment 25, wherein the Talabostat is formulated as a modified release tablet which comprises lactose and microcrystalline cellulose as a diluent, hydroxyl propyl methyl cellulose or hydroxyl propyl cellulose or polyvinylpyrrolidone as a modified release material, stearic acid as a lubricant and optionally sodium phosphate monobasic monohydrate and/or phosphoric acid as a pH modifier.

Embodiment 28. A method of treatment of proliferative diseases, including tumor, which comprises administering to a subject in need thereof a synergistically, therapeutically effective amount of a selective dipeptidyl peptidase inhibitor in combination with CAR-T or CAR-NK cells.

Embodiment 29. The composition according to embodiments 23 and 24 wherein selective dipeptidyl peptidase inhibitor is selected from a group comprising of small molecule, antibody, nanobody, engineered peptide, engineered protein, vaccine, siRNA therapy or autologous immune enhancement therapy, preferably small molecule.

Embodiment 30. The pharmaceutical composition according to embodiment 29, wherein said small molecule is Talabostat.

Embodiment 31. The pharmaceutical composition according to embodiments 30, wherein the Talabostat is formulated as a tablet, capsule, suspension, solution, extended release tablet, controlled release tablet, extended release capsule, controlled release capsule, liposome, microparticles, nanoparticles and the like.

Embodiment 32. The pharmaceutical composition according to embodiment 26 and 27, wherein said pharmaceutical composition is free of organic acid.

Embodiment 33. The pharmaceutical composition according to embodiments 23 and 24, wherein selective dipeptidyl peptidase inhibitor is administered via a route of administration selected from the group consisting of: orally, buccally, intravenously, subcutaneously, intra-arterially, intramuscularly, transdermally, inhalation, and any combination thereof, preferably orally.

Embodiment 34. A method for treating a proliferative disease including tumor, comprising: administering a first composition comprising a selective dipeptidyl peptidase inhibitor wherein the selective dipeptidyl peptidase inhibitor is a small molecule; and then, administering a second composition comprising an immune checkpoint inhibitor, wherein the selective dipeptidyl peptidase inhibitor is administered simultaneously, sequentially or intermittently with the immune checkpoint inhibitor.

Embodiment 35. The method according to embodiment 34, wherein the compositions are administered by the same route of administration or a different route of administration.

Embodiment 36. A kit comprising
(i) a first composition comprising a selective dipeptidyl peptidase inhibitor(s) and
(ii) a second composition comprising an immune checkpoint inhibitor(s).

Embodiment 37. A kit which comprises a first container, a second container and a package insert, wherein the first container comprises at least one dose of a pharmaceutical composition comprising an immune checkpoint inhibitor, the second container comprises at least one dose of a pharmaceutical composition comprising Talabostat, and the package insert comprises instructions for treating a subject for cancer using the pharmaceutical compositions.

Embodiment 38. A kit for treating a subject afflicted with a tumor, the kit comprising:
(i) a dosage ranging from about 0.001 mg/kg to 0.035 mg/kg body weight of Talabostat;
(ii) a dosage ranging from about 0.1 mg/kg to 20.0 mg/kg body weight of an immune checkpoint inhibitor inhibits immune checkpoint target and
(iii) instructions for using the Talabostat and an immune checkpoint inhibitor.

Embodiment 39. A method for identifying a patient diagnosed for tumor associated with increased level of dipeptidyl peptidase (FAP or DPP8/9) and/or an immune checkpoint target(s) having an increased probability of obtaining improved overall survival following co-administration treatment therapy with a selective dipeptidyl peptidase inhibitor and an immune checkpoint inhibitor(s).

Embodiment 40. A method of treating, delaying or preventing the metastasis of tumor in a subject, comprising administering to the subject an effective amount of a selective dipeptidyl peptidase inhibitor in combination with a PD-1 axis antagonist, wherein the subject has been diagnosed for tumor associated with increased levels of DPP (FAP or DPP8/9) and/or PD-1 axis.

Embodiment 41. A method of treating, delaying or preventing the metastasis of tumor in a subject comprising administering to the subject an effective amount of a selective dipeptidyl peptidase inhibitor in combination with a CTLA4 antagonist, wherein the subject has been diagnosed for tumor associated with increased levels of DPP (FAP or DPP8/9) and/or CTLA4.

Embodiment 42. A method of treating a subject receiving an immune checkpoint inhibitor for the treatment of cancer, the improvement comprising administering an effective amount of selective dipeptidyl peptidase inhibitor to the subject in conjunction with said immune checkpoint inhibitor, wherein the effect is to enhance the anti-tumor effects of said immune checkpoint inhibitor, wherein said immune checkpoint inhibitor is PD-1 antagonist, PD-L1 antagonist, PD-L2 antagonist, CTLA4 antagonist.

Embodiment 43. A method of enhancing proinflammatory cytokines production in a human having tumor, comprising administering therapeutically effective amounts of (i) Talabostat and an (ii) an immune checkpoint inhibitor to a human having a tumor, wherein the combination of the Talabostat and the immune checkpoint inhibitor provide a synergistic increase in proinflammatory cytokines production, wherein said immune checkpoint inhibitor is PD-1 antagonist, PD-L1 antagonist, PD-L2 antagonist, CTLA4 antagonist.

Embodiment 44. A method of inducing apoptosis in a tumor, comprising administering to a human having tumor therapeutically effective amounts of (i) Talabostat and (ii) an immune checkpoint inhibitor to a human having a tumor, wherein the combination of the Talabostat and the immune checkpoint inhibitor provide a synergistic increase in apoptosis wherein said immune checkpoint inhibitor is PD-1 antagonist, PD-L1 antagonist, PD-L2 antagonist, CTLA4 antagonist.

Embodiment 45. A combination therapy for increasing tumor infiltrating cells, the therapy comprises: an effective amount of a selective dipeptidyl peptidase inhibitor(s); and an effective amount of PD-1 axis antagonist, wherein the tumor infiltrating cells comprises NK cells and macrophages.

Embodiment 46. A combination therapy for increasing tumor infiltrating cells, the therapy comprises: an effective amount of Talabostat and an effective amount of PD-1 axis antagonist, wherein the tumor infiltrating cells comprises NK cells and macrophages.

Embodiment 47. A combination therapy for suppressing/decreasing T-regulatory cells, the therapy comprises: an effective amount of a selective dipeptidyl peptidase inhibitor(s); and an effective amount of PD-1 axis antagonist.

Embodiment 48. A combination therapy for suppressing T-regulatory cells, the therapy comprises: an effective amount of Talabostat and an effective amount of PD-1 axis antagonist.

Embodiment 49. The method according to any of the preceding embodiments, wherein the immune checkpoint inhibitor is administered at a dose from about 0.01 to 30 mg/kg, preferably 0.1 to 20 mg/kg, more preferably 1 to 10 mg/kg.

Embodiment 50. The method according to any of the preceding embodiments, wherein the selective dipeptidyl peptidase inhibitor is administered at a dose from about 0.001 to 10 mg/kg, preferably 0.001 to 3 mg/kg, more preferably 0.001 to 2 mg/kg.

Embodiment 51. The method according to any of the preceding embodiments, wherein selective dipeptidyl peptidase inhibitor is selected from a group comprising of small molecule, antibody, nanobody, engineered peptide, engineered protein, vaccine, siRNA therapy or autologous immune enhancement therapy, preferably small molecule.

Embodiment 52. The method according to embodiment 51, wherein said small molecule is Talabostat.

Embodiment 53. The methods according to any of the preceding embodiments, wherein said immune checkpoint inhibitor is selected from the group of PD-1 antagonist, PD-L1 antagonist, PD-L2 antagonist CTLA4 antagonist, VISTA antagonist, TIM3 antagonist, LAG3 antagonist, IDO antagonist, KIR2D antagonist, A2AR antagonist, B7-H3 antagonist, B7-H4 antagonist, BTLA antagonist and the preferred one is PD1 axis antagonist, CTLA4 antagonist or combination thereof.

Embodiment 54. The method according to embodiment 40, 45, 46, 47, and 48, wherein the PD1 axis antagonist is selected from the group consisting of PD-1 antagonist, PD-L1 antagonist and PD-L2 antagonist.

Embodiment 55. The method according to embodiments 42, 43, 44, 53 and 54, wherein PD-1 antagonist is selected from group comprising of ANA011, BGB-A317, KD033, Pembrolizumab, MCLA-134, mDX400, MEDI0680, muDX400, Nivolumab, PDR001, PF-06801591, Pidilizumab, REGN-2810, SHR 1210, STI-A1110, TSR-042, ANB011, 244C8, 388D4, TSR042 and XCE853 and the preferred one is Pembrolizumab, Nivolumab or Pidilizumab.

Embodiment 56. The method according to embodiments 42, 43, 44, 53 and 54, wherein PD-L1 antagonist is selected from group comprising of Avelumab, BMS-936559, CA-170, Durvalumab, MCLA-145, SP142, STI-A1011, STI-A1012, STI-A1010, STI-A1014, A110, KY1003 and Atezolimumab and the preferred one is Durvalumab or Atezolimumab.

Embodiment 57. The method according to embodiments 42, 43, 44, 53 and 54, wherein PD-L2 antagonist is selected from selected from AMP-224 and rHIgM12B7.

Embodiment 58. The method according to embodiments 41, 42, 43, 44, and 53 wherein CTLA4 antagonist is selected from group comprising of KAHR-102, AGEN1884, ABR002, KN044, Tremelimumab and Ipilimumab, and the preferred one is Tremelimumab and Ipilimumab.

Embodiment 59. The method according to embodiments 2, 15, 29 and 51 wherein the small molecule is ARI-3099, MIP-1231, (4-quinolinoyl)-glycyl-2-cyanopyyrolidine, -(2-(1-Napthoylamino)acetyl)pyrroline-2-carbonitrile, (2S)-1-((2S)-2-(2-Methoxybenzoylamino)-3-methylpentanoyl) pyrrolidine-2-carbonitrile, Ac-Gly-BoroPro, GEH200200, UAMC-1110, UAMC00132, 1G244, PTX-1200, UAMC00071, (2S)-2-Amino-4-(4-((4-chlorophenyl)(phenyl)methyl)piperazin-1-yl)-1-(5-fluoroisoindolin-2-yl)butane-1,4-dione bis-(2,2,2-trifluoroacetate); (2S)-2-Amino-4-(4-((4-chlorophenyl)(phenyl)methyl)piperazin-1-yl)-1-(isoindolin-2-yl)butane-1,4-dione bis(2,2,2-trifluoroacetate); (S)-2-Amino-4-((S)-4-(bis(4-fluorophenyl) methyl)-3-methyl-piperazin-1-yl)-1-(isoindolin-2-yl) butane-1,4-dione Bis(2,2,2-tri-fluoroacetate); (2S)-2-Amino-4-((3R)-4-((3-fluorophenyl)(4-fluorophenyl)-methyl)-3-methylpiperazin-1-yl)-1-(isoindolin-2-yl)butane-1,4-dione Bis(2,2,2-trifluoroacetate, SUMO1 EIL Peptide.

Embodiment 60. A method of activating innate immune cells in a subject having tumor, comprising administering therapeutically effective amounts of (i) Talabostat and (ii) an immune checkpoint inhibitor to a subject, wherein the combination of the Talabostat and the immune checkpoint inhibitor provide a synergistic increase in innate immune cells, wherein said immune checkpoint inhibitor is PD-1 antagonist, PD-L1 antagonist, PD-L2 antagonist and CTLA4 antagonist.

Embodiment 61. The method according to embodiment 60, wherein the innate immune cells includes NK cells and macrophages.

Embodiment 62. A method of activating adaptive immune cells in a subject having tumor, comprising administering therapeutically effective amounts of (i) Talabostat and (ii) an immune checkpoint inhibitor to a subject, wherein the combination of the Talabostat and the immune checkpoint inhibitor provide a synergistic increase in the activity of adaptive immune cells, wherein said immune checkpoint inhibitor is PD-1 antagonist, PD-L1 antagonist, PD-L2 antagonist and CTLA4 antagonist.

Embodiment 63. The method of embodiment 62, wherein the adaptive immune cells are CD8+ T cells and the activity is associated with granzyme B release.

Embodiment 64. A method of suppressing T regulatory cells in a subject having tumor, comprising administering therapeutically effective amounts of (i) Talabostat and (ii) an immune checkpoint inhibitor to a subject, wherein the combination of the Talabostat and the immune checkpoint inhibitor provide a synergistic decrease in T regulatory cells, wherein said immune checkpoint inhibitor is PD-1 antagonist, PD-L1 antagonist, PD-L2 antagonist and CTLA4 antagonist.

Embodiment 65. The methods according to embodiments 60 and 62, wherein said immune checkpoint inhibitor is selected from the group of PD-1 antagonist, PD-L1 antagonist, PD-L2 antagonist, CTLA4 antagonist.

Embodiment 66. The method according to embodiment 65, wherein PD-1 antagonist is selected from group comprising of ANA011, BGB-A317, KD033, Pembrolizumab, MCLA-134, mDX400, MEDI0680, muDX400, Nivolumab, PDR001, PF-06801591, Pidilizumab, REGN-2810, SHR 1210, STI-A1110, TSR-042, ANB011, 244C8, 388D4, TSR042 and XCE853, and the preferred one is Pembrolizumab, Nivolumab or Pidilizumab.

Embodiment 67. The method according to embodiment 65, wherein PD-L1 antagonist is selected from group comprising of Avelumab, BMS-936559, CA-170, Durvalumab, MCLA-145, SP142, STI-A1011, STI-A1012, STI-A1010, STI-A1014, A110, KY1003 and Atezolimumab and the preferred one is Durvalumab or Atezolimumab.

Embodiment 68. The method according to embodiment 65, wherein PD-L2 antagonist is selected from selected from AMP-224 and rHIgM12B7.

Embodiment 69. The method according to embodiment 65, wherein CTLA4 antagonist is selected from group comprising of KAHR-102, AGEN1884, ABR002, KN044, Tremelimumab and Ipilimumab, and the preferred one is Tremelimumab and Ipilimumab.

Embodiment 70. A pharmaceutical composition comprising an effective amount of selective dipeptidyl peptidase inhibitor(s); and an effective amount of an immune checkpoint inhibitor(s).

Embodiment 71. A pharmaceutical composition comprising an effective amount of Talabostat; and an effective amount of an immune checkpoint inhibitor(s).

Embodiment 72. A pharmaceutical composition comprising an effective amount of Talabostat; and an effective amount of a PD-1 axis antagonist.

Embodiment 73. A pharmaceutical composition comprising an effective amount of Talabostat; and an effective amount of a PD-1 axis antagonist for treatment of proliferative disease, preferably cancer or tumor.

Embodiment 74. The pharmaceutical composition according to any of the preceding embodiments, wherein the selective dipeptidyl peptidase inhibitor is Talabostat.

Embodiment 75. The pharmaceutical composition according to any of the preceding embodiments, wherein the immune checkpoint inhibitor is PD-1 axis antagonist, preferably PD-1 antagonist.

Embodiment 76. The combination therapy according to any of the preceding embodiments, wherein the selective dipeptidyl peptidase inhibitor is Talabostat.

Embodiment 77. The combination therapy according to any of the preceding embodiments, wherein the immune checkpoint inhibitor is PD-1 axis antagonist, preferably PD-1 antagonist.

Embodiment 78. The use according to any of the preceding embodiments, wherein the selective dipeptidyl peptidase inhibitor is Talabostat.

Embodiment 79. The use according to any of the preceding embodiments, wherein the immune checkpoint inhibitor is PD-1 axis antagonist, preferably PD-1 antagonist.

Embodiment 80. The kit according to embodiment 36, wherein the selective dipeptidyl peptidase inhibitor is Talabostat and the immune checkpoint inhibitor is a PD-1 axis antagonist.

Embodiment 81. The method according to embodiment 7, wherein the Talabostat is administered at a dose from about 0.001 mg/kg to 1 mg/kg, preferably 0.001 mg/kg to 0.05 mg/kg, and more preferably about 0.001 mg/kg to 0.035 mg/kg.

Embodiment 82. The combination therapy according to Embodiment 11, wherein the Talabostat is administered at a dose from about 0.001 mg/kg to 1 mg/kg, preferably 0.001 mg/kg to 0.05 mg/kg, and more preferably about 0.001 mg/kg to 0.035 mg/kg.

Proposed Combinations of the Present Invention:

In one of the embodiments, a selective dipeptidyl peptidase inhibitor (for example Talabostat) is used in combination of an immune checkpoint inhibitor (for example PD-1 antagonist or PD-L1 antagonist or PD-L2 antagonist or CTLA4 antagonist) for the treatment of a solid tumor or cancer.

In one of the embodiments, a selective dipeptidyl peptidase inhibitor (for example Talabostat) is used in combination of an immune checkpoint inhibitor (for example PD-1 antagonist or PD-L1 antagonist or PD-L2 antagonist or CTLA4 antagonist) for the treatment of a haematological cancer.

In one of the embodiments, a selective dipeptidyl peptidase inhibitor (for example Talabostat) is used in combination of Nivolumab, Pembrolizumab, Avelumab or Ipilimumab for the treatment of the solid tumor or haematological cancer.

In one of the embodiments, Talabostat is used in combination with an immune checkpoint inhibitor (for example PD-1 antagonist or PD-L1 antagonist or PD-L2 antagonist or CTLA4 antagonist) for the treatment of the solid tumor or haematological cancer.

In one of the embodiments, a selective dipeptidyl peptidase inhibitor (for example Talabostat) is used in combination of an immune checkpoint inhibitor (for example PD-1 antagonist or PD-L1 antagonist or PD-L2 antagonist or CTLA4 antagonist) for the treatment of the solid tumor (such as pancreatic cancer, colorectal cancer, ovarian cancer, lung cancer, breast Cancer, glioblastoma, gastric cancer, astroglial, neuroectodermal tumors, head and neck cancer, triple negative breast cancer, gastroesophageal cancer, non-small cell lung cancer) or haematological cancer (leukemia, lymphoma, a lymphocytic leukemia, non-Hodgkin's lymphoma, Hodgkin's lymphoma, an anaplastic large-cell lymphoma, myeloid leukemia, multiple myeloma, acute lymphoblastic leukemia, chronic myeloid leukemia, acute myeloid leukemia).

In one of the embodiments, Talabostat is used in combination of an immune checkpoint inhibitor (for example nivolumab, Pembrolizumab, Atezolizumab, Avelumab or Ipilimumab) for the treatment of the solid tumor (such as pancreatic cancer, colorectal cancer, ovarian cancer, lung cancer, breast cancer, glioblastoma, gastric cancer, astroglial, neuroectodermal tumors, head and neck cancer, triple negative breast cancer, gastroesophageal cancer, non-small cell lung cancer) or haematological cancer (leukemia, lymphoma, a lymphocytic leukemia, non-hodgkin's lymphoma, hodgkin's lymphoma, an anaplastic large-cell lymphoma, myeloid leukemia, multiple myeloma, acute lymphoblastic leukemia, chronic myeloid leukemia, acute myeloid leukemia).

In one of the embodiments, Talabostat is used in combination of one or more immune checkpoint inhibitor (s) (for example Nivolumab, Pembrolizumab, Atezolizumab, Avelumab or Ipilimumab) for the treatment of the melanoma, non-small cell lung cancer, renal cancer, hodgkin's disease, unresectable or metastatic melanoma, gastric cancer, oesophageal cancer, urogenital cancer, hepatocellular carcinoma, glioblastoma, head and neck cancer, small cell lung cancer, breast cancer, colorectal cancer or multiple myeloma.

In one embodiment, one of Nivolumab, Pembrolizumab, Atezolizumab Avelumab or Ipilimumab is used in combination with Talabostat to treat a tumor or cancer or disorder described herein.

EXAMPLES

Example 1

Materials and Methods
Animals

Six to seven-week-old female C57BL/6 mice were used in the studies. Mice received food and water ad libitum. The study protocol, the procedures involving the care and use of animals were reviewed and approved by the Institutional Animal Care and Use Committee (IACUC) to ensure compliance with the regulations of the Association for Assessment and Accreditation of Laboratory Animal Care (AAALAC).

Reagents and Antibodies

DMEM medium (Cat. No.: 11960-044), GLUTAMAX® (Cat. No.: 35050061), Trypsin-EDTA (0.25%) (Cat. No.: 25200-056), Penicillin-Streptomycin (Cat. No.: 15070-063), HBSS (Cat. No.: 14175-095) were procured form Gibco, while Fetal Bovine Serum (FBS) Cat. No.: 004-001-1A was purchased form Biological Industries. PD1 antagonist (Cat. No.: BE0146) was supplied by BioXcell at 2 mg/ml. Stock solutions of PD-1 antagonist at 2 mg/ml were kept at 4° C. prior to use. Dosing solutions of PD-1 antagonist were prepared freshly before every administration in sterile phosphate buffered saline (pH 7.0) and maintained at 4° C. The test article Talabostat was provided by Aptuit Ltd., and prepared freshly at a stock concentration of 100 μg/ml before every administration in sterile phosphate buffered saline (pH 7.0) and maintained at 4° C. LUMINEX® assay kit: MCYTOMAG-70K-32 was commercially available form Millipore.

Tumor Model

MC38 mouse colon cancer cell line was provided by GenScript. The tumor cells were maintained as monolayer culture in DMEM supplemented with 10% fetal bovine serum (FBS), 1% Glutamax® and 1% Penicillin-Streptomycin at 37° C. in an atmosphere with 5% $CO_2$. The cells were routinely subcultured every 2 days to maintain growth at exponential phase. The tumor cells growing in exponential growth phase were harvested by trypsinization, followed by centrifugation at 335×g relative centrifugal force (RCF) in a centrifuge. The supernatant was subsequently removed by aspiration. Cell pellet was resuspended in approximately 10× volume of cell culture medium and counted. The cell suspension was centrifuged again and processed as above and finally resuspended in HBSS−/− at a density of $1\times10^7$ cells per ml. Cell viability was determined to be 95% by trypan blue staining. Cell suspensions were implanted in the subcutaneous space of the flank of mice of female C57BL/6 mice ($2.0\times10^6$ MC-38 cells in 0.2 mL Hanks Balanced Salt Solution). Mice were inoculated subcutaneously in the right lower flank (near the dorsal thigh region) with a single volume of 0.1 ml cell suspension containing about $1\times10^6$ cells.

Tumor size and body weights were measured twice weekly.

Tumor size was measured twice per week in 2 dimensions using a caliper (recorded up to one decimal point). Tumor volume, expressed in $mm^3$, was calculated using the following formula, in which "a" and "b" were the long and the short diameters of a tumor, respectively.

$$V\,(mm^3) = (a \times b^2)/2$$

Animals were weighed and randomized into treatment groups when the mean tumor size was around 120 $mm^3$ on Day 0.

Statistical Analysis

Data related to tumor volume, tumor weight, and body weight were presented as mean and the standard error of the mean (SEM). Statistical analyses were conducted using Student's t-test. P<0.05 was considered statistically significant. * and ** indicate P<0.05 and P<0.01, respectively.

Therapeutic synergy was defined as an antitumor effect in which the combination of agents demonstrated significant superiority (p<0.05) relative to the activity shown by each agent alone.

The antitumor effect of single dose (qd) as well as twice daily (bid) administration of Talabostat alone and in combination with PD-1 antagonist at various dose schedules was evaluated in MC-38 (murine colon) tumor bearing mice. After the tumors were established, mice were sorted into various groups with a mean tumor volume of ~200 $mm^3$. The test article and antibody were administered according to the dosing schedules described in Tables 5 and 6.

The immuno-modulatory effect of the single dose (qd) as well as twice daily (bid) administration of Talabostat alone and in combination with PD-1 antagonist at various dose schedules was also analyzed. For this the 100 μl blood was collected at the respective time periods after first dosing according to the study. Blood samples were collected for obtaining serum and stored at −80° C. until analysis. In case of the first study IL-2, IL-6 and G-CSF in Groups 1, 2, 4 and 6 were analyzed while for the second study the levels of G-CSF, GM-CSF, IL-2, IL-6, IL-7, IL-12 (p40), IL-15, were evaluated. In both the cases LUMINEX® analysis was used. The data was normalized.

TABLE 5

Study 1, Treatment groups and dosing schedule

| Group | Treatment | No. of Animals | Dose Talabostat (μg) | Dose PD-1 Antagonist (mg/kg) | Dosing volume Talabostat (ml) | Dosing volume PD-1 Antagonist (ml/kg) | Treatment frequency Talabostat | Treatment frequency PD-1 Antagonist | Route of administration Talabostat | Route of administration PD-1 Antagonist | Treatment duration |
|---|---|---|---|---|---|---|---|---|---|---|---|
| 1 | Vehicle* | 10 | — | — | — | — | — | — | — | — | Day 11 |
| 2 | PD-1 antagonist | 10 | — | 5 | — | 2.5 | — | Twice per week | — | i.p. | Day 32 |
| 3 | PD-1 antagonist | 10 | — | 10 | — | 5 | — | Twice per week | — | i.p. | Day 32 |
| 4 | Talabostat | 10 | 10 | — | 0.1 | — | Twice daily | — | p.o. | — | 32 days |
| 5 | Talabostat | 10 | 20 | — | 0.2 | — | Twice daily | — | p.o. | — | 32 days |
| 6 | Talabostat + PD-1 antagonist | 10 | 10 | 5 | 0.1 | 2.5 | Twice daily | Twice per week | p.o. | i.p. | 32 days |
| 7 | Talabostat + PD-1 antagonist | 10 | 20 | 5 | 0.2 | 2.5 | Twice daily | Twice per week | p.o. | i.p. | 32 days |
| 8 | Talabostat + PD-1 antagonist | 10 | 10 | 10 | 0.1 | 5 | Twice daily | Twice per week | p.o. | i.p. | 32 days |
| 9 | Talabostat + PD-1 antagonist | 10 | 20 | 10 | 0.2 | 5 | Twice daily | Twice per week | p.o. | i.p. | 32 days |
| 10 | Vehicle | 5 | — | — | — | — | — | — | — | — | 20 days |
| 11 | Talabostat + PD-1 antagonist | 5 | — | 5 | 0.2 | 2.5 | — | Twice per week | — | i.p. | 20 days |

TABLE 6

Study 2, Treatment groups and dosing schedule

| Group | Treatment | No. of Animals | Dose Talabostat (μg) | Dose PD-1 Antagonist (mg/kg) | Dosing volume Talabostat (μl) | Dosing volume PD-1 Antagonist (ml/kg) | Treatment frequency Talabostat | Treatment frequency PD-1 Antagonist | Route of administration Talabostat | Route of administration PD-1 Antagonist | Treatment duration |
|---|---|---|---|---|---|---|---|---|---|---|---|
| 1 | Vehicle* | 10 | — | — | 200 | 2.5 | bid | Biw | p.o. | i.p. | Day 11 |
| 2 | PD-1 antagonist | 10 | — | 5 | — | 2.5 | — | Biw | — | i.p. | Day 11 |
| 3 | Talabostat | 10 | 5 | — | 50 | — | bid | — | p.o. | — | Day 11 |
| 4 | Talabostat | 10 | 10 | — | 100 | — | bid | — | p.o. | — | Day 11 |
| 5 | Talabostat | 10 | 20 | — | 200 | — | qd | — | p.o. | — | Day 21 |
| 6 | Talabostat + PD-1 antagonist | 10 | 5 | 5 | 50 | 2.5 | bid | Biw | p.o. | i.p. | Day 21 |
| 7 | Talabostat + PD-1 antagonist | 10 | 10 | 5 | 100 | 2.5 | bid | Biw | p.o. | i.p. | Day 21 |
| 8 | Talabostat + PD-1 antagonist | 10 | 20 | 5 | 200 | 2.5 | qd | Biw | p.o. | i.p. | Day 21 |
| 9 | Talabostat | 10 | 2.5 | — | 25 | — | bid | — | p.o. | — | Day 11 |
| 10 | Talabostat + PD-1 antagonist | 10 | 2.5 | 5 | 25 | 2.5 | bid | Biw | p.o. | i.p. | Day 21 |

TABLE 7

Effect of Talabostat as a single agent and in combination with PD-1 antagonist on the suppression of mouse colon carcinoma

| Saline | Talabostat (10 µg) | Talabostat (20 µg) | PD-1 antagonist (5 mg/Kg) | PD-1 antagonist (10 mg/kg) | Talabostat (10 µg) + PD-1 antagonist (5 mg/kg) | Talabostat (10 µg) + PD-1 antagonist (10 mg/kg) | Talabostat (20 µg) + PD-1 antagonist (5 mg/kg) | Talabostat (20 µg) + PD-1 antagonist (10 mg/kg) |
|---|---|---|---|---|---|---|---|---|
| 2.02 (±0.49) | 1.66 (±0.48) | 1.30 (±0.42) | 0.873 (±0.18) | 1.30 (±0.43) | 0.23 (±0.11) | 1.49 | 0.40 (±0.15) | 0.40 (±0.15) |

T = Talabostat;
PD1 = PD-1 antagonist
Note:
Mean (±SEM) tumor volume (cc) measured Day 13

TABLE 8

Comparison of QD vs, BID dose of Talabostat in the presence or absence of PD-1 antagonist in the suppression of mouse colon carcinoma

| Saline | Talabostat (2.5 µg) BID | Talabostat (5 µg) BID | Talabostat (10 µg) BID | Talabostat (20 µg) QD | PD1 antagonist (5 mg/kg) | Talabostat (2.5 µg) + PD-1 antagonist (5 mg/kg) | Talabostat (5 µg) + PD-1 antagonist (5 mg/kg) | Talabostat (10 µg) + PD-1 antagonist (5 mg/kg) | Talabostat (20 µg) + PD-1 antagonist (5 mg/kg) |
|---|---|---|---|---|---|---|---|---|---|
| 3.52 (±0.49) | 3.2 (±0.48) | 2.9 (±0.42) | 2.9 (±0.18) | 2.0 (±0.43) | 2.8 (±0.11) | 2.00 | 1.20 (±0.15) | 1.19 (±0.15) | 0.9 (±0.15) |

T = Talabostat;
PD1 = anti-PD1
Note:
Mean (±SEM) tumor volume (cc) measured Day 11
Biw = biweekly,
p.o. = peroral,
i.p. = intraperitoneal;
BID = bis in die,
QD = Quaque die,
cc = cubic centimeter Results: In the first study (as tabulated in Table 5) mice were treated with Talabostat 10 µg or 20 µg bid, given either alone or in combination with 5 and 10 mg/kg PD-1 antagonist. Animals were randomized into treatment groups when the mean tumor size was around 175 mm³ on Day 0. Mice were given twice a week injection of PD-1 antagonist or vehicle. Saline control or Talabostat by oral gavage was administered bid. Mice of the vehicle control group were euthanized on Day 13 after dosing due to tumor size over 2,000 mm³. From Day 8 to 13, Talabostat and PD-1 antagonist combination therapy exhibited as significant decrease in tumor volume as compared to the single agent administration of either of the two agents. Moreover, Talabostat and PD-1 antagonist single treatment groups also showed significant better effect as compared with the vehicle control group (FIG. 1 and table 7). The 20 µg bid Talabostat dose when combined with PD-1 antagonist showed poor tolerability with several treated animals undergoing early deaths.

Figure 2:
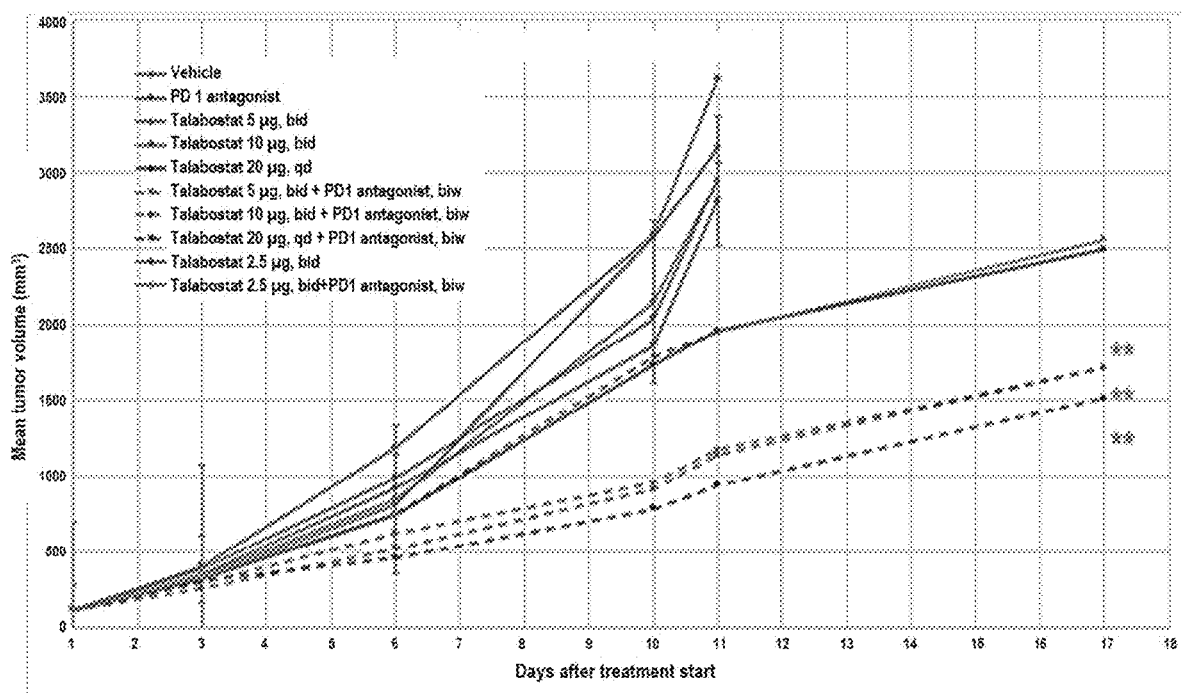
FIG. 2: shows the dose-dependent anti-tumor efficacy of Talabostat as a single agent or in combination with 5 mg/kg PD-1 antagonist (BioXcell; Cat. No. BPO146) in MC38 mouse model of colon adenocarcinoma. It also indicates the synergistic antitumor effect of the combination, and also indicates the equivalent efficacy dose of Talabostat (20 µg qd is as efficacious as 10 µg bid).
Figure 3A:
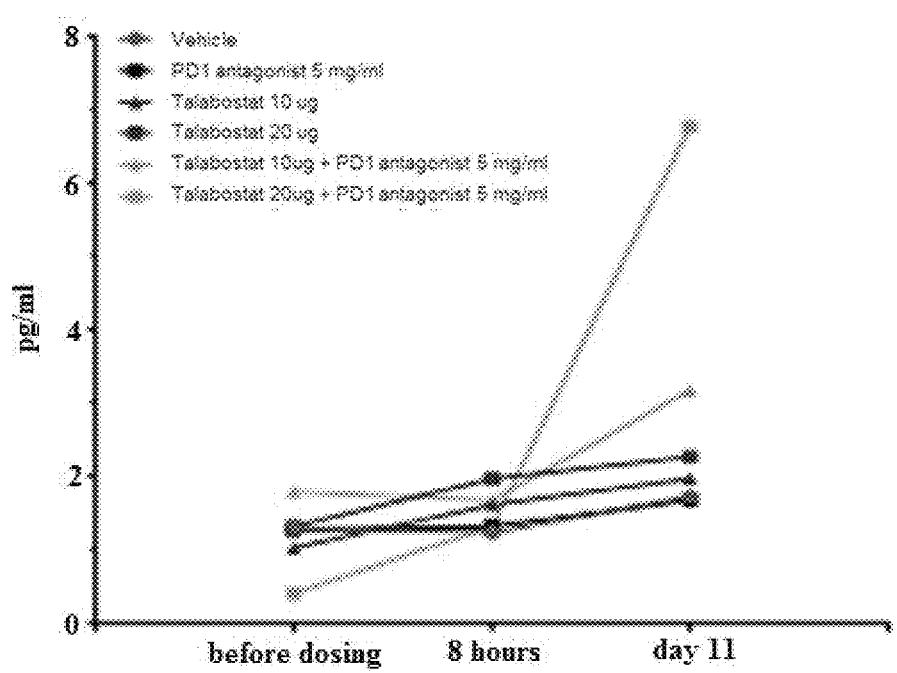
FIGS. 3A-G: shows the effect of single agent versus the combination of Talabostat and PD-1 antagonist (BioXcell; Cat. No. BPO146) for the release of proinflammatory cytokines and chemokines. The combination shows pronounced synergistic effect in comparison to single agent as seen in the increase of the secretion profiles of IL-2 (FIG. 3A), GM-CSF (FIG. 3B), IL-12p40 (FIG. 3C), IL-6 (FIG. 3D), G-CSF (FIG. 3E), IL-15 (FIG. 3F), IL-7 (FIG. 3G) release as analyzed by LUMINEX® in serum samples of mice bearing MC38 colon adenocarcinoma with indicated treatment groups and time points.
Figure 3B:
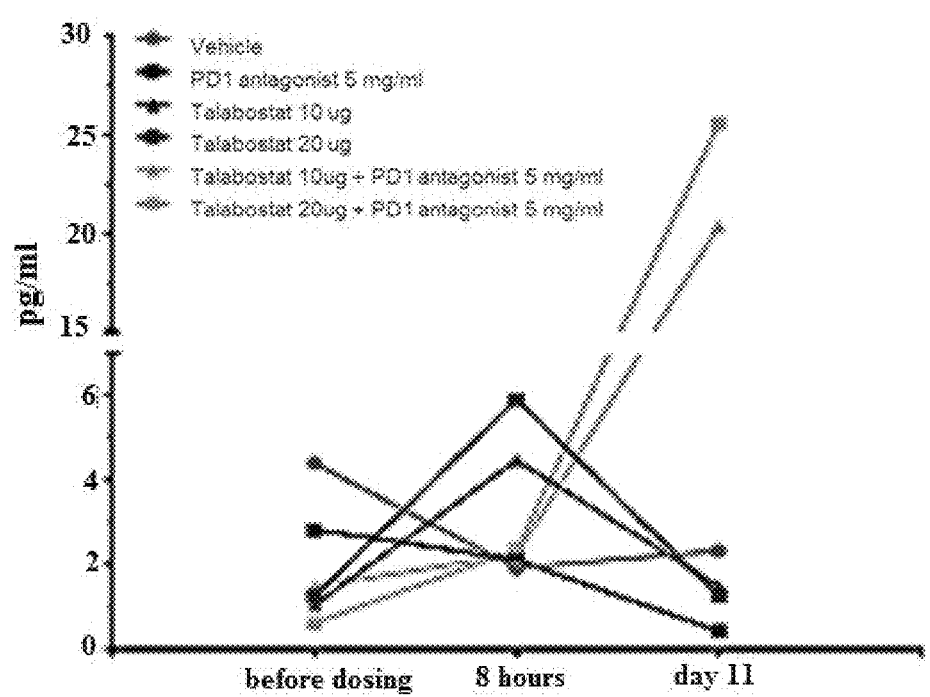
Figure 3C:
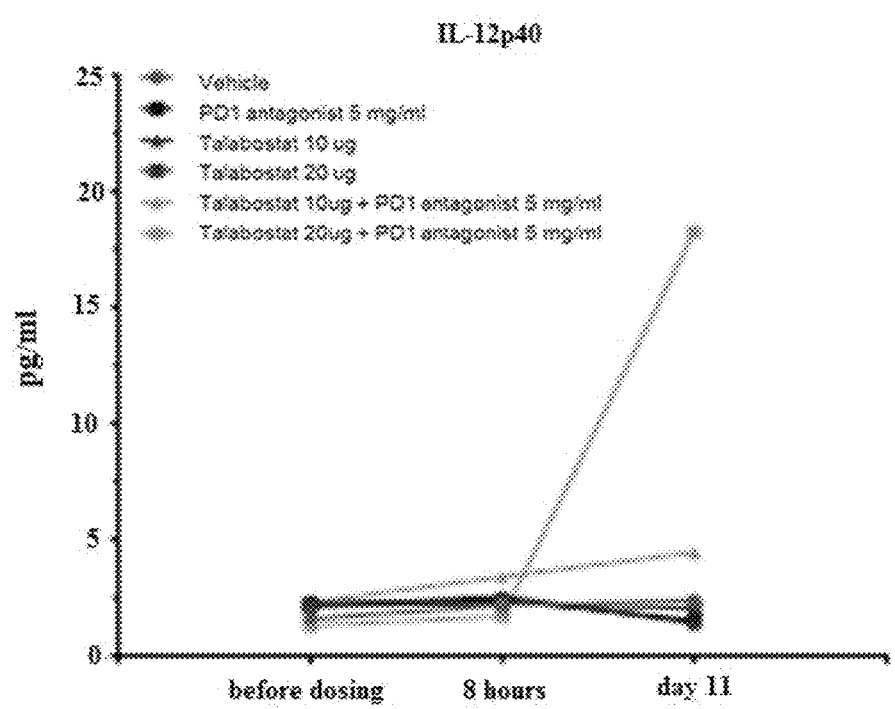
Figure 3D:
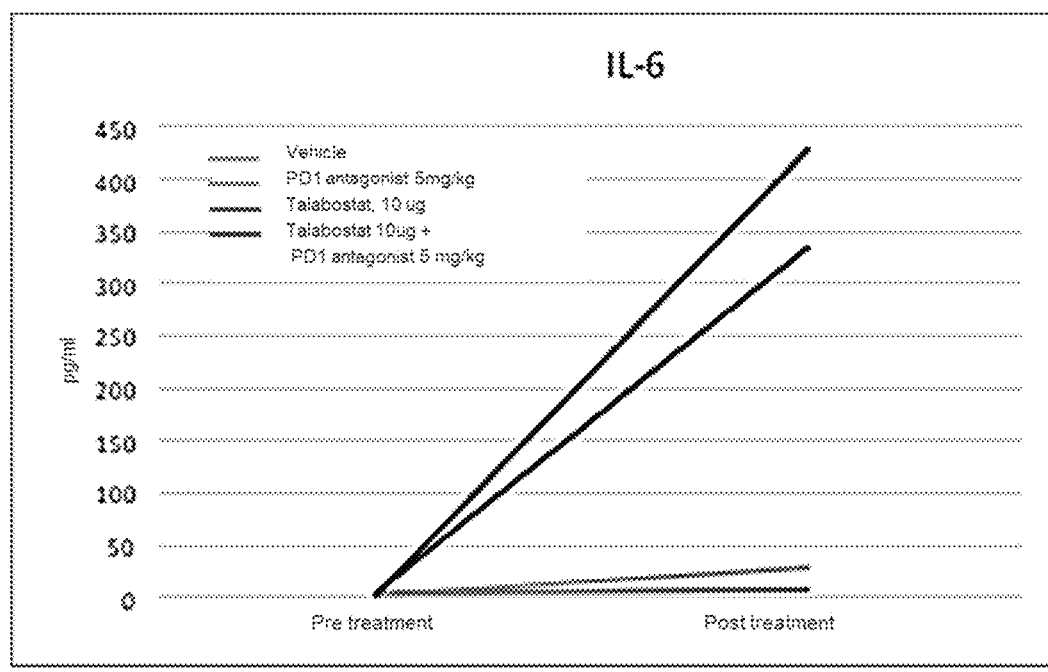
Figure 3E:
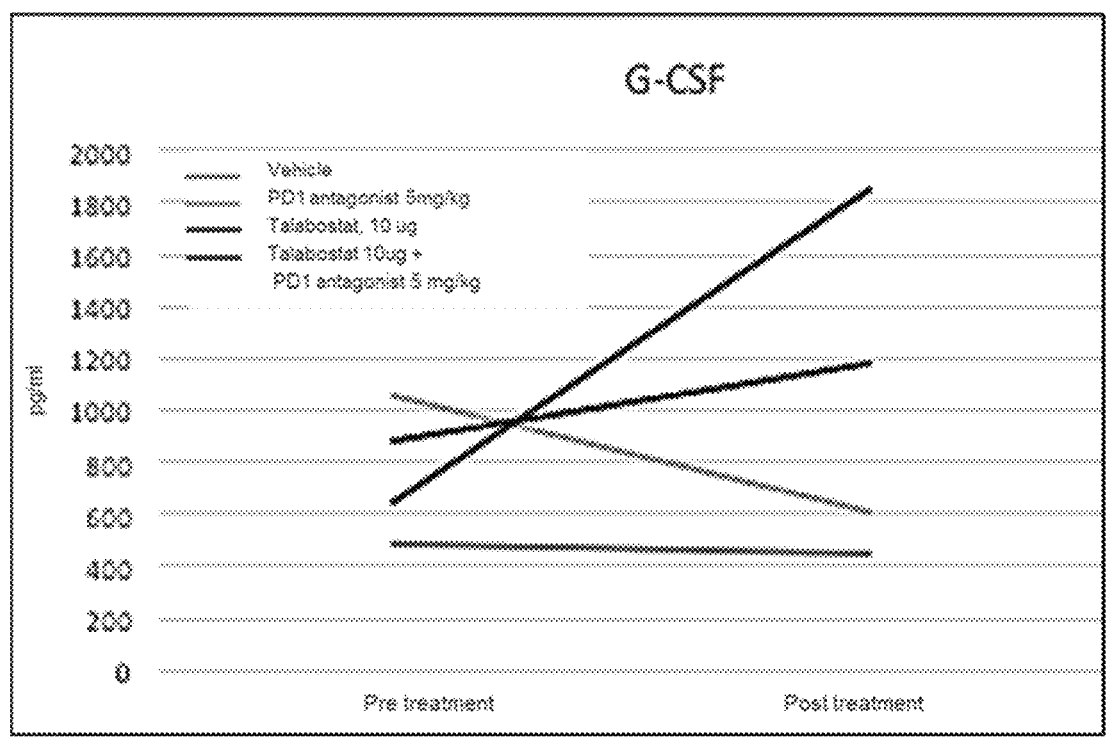
Figure 3F:
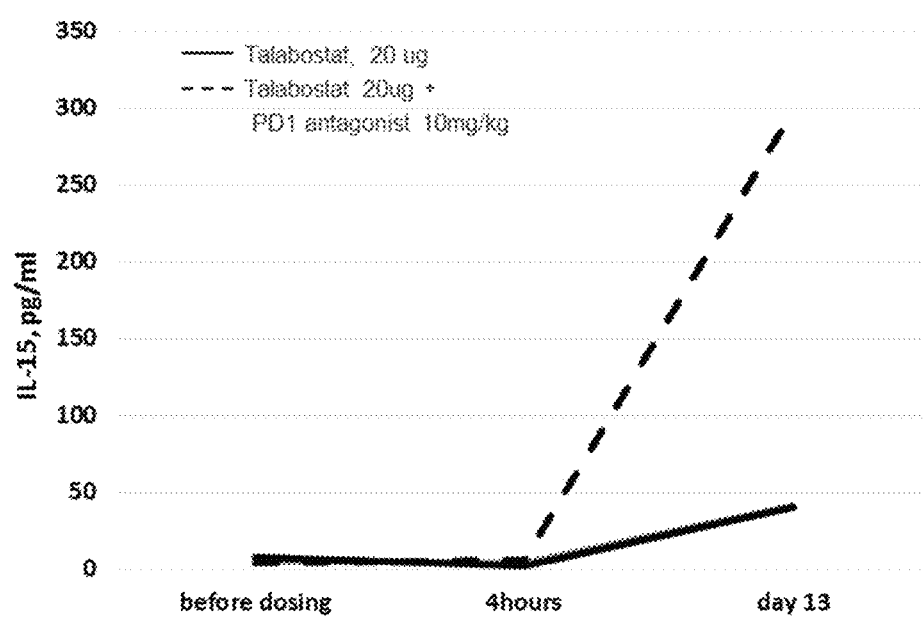
Figure 3G:
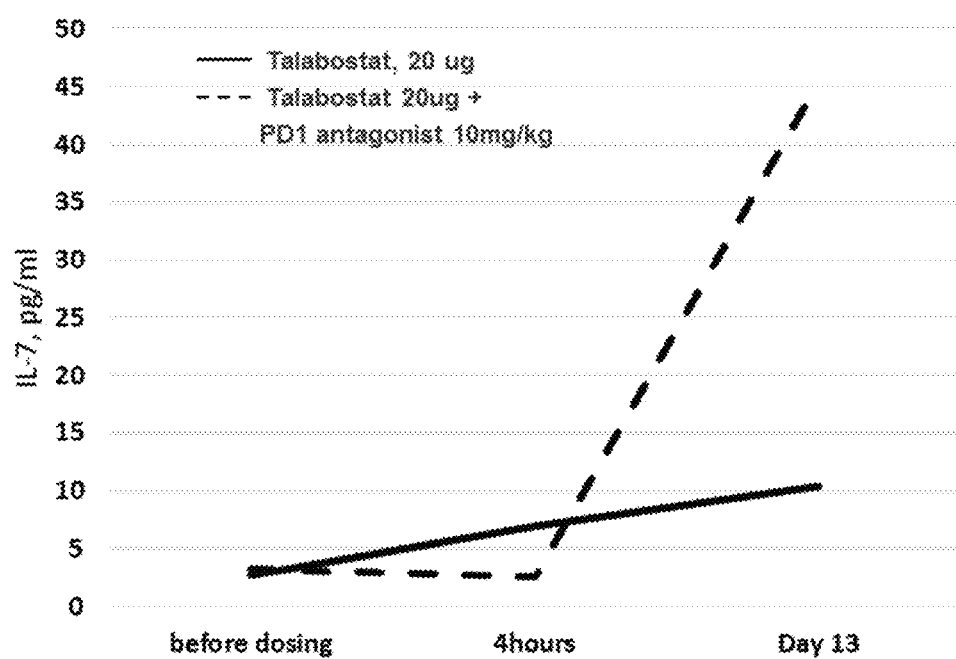

In a second experiment (as tabulated in Table 6) mice were treated with Talabostat at 2.5, 5 and 10 µg bid or 20 µg qd, given either alone or in combination with 5 mg/kg PD-1 antagonist. Animals were randomized into treatment groups and when the mean tumor size was around 120 mm³ on Day 0. Mice were given twice a week injection of PD-1 antagonist or vehicle. Saline control or Talabostat by oral gavage was administered bid or qd. Mice of vehicle control group were euthanized on Day 11 after dosing due to tumor size over 3,000 mm³. From Day 8, 5, and 10 µg bid and 20 µg qd Talabostat and PD-1 antagonist combination therapy exhibited significant better effect as compared with the corresponding Talabostat and PD-1 antagonist single treatment group. It is important to note that the doses of 10 µg bid and 20 µg qd when combined with PD-1 antagonist showed equivalent efficacy in terms of decrease in tumor volume (FIG. 2 and table 8).

Moreover, the immunomodulation brought about by Talabostat, showed synergistic affect upon combination with PD-1 antagonist as observed in the upregulation of proinflammatory cytokines including IL-2, IL-6, IL-12p40 as well as in the profiles of chemokines that curtail the immunosuppressive microenvironment including GM-CSF and G-CSF. In tumor-bearing mice, Talabostat administered at 20 µg qd in combination with PD-1 antagonist in the said conditions showed a synergistic effect on the release of GM-CSF, IL-2 and IL-12p40 on day 11 after the treatment while IL-6 and G-CSF showed a substantially increased in the combination 4 hours after treatment. Moreover, the combination also showed a synergism in the generation of IL-15 and IL-7, which have the common gamma chain in their receptors. As established in literature, the presence of IL-15 and IL-7 in the immune milieu reduces glycolysis while enhancing oxidative phosphorylation in activated CD8+ T cells that skews the T cells phenotype towards memory rather than effector T cells. This indicated that the combination has the potential of generating a memory T cell response (FIGS. 3A-3G).

Example 2

Materials and Methods
Animals
Mice (Balb/c) corresponding to 20±2 g weight, received food and water ad libitum. The study protocol, the procedures involving the care and use of animals were reviewed and approved by the Institutional Animal Care and Use Committee (IACUC) to ensure compliance with the regulations of the Association for Assessment and Accreditation of Laboratory Animal Care (AAALAC).

Reagents and Antibodies

DMEM medium (Cat. No.: 11960-044), GLUTAMAX® (Cat. No.: 35050061), Trypsin-EDTA (0.25%) (Cat. No.: 25200-056), Penicillin-Streptomycin (Cat. No.: 15070-063), HBSS (Cat. No.: 14175-095) were procured form Gibco, while Fetal Bovine Serum (FBS) Cat. No.: 004-001-1A was purchased form Biological Industries. PD-1 antagonist (Cat. No.: BE0146) was supplied by BioXcell, while the RBC lysis buffer was procured by SIGMA (Cat. No: R7757). Stock solutions of PD-1 antagonist was prepared at a concentration of 6.99 mg/mL in phosphate buffered saline (PBS) to be administered twice per week and was kept at 4° C. prior to use. Dosing solutions of PD-1 antagonist were prepared freshly before every administration in sterile PBS (pH 7.0) and maintained at 4° C. The test article Talabostat was provided by Aptuit, and prepared freshly at a stock concentration of 100 µg/ml before every administration in sterile PBS (pH 7.0) and maintained at 4° C. TRIZOL® reagent from SIGMA (Cat. No.: T9424). Reverse transcription kit from Takara (Cat. No.: RR047A). Quantitative PCR master mix from Invitrogen (Cat. No.: 4309155). PE-conjugated anti-CD11b Ab (Cat. No.: M1/70 from eBiosciences), Biotin conjugated anti-CD68Ab and Cy5-streptavadin were procured from AbD Serotec and APC-Cy7 conjugated anti-CD45 antibody was procured from BD Pharmingen (Cat. No.: 557659).

Thus, in order to attain a 5 mg/kg dose of PD-1 antagonist/mouse, 0.5 mg/mL was prepared by adding 1 ml of the PD-1 antagonist stock (6.99 mg/mL) in 12.98 mL PBS and a 200 µl of this working stock (0.5 mg/ml) was then administered twice per week. On the other hand, to administer Talabostat at 20 µg/mouse, added 0.56 mg of Talabostat to 5.6 mL PBS to achieve a 100 µg/ml and a 200 µl was administered to each mouse to attain a dose of 20 µg/mouse (as further provide in the dosing section and table 9). This working stock was prepared fresh before administration.

Tumor Model The CT26 tumor cells were cultured in RPMI1640 medium supplemented with 10% heat inactivated fetal bovine serum, 100 U/ml penicillin and 100 µg/ml streptomycin, at 37° C. in an incubator of 5% CO2. The tumor cells were routinely subcultured three times per week. The cells growing in an exponential growth phase were harvested and counted for tumor inoculation. Each mouse (BALB/c) was inoculated subcutaneously at the right flank with the CT26 tumor cells (1×106/mouse) in 0.1 ml growth media. When the tumor volume reached approximately 100 mm3, 48 mice were randomly grouped according to the animal body weight and tumor volume. Each group had 12 tumor-bearing mice.

Dosing

The PD-1 antagonist (5 mg/kg) was administrated by IP, twice a week for group 2 and 4. The test article Talabostat (20 µg/mouse) was administrated by PO approximately 24 hour apart between the two doses for the group 3 and 4.

TABLE 9

| Group | Test Article | Dose Level | Dose Volume (µl) | No. of Animals | Route | Dosing Schedule |
|---|---|---|---|---|---|---|
| 1. | Vehicle | — | 200 | 12 | SC | 5 D/W × 2 W |
| 2. | PD-1 antagonist | 5 mg/kg | 200 | 12 | IP | BIW × 2 W |
| 3. | Talabostat | 20 µg/mouse | 200 | 12 | PO | QD × 2 W |
| 4. | Talabostat + PD-1 antagonist | 20 µg/mouse + 5 mg/kg | 200 | 12 | PO + IP | QD × 2 W + BIW × 2 W | sc: subcutaneous,
i.p: intraperitoneal,
po: peroral,
w: week,
qd: once daily,
biw: twice a week;
5 D/W: 5 days a week The immuno-modulatory effect of the single dose (20 µg/mouse qd) administration of Talabostat alone and in combination with PD-1 antagonist (5 mg/kg), at various dose schedules was analysed by collecting the blood and the tumor samples 7 days after the first dosing the mice.

Immunophenotyping of Blood Samples for Detection of Macrophages:

The blood samples were collected from leg vein in anti-coagulant coated tubes. 5 µl of blood was mixed with staining buffer and respective antibodies, and stained on ice for 20 min, which was followed by a wash and RBC lysis. The RBC lysis reaction was terminated by adding PBS. The data were collected and analyzed on an ATTUNE Acoustic Nxt.

Immunophenotyping of Tumor Sample for Detection of NK Cells and Tregs:

Tumor RNA samples were extracted from the frozen tumor tissues using the Trizol reagent. Reverse transcription was carried out using a kit from Takara (Cat. #RR047A). Quantitative PCR were conducted using a master mix from Invitrogen (Cat. #4309155) on an ABI 7900HT Fast Real-Time PCR System. The results were analyzed using a Delta Delta Ct method. The marker gene and respective oligo sequence used in this study were from the NIH qRT-PCR primer database (mouseqprimerdepot.nih.gov) these were associated with the Ncr1 and Pfr1 (NK cell receptor) a marker characteristic to the NK cell and their activation respectively, while the Gmbz was meant for quantifying the release of granzyme B and the FoxP3 associated with CD25+CD4+ Tregs.

Results:

Immunophenotyping of the tumor samples on day 7 after the first dosing revealed that the combination of Talabostat with PD-1 antagonist increased the percentage of the cytotoxic NK cells in the tumor sample and macrophages in blood sample while a decrease in the immunosuppressive T regulatory cells in the tumor as compared the single agent and the vehicle control (as shown in FIG. 4A-E).

Figure 4A:
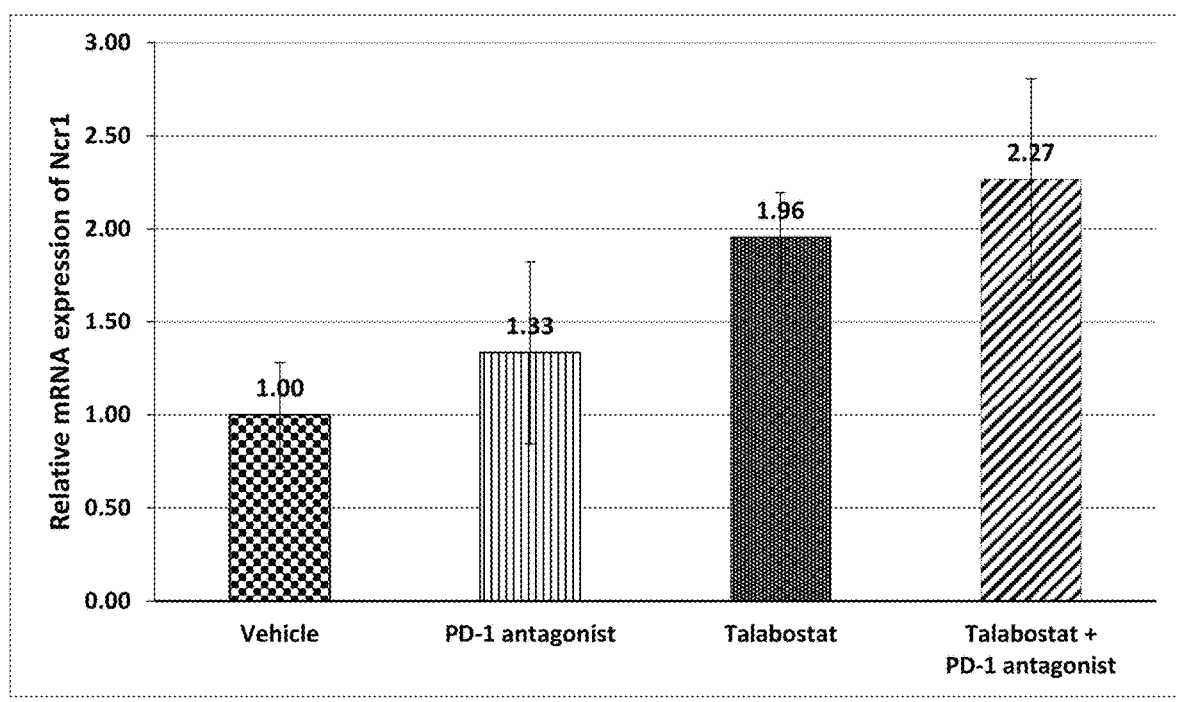
FIGS. 4A-E: shows the immunophenotyping data of single agent versus the combination of Talabostat and PD-1 antagonist (BioXcell; Cat. No. BPO146) for the increase in the cytotoxic NK cells (FIG. 4A) (relative to the mRNA levels of Ncr1) as well as increase perforin (Pfr1) release (FIG. 4B) and granzyme B (Gzmb) (FIG. 4C) in terms of relative mRNA expression in the tumor samples, while the percentage of CD68+ macrophages (FIG. 4D) in the blood. Also seen is the decrease in the immunosuppressive Foxp3+T regulatory cells relative to the mRNA levels of Foxp3+) in the tumor (FIG. 4E).
Figure 4B:
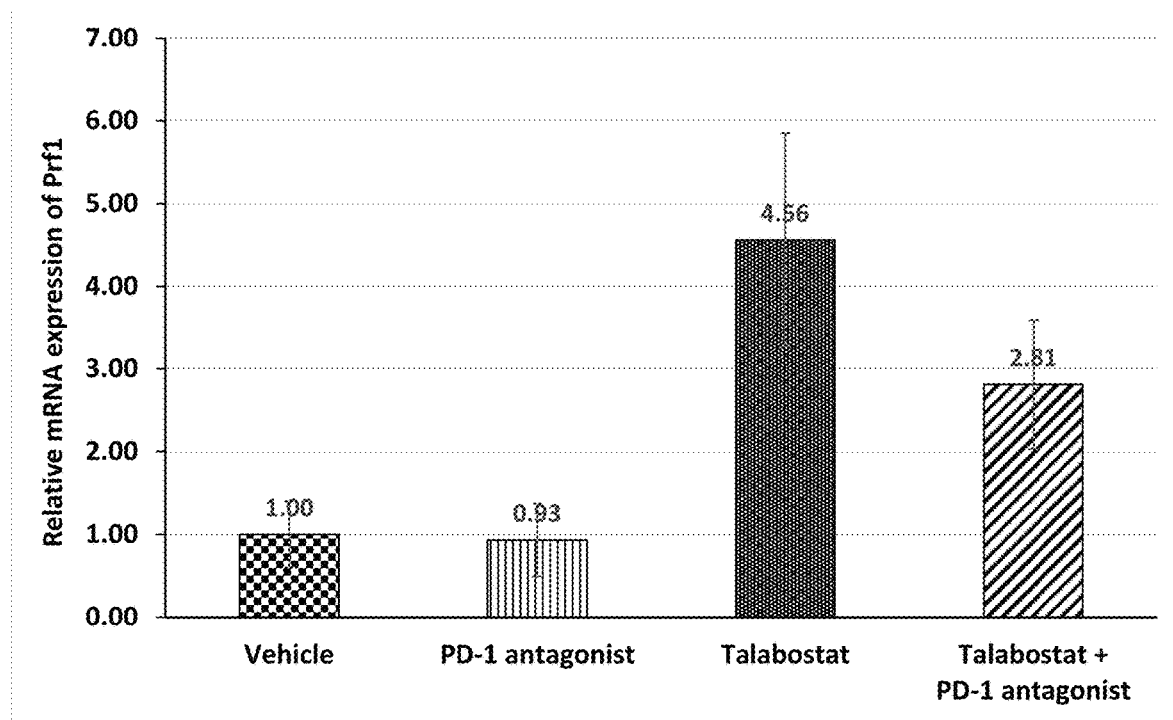
Figure 4C:
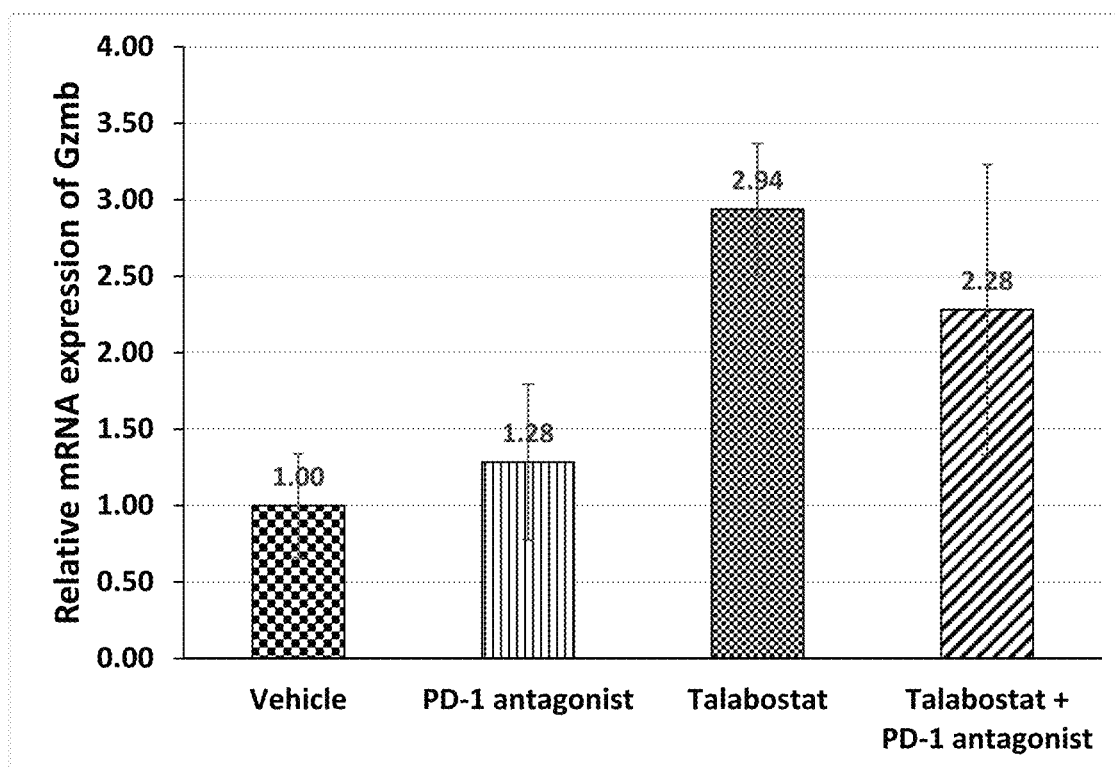
Figure 4D:
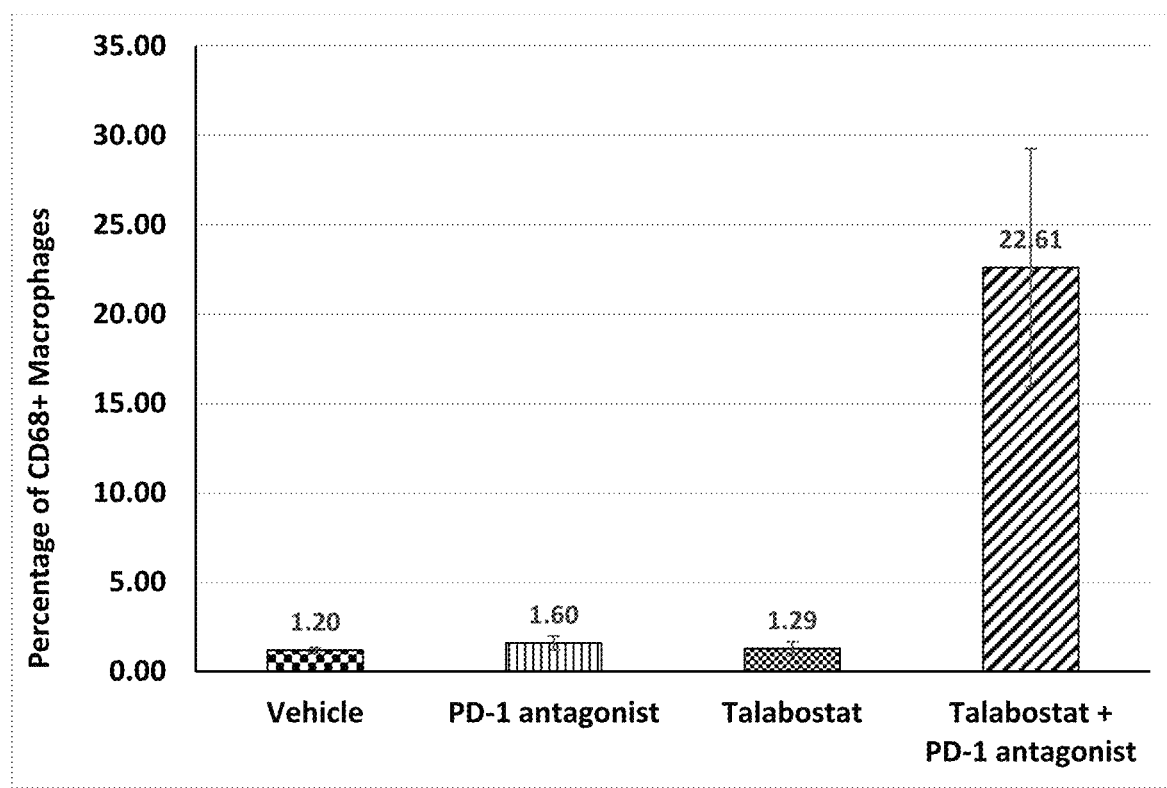
Figure 4E:
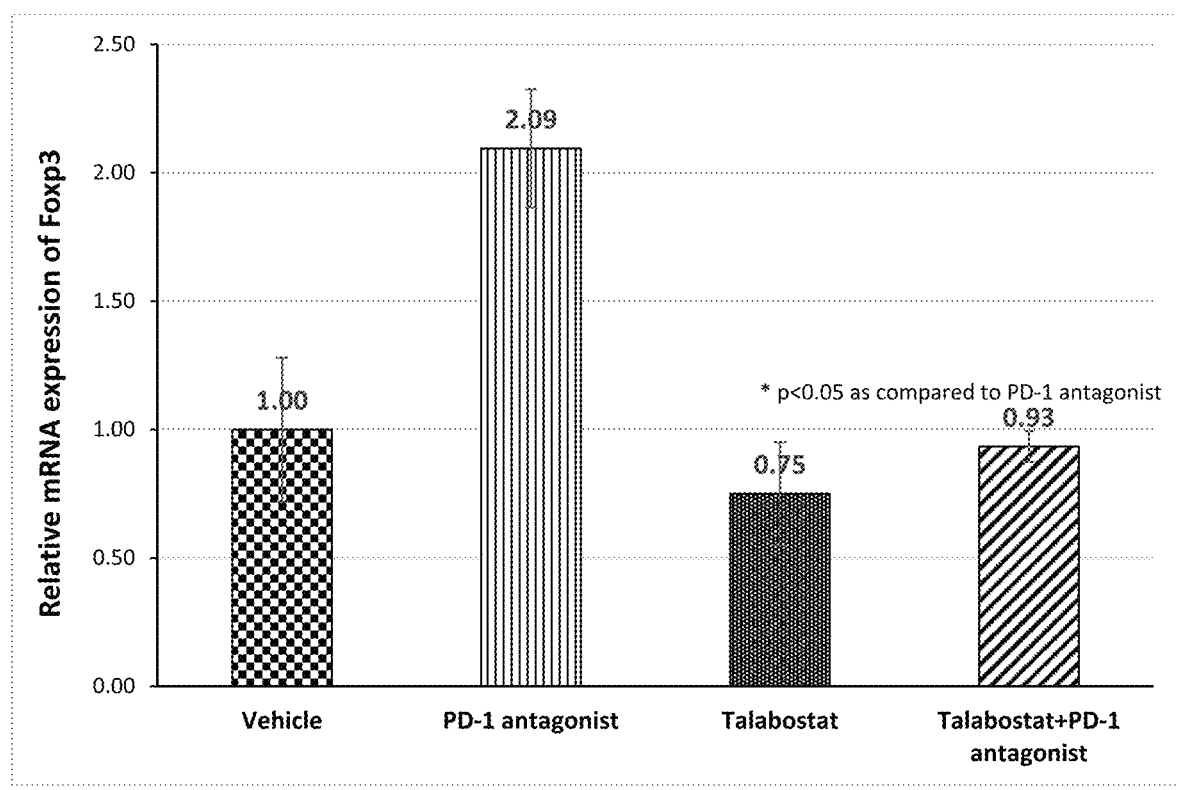

Moreover, immunophenotyping of the tumor samples showed that the combination of Talabostat with PD-1 antagonist increases the cytotoxic NK cells as well as their activation in terms of perforin and granzyme B release (FIG. 4A-C). The combination also could enhance the activation of the cytotoxic CD8+ cells in terms of increase in granzyme B release in the tumor samples analysed (FIG. 4 C). It was further observed that the percentage of macrophages in the blood samples of the groups receiving the combination of Talabostat and PD-1 antagonist had increased while a decrease in the immunosuppressive T regulatory cells was observed in the tumor tissues as compared the single agent (as shown in FIGS. 4 D and E). As understood from literature the NK cells and the macrophages comprise the cells of the innate immune system and an increase in these indicate the enhancement of innate component of the immune system while the release of granzyme B show the induction of the adaptive arm of the immune system which was hypothesized as the capability of Talabostat when combined with PD-1 antagonist.

With respect to the macrophages which are of the tumoricidal phenotype as characterized with CD68 marker were seen to be synergistically enhanced in the blood treated with the combination as compared to the single agent treated animals (FIG. 4 D).

Thereby the PD-1 antagonist when combined with Talabostat showed a synergistic increase in the infiltration of tumoricidal NK cell in the tumor while an increase in the macrophages in the blood. While the enhancement of the macrophages ensures the immune-stimulation by increase in the profiles of the cytokines, the synergistic increase in the NK cells within the tumor milieu ensures the decrease in tumor volume. These two cell types represent the innate component of the immune systems that are evoked due to the combination of Talabostat with PD-1 antagonist. The NK cells and the macrophages comprise the cells of the innate immune system and an increase in these indicates the enhancement of innate component of the immune system that is the capability of Talabostat when combined with PD-1 antagonist. It was also noted that in these tumor samples of the treated group an enhancement in the increase of the tumoricidal NK cells was accompanied by their activation in terms of release of perforin as observed in the groups receiving Talabostat alone as well as that of the group receiving combination. Further the quantification of granzyme B in the tumor samples also indicated the activation of not only NK cells but also the activation of tumoricidal CD8+ cells due to the combination.

It was also observed that in the tumor samples of the treated groups an enhanced decrease in the immunosuppressive Tregs was observed when the mice were treated with the combination of Talabostat and PD-1 as compared to the PD-1 antagonist or Talabostat alone (FIG. 4 E). Thus, as expected the presence of Talabostat in PD-1 antagonist treated mice or rather the combination of Talabostat with PD-1 antagonist was able to cause a significant reduction the FoxP3+Treg population ($p<0.05$ as compared to PD-1 antagonist) as measured in terms of the relative mRNA expression of FoxP3.

Inference: Hence it is inferred that the combining Talabostat with PD-1 antagonist was able to bring about the anti-tumor effect through immune-modulation. It was seen in terms of reduction in tumor volume as observed in the MC38 mouse model of colon adenocarcinoma (FIG. 1) along with the increase in the immune-stimulatory cytokines (FIG. 3). A validation of this effect of immune-stimulation in the tumor microenvironment is provided by the data as shown (FIG. 4A-E) in terms of immunophenotyping the cells within the tumor or blood samples. As demonstrated the analysis of the mRNA transcripts which are markers for T regs, NK cells as well as the activation markers represented by perforins and granzyme B and by the quantifying the cell surface marker that represent the macrophage population indicated the immune-regulatory phenomenon of combining Talabostat and PD-1 antagonist. The combination showed a synergistic increase in the tumoricidal NK cells as well as activation of these cells and cytotoxic CD8+ T cells and CD68+ macrophages while a significant decrease in the immune-suppressive Tregs.

VIII. Definitions

The term "subject" includes any organism, preferably an animal, more preferably a mammal (e.g., rat, mouse, dog, cat, rabbit) and most preferably a human.

As used herein the term "cancer" can be used interchangeably with "tumor". The term "cancer" refers to the cancers of wide variety of types, including both solid tumors and non-solid tumors such as leukemia and lymphoma. Carcinomas, sarcomas, myelomas, lymphomas, and leukemia can all be treated using the present invention, including those cancers which have a mixed type.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

The term "Treating" within the context of the present invention, means an alleviation of symptoms associated with a disorder or disease, or halt of further progression or worsening of those symptoms, or prevention or prophylaxis of the disease or disorder. For example, within the context of treating patients in relation to the selective dipeptidyl peptidase inhibitor and an immune checkpoint inhibitor, successful treatment may include a reduction in tumor adhesion and anchorage; an alleviation of symptoms related to a cancerous growth or tumor, or proliferation of diseased tissue; a halting in the progression of a disease such as cancer or in the growth of cancerous cells. Treatment may also include administering the pharmaceutical formulations of a selective dipeptidyl peptidase inhibitor in combination with an immune checkpoint inhibitor. It may be administered before, during, or after surgical procedure and/or radiation therapy. According to this invention, a selective dipeptidyl peptidase inhibitor and an immune checkpoint inhibitor can be co-administered into a human subject, the daily dosage will normally be determined by the prescribing physician with the dosage generally varying according to the age, weight, and response of the individual patient, as well as the severity of the patient's symptoms. When introducing elements disclosed herein, the articles "a", "an", "the", and "said" are intended to mean that there are one or more of the elements.

As used herein the term "effective amount" can be used interchangeably with "therapeutically effective dose," or "therapeutically effective amount," and it refers to an amount sufficient to produce the desired effect.

As used herein "pharmaceutical acceptable carrier" refers to a carrier medium which does not interfere with the effectiveness of the biological activity of the active ingredients and which is not toxic to the patient or subject. As used herein the term "carrier" can be used interchangeably with "adjuvant".

The term "pharmaceutical composition" as used in accordance with the present invention relates to compositions that can be formulated in any conventional manner using one or more pharmaceutically acceptable carriers or adjuvants.

The term "antibody" as used herein is meant in a broad sense and includes immunoglobulin molecules including polyclonal antibodies, monoclonal antibodies including murine, human, human-adapted, humanized and chimeric synthetic, recombinant, hybrid, mutated, engineered, grafted antibodies, antibody fragments, monospecific, bispecific or multi-specific antibodies, dimeric, tetrameric or multimeric antibodies, nanobody, single chain antibodies and antibody drug conjugate. The antibodies also include recombinant monoclonal antibody. As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, F(ab')2, Fv, scFv, bi-scFv, bi-Ab, Fd, dAb, and other antibody fragments that retain antigen-binding function, i.e., the ability to bind FAP or DPP specifically; diabodies; linear antibodies; single-chain antibody molecules, e.g., sc-Fv; nanobodies and multispecific antibodies formed from antibody fragments A nanobody (Nb) is the smallest functional fragment or single variable domain (VHH) of a naturally occurring single-chain antibody and is known to the person skilled in the art. They are derived from heavy chain only antibodies, seen in camelids (Hamers-Casterman et al. 1993; Desmyter et al. 1996). In the family of "camelids" immunoglobulins devoid of light polypeptide chains are found. "Camelids" comprise old world camelids (*Camelus bactrianus* and *Camelus dromedarius*) and new world camelids (for example *Lama paccos, Lama glama, Lama guanicoe* and *Lama vicugna*). Said single variable domain heavy chain antibody is herein designated as a Nanobody or a VHH antibody. Nanobody™, Nanobodies™ and Nanoclone™ are trademarks of Ablynx NV (Belgium).

As used herein, the term "synergy" refers generally to obtaining a combined effect that is greater than the sum of two separate effects. As used herein, the terms "therapeutic synergy", and "synergistic effect," when placed in a therapeutic context, refer to a phenomenon where treatment of patients with a combination of therapeutic agents (e.g., selective dipeptidyl peptidase inhibitor in combination with PD-1 antagonist or PD-L1 antagonist or CTLA4 antagonist) manifests a therapeutically superior outcome to the outcome achieved by each individual constituent of the combination used at its optimum dose (see, e.g., T. H. Corbett et al., 1982, Cancer Treatment Reports, 66, 1187). In this context a therapeutically superior outcome is one in which the patients either a) exhibit fewer incidences of adverse events while receiving a therapeutic benefit that is equal to or greater than that where individual constituents of the combination are each administered as monotherapy at the same dose as in the combination, or b) do not exhibit dose-limiting toxicities while receiving therapeutic benefit that is greater than that of treatment with each individual constituent of the combination when each constituent is administered in at the same doses in the combination(s) as is administered as individual components or c) both when combined produces enhanced effects as compared to when given alone, for example increase in IL-2 release. In xenograft models, a combination, used at its maximum tolerated dose, in which each of the constituents will be present at a dose generally not exceeding its individual maximum tolerated dose, manifests therapeutic synergy when decrease in tumor growth achieved by administration of the combination is greater than the value of the decrease in tumor growth of the best constituent when the constituent is administered alone.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not, be taken as an acknowledgment or any form of suggestion that they constitute valid prior art or form part of the common general knowledge in any country in the world.

The invention claimed is:

1. A method of treating prostate cancer in a subject in need thereof, comprising administering to the subject a therapeutically effective amount of Talabostat or a pharmaceutically acceptable salt thereof in combination with an anti-PD-1 antibody, wherein the prostate cancer is metastatic castration-resistant prostate cancer, wherein the anti-PD-1 antibody is Pembrolizumab, and wherein the therapeutically effective amount of Talabostat or a pharmaceutically acceptable salt thereof is 400 micrograms to 600 micrograms per day.

2. The method according to claim 1, wherein the Pembrolizumab is administered at a dose from 0.01 mg/kg to 30 mg/kg.

3. The method according to claim 1, wherein the Pembrolizumab is administered at a dose from 0.1 mg/kg to 5 mg/kg.

4. The method according to claim 1, wherein Talabostat or the pharmaceutically acceptable salt thereof is administered simultaneously, sequentially or intermittently with the anti-PD-1 antibody.

5. The method according to claim 1, wherein Talabostat or the pharmaceutically acceptable salt thereof is Talabostat mesylate.

6. The method according to claim 5, wherein Talabostat mesylate is administered simultaneously, sequentially or intermittently with the anti-PD-1 antibody.

7. The method according to claim 1 comprising a therapeutic effect of an inhibition of tumor size of at least 50%.

8. The method of claim 1, wherein Talabostat or a pharmaceutically acceptable salt thereof is administered at a dose of 600 micrograms per day.

9. The method of claim 8, wherein Talabostat or a pharmaceutically acceptable salt thereof is administered at a dose of 300 micrograms twice per day.

* * * * *

SEQUENCE LISTING

```
<160> NUMBER OF SEQ ID NOS: 5

<210> SEQ ID NO 1
<211> LENGTH: 100
<212> TYPE: PRT
<213> ORGANISM: Artificial Sequence
<220> FEATURE:
<223> OTHER INFORMATION: Synthetic peptide human FAP aa 525-625

<400> SEQUENCE: 1

Pro Pro Gln Phe Asp Arg Ser Lys Lys Tyr Pro Leu Leu Ile Gln Val
1               5                   10                  15

Tyr Gly Gly Pro Cys Ser Gln Ser Val Arg Ser Val Phe Ala Val Asn
            20                  25                  30

Trp Ile Ser Tyr Leu Ala Ser Lys Glu Gly Met Val Ile Ala Leu Val
        35                  40                  45

Asp Gly Arg Gly Thr Ala Phe Gln Gly Asp Lys Leu Leu Tyr Ala Val
    50                  55                  60

Tyr Arg Lys Leu Gly Val Tyr Glu Val Glu Asp Gln Ile Thr Ala Val
65                  70                  75                  80
```

```
Arg Lys Phe Ile Glu Met Gly Phe Ile Asp Glu Lys Arg Ile Ala Ile
                85                  90                  95

Trp Gly Trp Ser
            100

<210> SEQ ID NO 2
<211> LENGTH: 17
<212> TYPE: PRT
<213> ORGANISM: Artificial Sequence
<220> FEATURE:
<223> OTHER INFORMATION: Synthetic peptide of  N-terminus of human FAP
      aa 57-73

<400> SEQUENCE: 2

Phe Phe Pro Asn Trp Ile Ser Gly Gln Glu Tyr Leu His Gln Ser Ala
1               5                   10                  15

Asp

<210> SEQ ID NO 3
<211> LENGTH: 50
<212> TYPE: PRT
<213> ORGANISM: Artificial Sequence
<220> FEATURE:
<223> OTHER INFORMATION: Synthetic peptide of C-terminal region of Human
      FAP

<400> SEQUENCE: 3

Ser Trp Glu Tyr Tyr Ala Ser Val Tyr Thr Glu Arg Phe Met Gly Leu
1               5                   10                  15

Pro Thr Lys Asp Asp Asn Leu Glu His Tyr Lys Asn Ser Thr Val Met
            20                  25                  30

Ala Arg Ala Glu Tyr Phe Arg Asn Val Asp Tyr Leu Leu Ile His Gly
        35                  40                  45

Thr Ala
    50

<210> SEQ ID NO 4
<211> LENGTH: 77
<212> TYPE: PRT
<213> ORGANISM: Artificial Sequence
<220> FEATURE:
<223> OTHER INFORMATION: Synthetic peptide of C-terminal region of Human
      FAP

<400> SEQUENCE: 4

Glu Arg Cys Gln Tyr Tyr Thr Ala Ser Phe Ser Asp Tyr Ala Lys Tyr
1               5                   10                  15

Tyr Ala Leu Val Cys Tyr Gly Pro Gly Ile Pro Ile Ser Thr Leu His
            20                  25                  30

Asp Gly Arg Thr Asp Gln Glu Ile Lys Ile Leu Glu Glu Asn Lys Glu
        35                  40                  45

Leu Glu Asn Ala Leu Lys Asn Ile Gln Leu Pro Lys Glu Glu Ile Lys
    50                  55                  60

Lys Leu Glu Val Asp Glu Ile Thr Leu Trp Tyr Lys Met
65                  70                  75

<210> SEQ ID NO 5
<211> LENGTH: 288
<212> TYPE: PRT
<213> ORGANISM: Homo sapiens
```

```
<400> SEQUENCE: 5

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
                115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
    195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285
```